US006919369B2

(12) United States Patent
Aliagas-Martin et al.

(10) Patent No.: US 6,919,369 B2
(45) Date of Patent: *Jul. 19, 2005

(54) SERINE PROTEASE INHIBITORS

(75) Inventors: Ignacio Aliagas-Martin, San Francisco, CA (US); Dean R. Artis, Kensington, CA (US); Michael S. Dina, Daly City, CA (US); John A. Flygare, Burlingame, CA (US); Richard A. Goldsmith, Daly City, CA (US); Regina A. Munroe, San Mateo, CA (US); Alan G. Olivero, Half Moon Bay, CA (US); Richard Pastor, San Francisco, CA (US); Thomas E. Rawson, Mountain View, CA (US); Kirk D. Robarge, San Francisco, CA (US); Daniel P. Sutherlin, San Carlos, CA (US); Kenneth J. Weese, South San Francisco, CA (US); Aihe Zhou, San Jose, CA (US); Yan Zhu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 363 days.

This patent is subject to a terminal disclaimer.

(21) Appl. No.: 10/224,114

(22) Filed: Aug. 19, 2002

(65) Prior Publication Data

US 2003/0212071 A1 Nov. 13, 2003

Related U.S. Application Data

(63) Continuation of application No. 09/509,104, filed on Mar. 21, 2000, now Pat. No. 6,472,393, and a continuation of application No. PCT/US00/00673, filed on Jan. 11, 2000.
(60) Provisional application No. 60/115,772, filed on Jan. 13, 1999, and provisional application No. 60/152,029, filed on Sep. 1, 1999.

(51) Int. Cl.[7] .................. A61K 31/18; C07C 311/05
(52) U.S. Cl. ............... 514/445; 514/539; 514/562; 514/601; 514/602; 514/603; 514/604; 514/605; 549/63; 549/65; 560/13; 562/430; 564/80; 564/84; 564/86; 564/87; 564/91; 564/92; 564/99
(58) Field of Search ............... 564/80, 84, 86, 564/87, 91, 92, 99; 580/13; 562/430; 549/63, 65; 514/445, 539, 562, 601, 602, 603, 604, 605

(56) References Cited

U.S. PATENT DOCUMENTS

| 5,571,844 | A | 11/1996 | Stuber et al. ............... 514/602 |
| 5,998,424 | A | 12/1999 | Galemmo, Jr. et al. ..... 514/269 |
| 6,020,357 | A | 2/2000 | Pinto et al. ................. 514/406 |
| 6,034,103 | A | 3/2000 | Buckman et al. ........... 514/318 |
| 6,034,104 | A | 3/2000 | Klimkowski et al. ....... 514/326 |
| 6,472,393 | B1 * | 10/2002 | Aliagas-Martin et al. ... 514/247 |

FOREIGN PATENT DOCUMENTS

| DE | 19718181 A1 | 11/1998 |
| EP | 0976722 | 2/2000 |
| EP | 0987274 | 3/2000 |
| WO | WO 98/46591 | 10/1998 |
| WO | WO 98/46626 | 10/1998 |
| WO | WO 98/46627 | 10/1998 |
| WO | WO 98/46628 | 10/1998 |
| WO | WO 00/15658 | 3/2000 |

OTHER PUBLICATIONS

Glunz et al., Chemical Abstracts, vol. 141:225834, 2004.*
Renatus et al., "Structural and Functional Analyses of Benzamidine–Based Inhibitors in Complex with Trypsin: Implications for the Inhibition of Factor Xa, tPA, and Urokinase" *J. Med. Chem.* 41:5445–5456 (1998).

* cited by examiner

*Primary Examiner*—Richard L. Raymond
(74) *Attorney, Agent, or Firm*—David W. Evans; Timothy R. Schwartz; Alex Andrus

(57) ABSTRACT

Compounds having the structure shown below are useful to inhibit serine protease enzymes, such as TF/factor VIIa, factor Xa, thrombin and kallikrein. These compounds may be used in methods of preventing and/or treating clotting disorders.

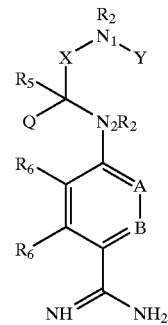

17 Claims, No Drawings

SERINE PROTEASE INHIBITORS

This is a continuation application claiming priority under 35 USC § 120 to application Ser. No. 09/509,104, filed 21 Mar. 2000, now U.S. Pat. No. 6,472,393 and International Application No. PCT/US00/00673, filed 11 Jan. 2000, and under 35 U.S.C. § 119 to provisional application Ser. Nos. 60/115,772, filed 13 Jan. 1999, and 60/152,029, filed 1 Sep. 1999, the entire disclosure of which are hereby incorporated by reference.

FIELD OF THE INVENTION

In one aspect, the invention relates to novel compounds which are inhibitors of Tissue Factor (TF)/factor VIIa, factor VIIa, factor Xa, thrombin and/or kallikrein, as well as compositions containing these compounds. The compounds are useful for inhibiting these factors and for treating disorders mediated thereby. For example, the compounds are useful for preventing thrombosis or treating abnormal thrombosis in a mammal by inhibiting TF/factor VIIa, factor Xa, thrombin and/or kallikrein.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs.

Many significant disease states are related to abnormal haemeostasis. For example, local thrombus formation due to the rupture of atherosclerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel. Furthermore, a high percentage of patients undergoing surgery, particularly in the lower extremities, suffer thrombus formation in the venous vascular system which results in reduced blood flow to the affected area.

There continues to be a need for safe and effective therapeutic anticoagulants to limit or prevent thrombus formation.

Blood coagulation is vital for the containment of bodily fluids upon tissue injury and is an important component of host defense mechanisms. Coagulation or clotting involves the sequential activation of multiple zymogens in a process leading to thrombin generation and the conversion of fibrinogen to an impermeable cross-linked fibrin clot. Thrombin production is the result of a blood coagulation cascade which has been intensively studied and increasingly characterized. See for example, Lawson, J. H., et al. (1994) J. Biol. Chem. 269:23357. The coagulation reactions of this cascade involve initiation, amplification and propagation phases. Additionally, the cascade has been divided into extrinsic and intrinsic pathways. The intrinsic pathway involves factors XII, XI, and IX and leads to the formation of a complex of factor IXa with its cofactor, factor VIIIa. This complex converts factor X to Xa. Factor Xa is an enzyme which forms a complex with its cofactor, factor Va, and rapidly converts prothrombin to thrombin. Thrombin converts fibrinogen to fibrin monomers which polymerize to form a clot. The extrinsic pathway involves factor VIIa and tissue factor, which form a complex (TF/factor VIIa), and convert factor X to Xa. As in the intrinsic pathway, factor Xa converts prothrombin to thrombin.

Thrombin (factor IIa), as noted above, occupies a central position in the coagulation cascade by converting fibrinogen to fibrin. Consequently, substantial synthetic efforts have been directed to the development of thrombin inhibitors. See, for example, U.S. Pat. No. 5,656,600; U.S. Pat. No. 5,656,645; U.S. Pat. No. 5,670,479; U.S. Pat. No. 5,646,165; U.S. Pat. No. 5,658,939; U.S. Pat. No. 5,658,930 and WO 97/30073. Additional compounds which have been prepared as synthetic thrombin inhibitors are N-arylsulfinated phenylalanine amides.

Known inhibitors of factor Xa include bisamidine compounds (Katakura, S. (1993) Biochem. Biophys. Res. Commun., 197:965) and compounds based on the structure of arginine (WO 93/15756; WO 94/13693). Phenyl and naphthylsulfonamides have also been shown to be factor Xa inhibitors (WO 96/10022; WO 96/16940; WO 96/40679).

TF/factor VIIa is a serine protease complex that participates in blood coagulation by activating factor X and/or factor IX. Factor VIIa is produced from its precursor, factor VII, which is synthesized in the liver and secreted into the blood where it circulates as a single chain glycopeptide. The cDNA sequence for factor VII has been characterized (Hagen et al., 1986, Proc. Natl. Acad. Sci. U.S.A., 83:2412–2416).

A variety of natural and synthetic inhibitors of TF/factor VIIa are known and have varying potency and selectivity. Tissue factor pathway inhibitor (TFPI; Broze, 1995, Thromb. Haemostas., 74:90) and nematode anticoagulant peptide c2 (NAPc2; Stanssens et al., 1996, Proc. Natl. Acad. Sci. U.S.A., 93:2149) bind factor Xa prior to the formation of a quaternary inhibitory complex with the TF/factor VIIa complex. Small protein direct inhibitors (Dennis et al, 1994, J. Biol. Chem., 35:22137) and inactive forms of TF/factor VIIa are also known (Kirchhofer et al, 1995, Arteriosclerosis, Thrombosis and Vascular Biol., 15:1098; Jang et al, 1995, Circulation, 92:3041). Additionally, synthetic peptides and soluble forms of mutant TF which retain binding affinity but have reduced cofactor activity have been prepared (Roenning et al, 1996, Thromb. Res., 82:73; Kelley et al, 1997, Blood, 89:3219). U.S. Pat. No. 5,679,639 describes polypeptides and antibodies which inhibit serine protease activity. U.S. Pat. No. 5,580,560 describes a mutant factor VIIa which has an improved half-life. U.S. Pat. No. 5,504,067 and U.S. Pat. No. 5,504,064 describe a truncated TF for the treatment of bleeding. Kunitz domain-tissue factor fusion proteins have also been shown to be bifunctional anticoagulants (Lee et al, 1997, Biochemistry, 36:5607–5611). The TF/factor VIIa complex has been indicated as an attractive target for the development of inhibitors based on a dissociation between surgical bleeding and prevention of intravascular thrombosis (Harker et al, 1995, Thromb. Haemostas., 74:464).

Compounds which block or inhibit enzymes in the coagulation cascade are therapeutically useful in treating or preventing thrombosis in a mammal suspected of having a condition characterized by abnormal thrombosis. For example, with respect to arterial vasculature, abnormal thrombus formation due to deterioration of an established atherosclerotic plaque is a major cause of acute myocardial infarction and unstable angina. Treatment of an occlusive coronary thrombus by thrombolytic therapy or percutaneous transluminal coronary angioplasty (PTCA) may be accompanied by reclosure of the vessel. In the venous vasculature, many patients undergoing surgery, particularly in the abdominal and lower body regions, experience thrombus formation which reduces blood flow and can lead to a pulmonary embolism. Disseminated intravascular coagulopathy in both the venous and arterial systems occurs commonly during septic shock, some viral infections, and cancer and may lead to rapid and widespread thrombus formation and organ failure.

PTCA and recanalization are favored procedures for treating occluded vessels. However, arterial thrombosis following these procedures remains a leading cause of failure. Heparin, the most widely used anticoagulant, has not been shown to be entirely effective in the treatment and prevention of acute arterial thrombosis or rethrombosis.

The synthesis and development of small molecule inhibitors based on the known three-dimensional structure of proteins is a challenge of modem drug development. Many thrombin inhibitors have been designed to have a hirudin-type structure. Stubbs and Bode, *Current Opinion in Structural Biology* 1994, 4:823–832. New synthetic thrombin inhibitors, as well as inhibitors of factor Xa and TF/factor VIIa, are reported. See, for example, *Annual Reports in Medicinal Chemistry*, 1995–1997, Academic Press, San Diego, Calif.

U.S. Pat. No. 5,589,173 describes the use of a tissue factor antagonist and a thrombolytic agent to treat myocardial infarction.

U.S. Pat. No. 5,399,487 describes naphthalenesulfonamides which are useful for determining proteolytic enzyme activity or as enzyme inhibitors.

A need continues to exist for compounds which are effective inhibitors of enzymes in the coagulation cascade and which exhibit improved inhibitory activity and/or selectivity towards selected enzymes in the cascade.

SUMMARY OF THE INVENTION

Accordingly, one object of the present invention is to provide novel compounds which inhibit factors/enzymes in the coagulation cascade and which are useful to prevent or treat thrombus formation in artertial or venous vessels. These compounds are useful as coagulation factor inhibitors and as anticoagulants in general.

In one embodiment, an object of the invention is to provide inhibitors which inhibit factor VIIa, TF/factor VIIa selectively relative to factor Xa, thrombin or kallikrein. The compounds of this embodiment preferaby inhibit TF/factor VIIa about one order of magnitude (10×), more preferably about two orders of magnitude(100×), even more preferably about three orders of magnitude (1000×), better than they inhibit factor Xa, thrombin and/or kallikrein.

In another embodiment, an object of the invention is to provide compounds which specifically inhibit factor Xa relative to the inhibition of factor VIIa, TF/factor VIIa, thrombin or kallikrein. The compounds of this embodiment preferaby inhibit factor Xa about one order of magnitude (10×), more preferably about two orders of magnitude (100×), even more preferably about three orders of magnitude (1000×), better than they inhibit TF/factor VIIa, thrombin and/or kallikrein.

In another embodiment, a specific object of the invention is to provide compounds which inhibit thrombin relative to inhibition of factor VIIa, TF/factor VIIa, Xa, or kallikrein. The compounds of this embodiment preferably inhibit factor thrombin about one order of magnitude (10×), more preferably about two orders of magnitude(100×), even more preferably about three orders of magnitude (1000×), better than they inhibit TF/factor VIIa, factor Xa and/or kallikrein.

A further object of the invention is to provide a method of inhibiting TF/factor VIIa, Xa or thrombin activity by contacting these enzymes with an effective inhibitory amount of the novel inhibitors of the present invention or a composition containing these compounds. A further object is to provide a method of treating a TF/factor VIIa, Xa or thrombin mediated disorder by administering to a mammal in need of such treatment an effective amount of one of the compounds of the invention or a composition containing the compound. An additional object is to provide a method of preventing thrombosis or treating abnormal thrombosis by administering to a mammal in need of such treatment an effective amount of one of the compounds of the invention or a composition containing the compound and a carrier or excipient.

These and other objects which will become apparent in the course of the following description have been achieved by the compounds of the present invention having the structure shown below:

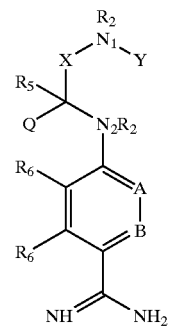

where
A and B are independently CH, $CR_3$ or N;
X is C=O or $(CR_{4a}R_{4b})_m$ where m=1 or 2;
Y is $S(O)_n$—$R_1$ where n=1 or 2, $S(O)_n$—$NR_2R_2$ where n=1 or 2, $S(O)_n$—$OR_2$ where n=1 or 2, $C(O)R_1$, $C(S)R_1$, $C(O)$—$OR_1$, $C(O)$—$NR_2R_2$;
$N_1$ and $N_2$ are nitrogen atoms;
Q and $R_1$ are independently
(1) optionally substituted alkyl having 1 to about 10 carbon atoms;
(2) optionally substituted aralkyl containing an aryl moiety having 6 to about 10 ring carbon atoms bonded to an alkyl moiety containing 1 to about 10 carbon atoms;
(3) optionally substituted heteroaralkyl containing a heteroaryl moiety having 5 to about 10 ring atoms bonded to an alkyl moiety having 1 to about 10 carbon atoms;
(4) optionally substituted carbocycloalkyl containing a carbocyclyl moiety having 3 to about 10 ring carbon atoms bonded to an alkyl moiety having 1 to about 10 carbon atoms;
(5) optionally substituted heterocycloalkyl containing a heterocyclyl moiety having 3 to about 10 ring atoms bonded to an alkyl moiety having 1 to about 10 carbon atoms;
(6) optionally substituted alkenyl having 2 to about 10 carbon atoms;
(7) optionally substituted aralkenyl containing an aryl moiety having 5 to about 10 ring atoms bonded to an alkenyl moiety having 2 to about 10 carbon atoms;
(8) optionally substituted heteroaralkenyl containing a heteroaryl moiety having 5 to about 10 ring atoms bonded to an alkenyl moiety having 2 to about 10 carbon atoms;
(9) optionally substituted carbocycloalkenyl containing a carbocyclyl moiety having 3 to about 10 ring carbon atoms bonded to an alkenyl moiety having 2 to about 10 carbon atoms;

(10) optionally substituted heterocycloalkyl containing a heterocyclyl moiety having 3 to about 10 ring atoms bonded to an alkenyl moiety having 2 to about 10 carbon atoms;

(11) optionally substituted aryl having 6 to about 10 ring carbon atoms;

(12) optionally substituted heteroaryl having 5 to about 10 ring atoms with ring atoms selected from carbon atoms and heteroatoms, where the heteroatoms are nitrogen, oxygen or sulfur;

(13) optionally substituted carbocyclyl having 3 to about 10 ring carbon atoms;

(14) optionally substituted heterocyclyl having 3 to about 10 ring atoms with ring atoms selected from carbon atoms and heteroatoms, where the heteroatoms are nitrogen, oxygen or sulfur;

each $R_2$ is, independently, H, alkyl, substituted alkyl, $C(O)R_7$ or $C(NH)R_7$, or $N_1R_2$ and $N_2R_2$ are together form the group $N_1$—CO—$N_2$;

$R_3$ is H, $C_1$–$C_6$ alkyl, $C_1$–$C_6$ alkoxy, halogen or OH;

$R_{4a}$ and $R_5$ are, independently, a member selected from the group consisting of H, unsubstituted or substituted alkyl, unsubstituted or substituted alkoxyalkyl, unsubstituted or substituted haloalkyl, unsubstituted or substituted aryl, alkyl-$OR_7$, alkyl-$NR_7R_8$, alkyl-$OC(O)R_7$, alkyl-$C(O)OR_7$, alkyl-$C(O)R_7OC(O)R_7$, $C(O)OR_7$, $C(O)R_7$ and members in which the alkyl, $R_7$ or $R_8$ is substituted with 1–3 F, Cl, Br I, $OR_7$, $SR_7$, $NR_7R_8$, $OC(OR_7)$, $C(O)OR_7$, $C(O)R_7$, $C(O)NR_7R_8$, $NHC(NH)NH_2$, $PO_3$, unsubstituted or substituted indolyl or unsubstituted or substituted imidazolyl groups;

$R_{4b}$ is H, alkyl, or substituted alkyl;

each $R_6$ is independently selected from the group selected from H, $C_1$–$C_6$ alkyl, $C_1$–$C_6$ alkyl-$OR_7$, $C_1$–$C_6$ alkyl-$NR_7R_8$, $C_1$–$C_6$ haloalkyl, halo, cyano, $OR_7$, $SR_7$, $NR_7R_8$, $C(O)OR_7$, $C(O)R_7$ and $OC(O)R_7$;

$R_7$ and $R_8$ are independently H or $C_1$–$C_6$ alkyl; and acid and base addition salts and prodrugs thereof.

Additionally, the objects of the invention are achieved by compositions containing these compounds and the methods described below.

DETAILED DESCRIPTION OF THE PREFERRED EMBODIMENTS

Definitions

The term "factor VIIa, TF/factor VIIa, factor Xa, thrombin or kallikrein mediated disorder" means a disease or physiological condition involving clotting of the blood and in which inhibition of one or more of these enzymes reduces or eliminates at least one of the physiological symptoms of the disease or condition.

The term "thrombosis" means the development of or formation of a blood clot or thrombus in a blood vessel of a mammal or in a synthetic vessel, such as a plastic or glass tube or vial. A thrombus which has detached from its original site and is found in another site is called a thrombotic embolus.

The term "abnormal thrombosis" means thrombosis occurring in a mammal which is contrary to the good health of the mammal.

The term "alkyl", used alone or as part of another term, means a branched or unbranched, saturated aliphatic hydrocarbon group, having the number of carbon atoms specified, or if no number is specified, having up to and including 12 carbon atoms. Examples of alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$–$C_6$ alkyl" and "alkyl of 1 to 6 carbon atoms" are synonymous and used interchangeably. Preferred "$C_1$–$C_6$ alkyl" groups are methyl, ethyl, 1-propyl, isopropyl, 1-butyl or sec-butyl.

The terms "substituted alkyl" or "substituted $C_n$–$C_m$ alkyl" where m and n are integers identifying the range of carbon atoms contained in the alkyl group, denotes the above alkyl groups that are substituted by one, two or three halogen (F, Cl, Br, I), trifluoromethyl, hydroxy, unsubstituted and substituted $C_1$–$C_7$ alkoxy, protected hydroxy, amino (including alkyl and dialkyl amino), protected amino, unsubstituted and substituted $C_1$–$C_7$ acyloxy, unsubstituted and substituted $C_3$–$C_7$ heterocyclyl, unsubstituted and substituted phenoxy, nitro, carboxy, protected carboxy, unsubstituted and substituted carboalkoxy, unsubstituted and substituted acyl, carbamoyl, carbamoyloxy, cyano, methylsulfonylamino, unsubstituted and substituted benzyloxy, unsubstituted and substituted $C_3$–$C_6$ carbocyclyl or $C_1$–$C_4$ alkoxy groups. The substituted alkyl groups may be substituted once (preferably), twice or three times with the same or with different substituents.

Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, trifluoroethyl, trifluoropropyl, carboxypropyl, 2-aminopropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocyclo group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. A preferred group of examples within the above group includes the substituted methyl group, e.g. a methyl group substituted by the same substituents as the "substituted $C_n$–$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

The term "alkoxy" denotes groups having the number of carbon atoms specified such as methoxy, ethoxy, n-propoxy, isopropoxy, n-butoxy, s-butoxy, t-butoxy and like groups. The term "substituted alkoxy" means these alkoxy groups substituted by the same substituents as the "substituted $C_n$–$C_m$ alkyl" group, for example, 2,2,2-trifluoroethoxy, 2,2,2-trifluoropropoxy, etc.

The term "acyloxy" denotes herein carboacyloxy groups having the specified number of carbon atoms such as formyloxy, acetoxy, propionyloxy, butyryloxy, pentanoyloxy, hexanoyloxy, heptanoyloxy, and the like. The term "substituted acyloxy" means these acyloxy groups substituted by the same substituents as the "substituted $C_n$–$C_m$ alkyl" group.

The term "alkylcarbonyl", "alkanoyl" and "acyl" are used interchangeably herein encompass groups having the specified number of carbon atoms such as formyl, acetyl, propionyl, butyryl, pentanoyl, hexanoyl, heptanoyl, benzoyl and the like.

The terms "carbocyclyl", "carbocyclylic" and "carbocyclo" alone and when used as a moiety in a complex group such as a carbocycloalkyl group, refers to a mono-, bi-, or tricyclic aliphatic ring having 3 to 14 carbon atoms and preferably 3 to 7 carbon atoms. Preferred carbocyclic groups include cyclopropyl, cyclobutyl, cyclopentyl and cyclohexyl groups. The terms "substituted carbocyclyl" and "carbocyclo" mean these groups substituted by the same substituents as the "substituted $C_n$–$C_m$ alkyl" group.

A "carbocycloalkyl" group is a carbocyclo group as defined above covalently bonded to an alkyl group as defined above.

The term "alkenyl" means a branched or unbranched hydrocarbon group having the number of carbon atoms designated containing one or more carbon-carbon double bonds, each double bond being independently cis, trans, or a nongeometric isomer. The term "substituted alkenyl" means these alkenyl groups substituted by the same substituents as the "substituted $C_n$–$C_m$ alkyl" group.

The term "alkynyl" means a branched or unbranched hydrocarbon group having the number of carbon atoms designated containing one or more carbon-carbon triple bonds. The term "substituted alkynyl" means these alkynyl groups substituted by the same substituents as the "substituted $C_n$–$C_m$ alkyl" group.

The terms "alkylthio" and "$C_1$–$C_{12}$ substituted alkylthio" denote $C_1$–$C_{12}$ alkyl and $C_1$–$C_{12}$ substituted alkyl groups, respectively, attached to a sulfur which is in turn the point of attachment for the alkylthio or substituted alkylthio group to the group or substituent designated.

The term "aryl" when used alone or as part of another term means a homocyclic aromatic group whether or not fused having the number of carbon atoms designated or if no number is designated, up to 14 carbon atoms. Preferred aryl groups include phenyl, naphthyl, biphenyl, phenanthrenyl, naphthacenyl, and the like (see e.g. *Lang's Handbook of Chemistry* (Dean, J. A., ed) $13^{th}$ ed. Table 7–2 [1985]).

The term "substituted phenyl" or "substituted aryl" denotes a phenyl group or aryl group substituted with one, two, three, four or five, preferably 1–2, 1–3 or 1–4 substituents chosen from halogen (F, Cl, Br, I), hydroxy, protected hydroxy, cyano, nitro, alkyl (preferably $C_1$–$C_6$ alkyl), alkoxy (preferably $C_1$–$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or methyne (CH) and/or methylene ($CH_2$) groups in these substituents may in turn be substituted with a similar group as those denoted above. Examples of the term "substituted phenyl" includes but is not limited to a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3,4-diethoxyphenyl, 3-ethoxy-4-isopropoxyphenyl, 3-ethoxy-s-butoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl) phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl) phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where 1, 2, or 3 of the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Preferred substituted phenyl groups include the 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Also, the term "substituted phenyl" represents phenyl groups having an aryl, phenyl or heteroaryl group fused thereto. The fused ring may also be substituted with any, preferably 1, 2 or 3, of the substituents identified above for "substituted alkyl" groups.

The term "aralkyl" means one, two, or three aryl groups having the number of carbon atoms designated, appended to an alkyl group having the number of carbon atoms designated including but not limited to; benzyl, napthylmethyl, phenethyl, benzhydryl(diphenylmethyl), trityl, and the like. A preferred arylalkyl group is the benzyl group.

The term "substituted aralkyl" denotes an alkyl group, preferably a $C_1$–$C_8$ alkyl group, substituted at any carbon with an aryl group, preferably a $C_6$–$C_{10}$ aryl group, bonded to the alkyl group through any aryl ring position and substituted on the alkyl portion with one, two or three groups chosen from halogen (F, Cl, Br, I), hydroxy, protected hydroxy, amino, protected amino, $C_1$–$C_7$ acyloxy, nitro, carboxy, protected carboxy, carbamoyl, carbamoyloxy, cyano, $C_1$–$C_6$ alkylthio, N-(methylsulfonylamino) or $C_1$–$C_4$ alkoxy. Optionally the aryl group may be substituted with one, two, three, four or five groups chosen from halogen, hydroxy, protected hydroxy, nitro, $C_1$–$C_6$ alkyl, $C_1$–$C_6$ alkoxy, carboxy, protected carboxy, carboxymethyl, protected carboxymethyl, hydroxymethyl, protected hydroxymethyl, aminomethyl, protected aminomethyl, or an N-(methylsulfonylamino) group. As before, when either the $C_1$–$C_8$ alkyl portion or the aryl portion or both are disubstituted, the substituents can be the same or different. This group may also appear as the substituted aralkyl moiety of a substituted aralkoxy group.

Examples of the term "substituted aralkyl" and this group when it occurs in a "substituted aralkoxy" group include groups such as 2-phenyl-1-chloroethyl, 1-phenyl-1-chloromethyl, 1-phenyl-1-bromomethyl, 2-(4-methoxyphenyl)ethyl, 2,6-dihydroxy-4-phenyl(n-hexyl), 5-cyano-3-methoxy-2-phenyl (n-pentyl), 3-(2,6-dimethylphenyl)n-propyl, 4-chloro-3-aminobenzyl, 6-(4-methoxyphenyl)-3-carboxy (n-hexyl), 5-(4-aminomethyl phenyl)-3-(aminomethyl)(n-pentyl), and the like.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as methyl, ethyl, isopropyl, t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl) methylsilyl)ethyl, p-toluenesulfonylethyl, 4-nitrobenzylsulfonylethyl, allyl, cinnamyl, 1-(trimethylsilylmethyl) prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Preferred carboxylic acid protecting groups are the allyl and p-nitrobenzyl groups. Similar carboxy-protecting groups used in the cephalosporin, penicillin and peptide arts can also be used to protect a carboxy group substituents. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

As used herein the term "amide-protecting group" refers to any group typically used in the peptide art for protecting the peptide nitrogens from undesirable side reactions. Such groups include p-methoxyphenyl, 3,4-dimethoxybenzyl, benzyl, O-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Further descriptions of these protecting groups can be found in "Protective Groups in Organic Synthesis", by Theodora W. Greene, 1981, John Wiley and Sons, New York.

The terms "heterocyclic group", "heterocyclic", "heterocyclyl", or "heterocyclo" alone and when used as a moiety in a complex group such as a heterocycloalkyl group, are used interchangeably and refer to any mono-, bi-, or tricyclic saturated or non-aromatically unsaturated ring having the number of atoms designated, generally from 3 to about 10 ring atoms, where the ring atoms are carbon and 1,2,3 or 4 nitrogen, sulfur or oxygen atoms. Typically, a 5-membered ring has 0 to 2 double bonds and 6- or 7-membered ring has 0 to 3 double bonds and the nitrogen or sulfur heteroatoms may optionally be oxidized, and any nitrogen heteroatom may optionally be quaternized. Examples include pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperidinyl, and 3,4,5,6-tetrahydropiperidinyl.

A "heterocycloalkyl" or a "heterocycloalkenyl" group is a heterocyclo group as defined above covalently bonded to an alkyl or alkenyl group as defined above.

Unless otherwise specified, "heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and preferably at least one heteroatom is nitrogen (*Lang's Handbook of Chemistry, supra*). Included in the definition are any bicyclic groups where any of the above heteroaryl rings are fused to a benzene ring. Heteroaryls in which nitrogen or oxygen is the heteroatom are preferred.

The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl.

Heterocyclic 5-membered ring systems containing a sulfur or oxygen atom and one to three nitrogen atoms are also suitable for use in the instant invention. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl. A preferred group of examples of benzo-fused derivatives are benzoxazol-2-yl, benzthiazol-2-yl and benzimidazol-2-yl.

Further suitable specific examples of the above heterocylic ring systems are 6-membered ring systems containing one to three nitrogen atoms. Such examples include pyridyl, such as pyrid-2-yl, pyrid-3-yl, and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a preferred group.

The substituents for the optionally substituted heterocyclic ring systems, and further examples of the 5- and 6-membered ring systems discussed above can be found in W. Druckheimer et al., U.S. Pat. No. 4,278,793.

A particularly preferred group of "heteroaryl" include; 1,3-thiazol-2-yl, 4-(carboxymethyl)-5-methyl-1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl.

An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

A "heteroaralkyl" or a "heteroaralkenyl" group is a heteroaryl group as defined above covalently bonded to an alkyl group or to an alkenyl group as defined above.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

The term "prodrug" as used herein means a derivative of a parent drug molecule that enhances pharmaceutically desirable characteristics or properties (e.g. transport, bioavailablity, pharmacodynamics, etc.) and that requires biotransformation, either spontaneous or enzymatic, within the organism to release the active parent drug.

Embodiments

The invention is generally directed to compounds having the structure shown below.

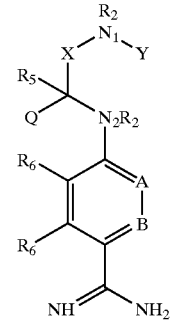

In this structure $R_2$, $R_5$, $R_6$, A, B, N1, N2, Q, X, and Y have the meanings described above. In these meanings, alkyl is preferably unsubstituted or substituted $C_1$–$C_6$ alkyl; alkenyl is preferably unsubstituted or substituted $C_2$–$C_6$ alkenyl; alkynyl is preferably unsubstituted or substituted $C_2$–$C_6$ alkynyl; aryl is preferably unsubstituted or substituted naphthyl or phenyl, more preferably phenyl, aralkyl is preferably unsubstituted or substituted benzyl. The variable m is preferably 1.

The group Y is preferably $S(O)_n$—$R_1$ where n=1 or 2 or the group $S(O)_n$—$NR_2R_2$ where n=1 or 2, more preferably $S(O)_n$—$R_1$.

In one preferred embodiment, $R_1$, for example when Y is $S(O)_n$—$R_1$, is selected from the group consisting of $C_1$–$C_6$ alkyl, $C_2$–$C_6$ alkenyl, $C_2$–$C_6$ alkynyl, $C_3$–$C_6$ cycloalkyl, phenyl, naphthyl, benzyl and heteroaryl having 5–6 ring atoms selected from carbon atoms and 1–2 heteroatoms, where the heteroatoms are N, S, or O, and $R_1$ optionally substituted with 1–3 substituents selected from the group consisting of halo, nitro, $C_1$–$C_6$ alkyl, $NR_7R_8$, $OR_7$, $SR_7$, $C_1$–$C_6$ alkyl-C(O)$OR_7$, $C_1$–$_6$ alkyl-OC(O)$R_7$, $C_1$–$C_6$ alkyl-C(O)$R_7$, $C_1$–$C_6$ alkyl-$OR_7$, $C_1$–$C_6$ haloalkyl, $C_1$–$C_6$ alkyl-$NR_7R_8$, C(O)$OR_7$, OC(O)$R_7$, C(O)$NR_7R_8$, OC(O)$NR_7R_8$, NHC(O)$R_7$, and NHC(O)$NR_7R_8$, where $R_7$ and $R_8$ independently are H or $C_1$–$C_6$ alkyl. In this embodiment, each of the remaining variables $R_2$, $R_5$, $R_6$, A, B, Q, X, and Y may be independently selected to be any of the groups in the respective definitions described above.

In a second preferred embodiment, Q is phenyl optionally substituted with 1–5, preferably 2–4, more preferably 2–3, substituents selected from the group consisting of halo, nitro, $C_1$–$C_6$ alkyl, $C_2$–$C_6$ alkenyl, $C_2$–$C_6$ alkynyl, $NR_7R_8$, $OR_7$, $SR_7$, $C_1$–$C_6$ alkyl-C(O)$OR_7$, $OC_1$–$C_6$ alkyl-C(O)$OR_7$, $C_1$–$C_6$ alkyl-$OR_7$, $OC_1$–$C_6$ alkyl-$OR_7$, $C_1$–$C_6$ alkyl-$NR_7R_8$, $OC_1$–$C_6$ alkyl-$NR_7R_8$, $C_1$–$C_6$ alkyl-C(O)$NR_7R_8$, $OC_1$–$C_6$ alkyl-C(O)$NR_7R_8$, $C_1$–$C_6$ alkyl-C(O)$R_7$, $OC_1$–$C_6$ alkyl-C(O)$R_7$, $C_1$–$C_6$ haloalkyl, O-aralkyl (e.g. benzyloxy), C(O)$OR_7$, C(O)$NR_7R_8$, OC(O)$NR_7R_8$, NHC(O)$R_7$, NHC(O)$NR_7R_8$, $NR_7S(O)_nR_1$, $NR_7S(O)_nR_7$, $S(O)_nR_7$, $S(O)_nNR_7$, where $R_7$ and $R_8$ independently are H or $C_1$–$C_6$ alkyl. In this embodiment, each of the remaining variables $R_2$, $R_5$, $R_6$, A, B, X, and Y (and $R_1$) may be independently selected to have any of the definitions described above. Each alkyl, alkenyl and alkynyl moiety may also be substituted as defined above.

In a third preferred embodiment, Q has the structure

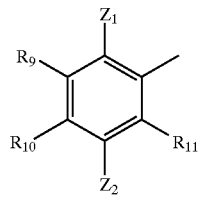

where $R_9$ is H, $C_1$–$C_6$ alkyl, $C_2$–$C_6$ alkenyl, $C_2$–$C_6$ alkynyl, $C_1$–$C_6$ alkoxy, hydroxy, $NR_7R_8$, $SR_7$ or $OR_7$, where $R_7$ and $R_8$, independently, are H or unsubstituted or substituted $C_1$–$C_6$ alkyl;

$R_{10}$, $R_{11}$ and $Z_2$, independently, are each selected from the group consisting of H, halo, nitro, cyano, $C_1$–$C_6$ alkyl, $C_6$–$C_{10}$ aryl, $NR_7R_8$, $OR_7$, $SR_7$, $C_1$–$C_6$ alkyl-C(O)$R_7$, $C_1$–$C_6$ alkyl-C(O)$NR_7R_8$, $C_1$–$C_6$ alkyl-C(O)$OR_7$, $C_1$–$C_6$ alkyl-OC(O)$R_7$, $C_1$–$C_6$ alkyl-$OR_7$, $OC_1$–$C_6$ alkyl-C(O)$R_7$, $OC_1$–$C_6$ alkyl-C(O)$OR_7$, $OC_1$–$C_6$ alkyl-OC(O)$R_7$, O—$C_1$–$C_6$ alkyl-$OR_7$, $OC_1$–$C_6$ alkyl-C(O)$NR_7R_8$, $C_1$–$C_6$ haloalkyl, $OR_{12}$, $C_1$–$C_6$ alkyl-$R_{12}$, O—$C_1$–$C_6$ alkyl-$R_{12}$, C(O)$OR_7$, C(O)$OR_{12}$, C(O)$NR_7R_8$, OC(O)$NR_7R_8$, $NR_7C(O)R_7$, $NR_7C(O)R_{12}$, $NR_7C(O)$—$NR_7R_8$, $NR_7C(O)OR_7$, $NR_7C(O)OR_{12}$, $NR_7S(O)_n$—$R_1$, $NR_7S(O)_n$—$R_7$ and $NR_7S(O)_n$—$R_{12}$, where $R_7$ and $R_8$, independently, are H or unsubstituted or substituted $C_1$–$C_6$ alkyl, $R_{12}$ is unsubstituted or substituted $C_6$–$C_{10}$ aryl or heterocycl as defined above and n is 1 or 2;

$Z_1$ is H, $C_1$–$C_6$ alkyl, $C_1$–$C_6$ alkoxy, halogen or nitro. In this embodiment, each of the remaining variables $R_2$, $R_5$, $R_6$, A, B, X, and Y may be independently selected to have any of the definitions described above. Each alkyl, alkenyl and alkynyl moiety may also be substituted as defined above.

In various aspects of the invention, $Z_1$ and $Z_2$ may be hydrogen; $Z_1$, $Z_2$ and $R_{11}$ may be hydrogen; or $Z_1$, $R_{10}$ and $R_{11}$ may be hydrogen; and the remaining ring substituents are as defined above.

In another embodiment, the substituents at the 4- and 5-positions or at the 5- and 6-positions of the ring when Q is substituted phenyl may be bonded together to form an unsubstituted or substituted carbocyclic or hetercyclic ring. Examples of such compounds are shown below, where the symbol

is preferably a 5-membered or a 6-membered carbocyclic or heterocyclic ring which is fused to the phenyl ring in the positions shown below

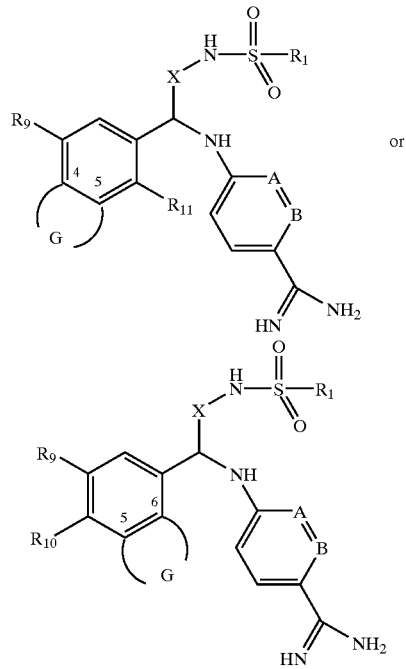

Examples of suitable 5-membered or a 6-membered carbocyclic or heterocyclic rings which may be fused to the phenyl ring include the ring systens shown below, where $R_6$ is as defined above.

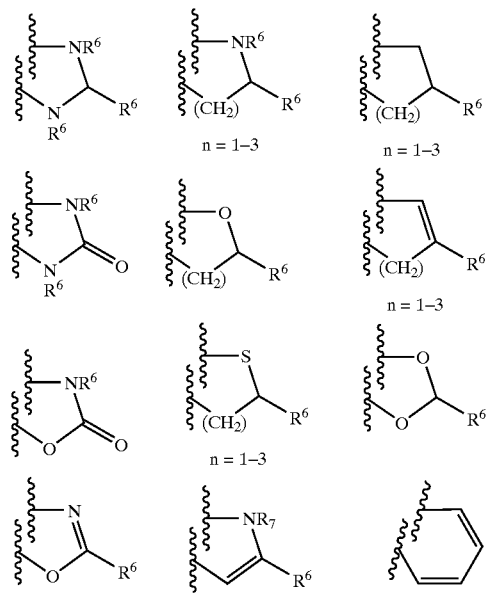

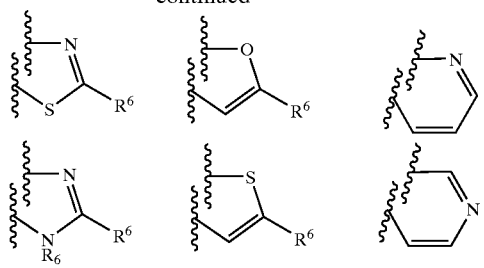

In another preferred embodiment, Y is $S(O)_n$—$R_1$ where n is 1 or 2, preferably 2 In this embodiment, $R_1$ may be as defined above and each of the remaining variables may be independently selected to have any of the definitions described above.

Compounds in which Q is substituted phenyl and $R_{10}$ is selected from the group consisting of $C_1$-$C_6$ alkyl, $C_1$-$C_6$ alkoxy, $C_1$-$C_6$ aminoalkyl, $C_1$-$C_6$ haloalkyl, $C_1$-$C_6$ hydroxyalkyl, phenyl, phenoxy, benzyl, benzyloxy, as well as phenoxy- and benzyloxy-substituted with $C_1$-$C_6$ alkyl, $C_1$-$C_6$ alkoxy, halo, $C_1$-$C_6$ haloalkyl, $C_1$-$C_6$ hydroxyalkyl, $C_1$-$C_6$ aminoalkyl, OC(O)—$C_1$-$C_6$ alkyl C(O)O—$C_1$-$C_6$ alkyl and C(O)OH are also preferred, where each of the remaining variables may be independently selected to have any of the definitions described above.

Also of interest are compounds in which $R_{11}$ is $NR_7C_1$-$C_6$ alkyl-C(O)$NR_7R_8$, $NR_7S(O)_n$—$R_7$ or $NR_7S(O)_n$—$R_{12}$, n is 1 or 2 and/or where $Z_1$=$Z_2$=H and/or where $R_{10}$ is $OR_7$, $OR_{12}$, $OC_7$-$C_{10}$-aralkyl, $OC_1$-$C_6$ alkyl-$OR_7$ or $OC_1$-$C_6$ alkyl-$OR_{12}$ where $R_7$ and $R_{12}$ are unsubstituted or substituted as defined above. Suitable substituted $R_7$ and $R_{12}$ include these groups substituted as described above, for example, having 1 or 2 $C_1$-$C_6$ alkoxy, $C_1$-$C_6$ alkoxy-$C_1$-$C_6$ alkoxy, halo, $C_1$-$C_6$ haloalkyl, $C_1$-$C_6$ hydroxyalkyl, $C_1$-$C_6$ aminoalkyl, OC(O)—$C_1$-$C_6$ alkyl, C(O)O—$C_1$-$C_6$ alkyl, $C_1$-$C_6$ alkyl C(O)$OR_7$, $C_1$-$C_6$ alkyl OC(O)$R_7$ or C(O)OH. In these compounds, each of the remaining variables may be independently selected to have any of the definitions described above. These compounds are also interesting where, Y is $S(O)_n$—$R_1$ where n is 1 or 2, that is, disulfonamide comounds.

In another embodiment, A and B are independently CH or $CR_3$, where $R_3$ is H, $C_{1-6}$ alkyl or OH, where the remaining variables may be independently selected to have any of the definitions described above.

In another embodiment, $R_6$ is H or $R_3$ is CH, where the remaining variables may be independently selected to have any of the definitions described above.

In another preferred embodiment, X is a carbonyl group (C=O), where the remaining variables may be independently selected to have any of the definitions described above. In this embodiment, preferably m=1.

Table 1, setting forth examples of some preferred groups at various positions of some compounds of the invention, is shown below. A group of specific compounds is disclosed in this table and is obtained by selecting all unique combinations of substituents, one from each column of the table, for each variable and combining these groups with the structure disclosed above Table 1.

TABLE 1

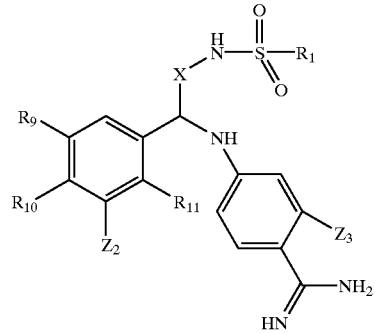

| X | R9 | R10 | Z2 | R11 | R1 | Z3 |
|---|----|-----|----|----|----|----|
| CH2 | OEt | OEt | H | H | Me | H |
| C=O | OMe | OH | OEt | NMeSO2Me | Et | OH |
| | CH2CH3 | OMe | OMe | Ph | Pr | Cl |
| | CH=CH2 | OiPr | Ph | Naphthyl | Bu | F |
| | CCH | OCH2Ph | OiPr | | iPr | |
| | CH2CCH | CH(CH3)Ph | OPr | NHSO2Me | iBu | |
| | H | CH(CH2Cl)Ph | CH(CH2Cl)Ph | NPrSO2Me | sBu | |
| | Pr | OCH2CH2CF3 | OCH2CH2CF3 | N(CH2CO2H)SO2Me | Ph | |
| | Cl | OCH2CF3 | OCH2CF3 | NMeSO2CH2CO2H | O-tolyl | |
| | SCH3 | CH(CO2H)Ph | CH(CO2H)Ph | NHSO2CH2CO2H | CH2CH2CO2H | |
| | SCH2CH3 | CH(CO2Me)Ph | CH(CO2Me)Ph | NHCOCH3 | CH2CH2CONH2 | |
| | NHCH3 | Ph | Ph | NHCOCH2CO2H | CH2CH2CO2Me | |
| | NHCH2CH3 | OPh | OPh | NHSO2-thiophene | p-tolyl | |
| | | H | Cl | NHSO2CH2CO2H | 4-chlorophenyl | |
| | | Cl | Br | NHSO2CH2CO2Me | 4-aminomethylphenyl | |
| | | Br | F | OCH2CO2H | 4-aminophenyl | |
| | | F | OCH2Ph | pyridyl | 2-chlorophenyl | |

TABLE 1-continued

[Structure shown with substituents X, R9, R10, R11, Z2, Z3, R1, and sulfonamide/amidino groups]

| X | R9 | R10 | Z2 | R11 | R1 | Z3 |
|---|----|-----|----|-----|-----|-----|
|   | H  | NHCH2CH3 | NCH2CH3<br>SCH3 |   | 3-nitrophenyl<br>1-naphthyl<br>2-thiophene<br>3-thiophene<br>2-furan<br>3-furan<br>CH2CH(NH2)CH3<br>pyridyl<br>2-naphthyl |   |

Methods of Making

Compounds of the present invention can be prepared by methods employing standard chemical methodologies described and referenced in standard textbooks (e.g. March, J. "Advanced Organic Chemistry" McGraw-Hill, New York, 1977; Colliman, J. P., Hegedus, L. S., Norton, J. R., Finke, R. G. "Principles and Applications of Organotransition Metal Chemistry" University Science, Mill Valley, 1987; Larock, R. C. "Comprehensive Organic Transformations" Verlag, New York, 1989).

A key intermediate in the synthesis of compounds of the invention has the formula shown below

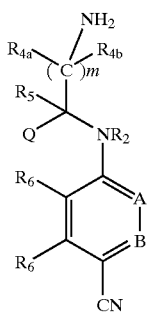

In this formula, A, B, $R_2$, $R_{4a}$, $R_{4b}$, $R_5$, $R_6$, m and Q have the meanings and preferred meanings described above. This compound can be prepared using several alternative synthetic routes. After preparation, the cyano group may be converted into an amidino group ($C(NH)NH_2$), for example, using known procedures, such as the Pinner reaction. A cyano compound having the formula shown above may be reacted with hydroxyl amine, preferably in an alcohol solvent, followed by reduction with Raney Ni, preferably in an alcohol solvent, or may be reacted first with ethanolic HCl and then with alcoholic ammonia to yield the corresponding amidino compounds. Alternatively, a modified Pinner reaction using pyridine/diethylamine (1/1)/hydrogen sulfide followed by methyl iodide/acetonitrile and then ammonium acetate/ethanol will provide the desired amidino product.

One synthetic route to compounds having the formula shown above is a condensation reaction using appropriately substituted precursors as shown in the scheme below.

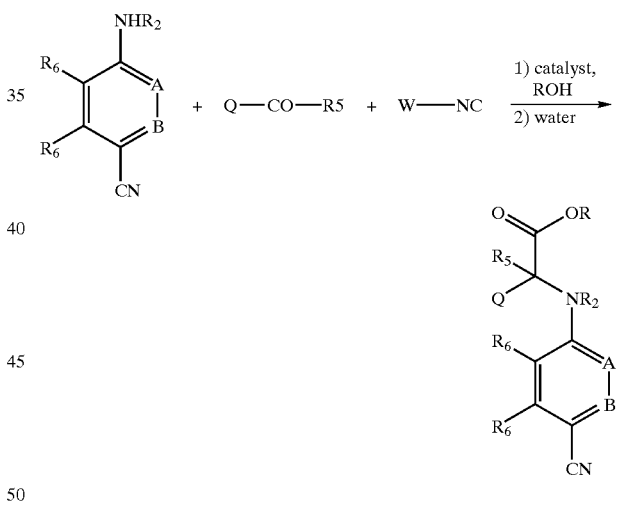

This condensation is performed in the presence of a catalyst, preferably a Lewis acid catalyst, and an alkyl alcohol (ROH), preferably a lower alkyl alcohol such as methanol, ethanol, i-propanol, etc., followed by hydrolysis of the intermediate, preferably with an excess of water, generally up to about 10 equivalents of water. Suitable Lewis Acids include $BF_3$ etherate, $AlCl_3$, etc. W—NC is an isonitrile in which W may be any suitable hydrocarbon group, generally an alkyl, carbocycloalkyl, or aralkyl group, preferably having no more than about 12 carbon atoms. A particularly preferred isonitrile is benzyl isonitrile. The ester product may be purified by standard techniques, including high pressure liquid chromatography (HPLC), column chromatography, recrystallization, etc.

Reduction of the resulting ester to an alcohol can be accomplished using any known reducing agent ([H]) which will preferentially reduce an ester before a nitrile. Suitable reducing agents and procedures are well known in the art. See, for example, *Modern Synthetic Reactions*, H. O. House, W. A. Benjarni, Inc., Second Ed., 1972. A useful reducing agent is lithium borohydride. The alcohol may then be converted to an amine using known chemical reactions. Suitable conditions include first reacting the alcohol with hydrogen azide, DEAD, and triphenyl phosphine ($PPh_3$), following by $PPh_3$ and water or first with phthalimide, DEAD and $PPh_3$, followed by hydrazine. These reactions are shown in the scheme below. Alternatively, the ester may be reacted with a reagent having a nucleophilic carbon atom to introduce suitable $R_{4a}$ groups. Such reagents may include an activated methylene carbon, for example a methylene which is adjacent to one or more strong electron withdrawing groups such as nitro ($NO_2$), carboalkoxy ($COOR_{4a}$), etc., Grignard reagents ($R_{4a}MgHal$, where Hal is a halogen), etc. and then converted to the alcohol and to the amine.

amidine may be performed in any desired order. A preferred reaction scheme is shown in the scheme below.

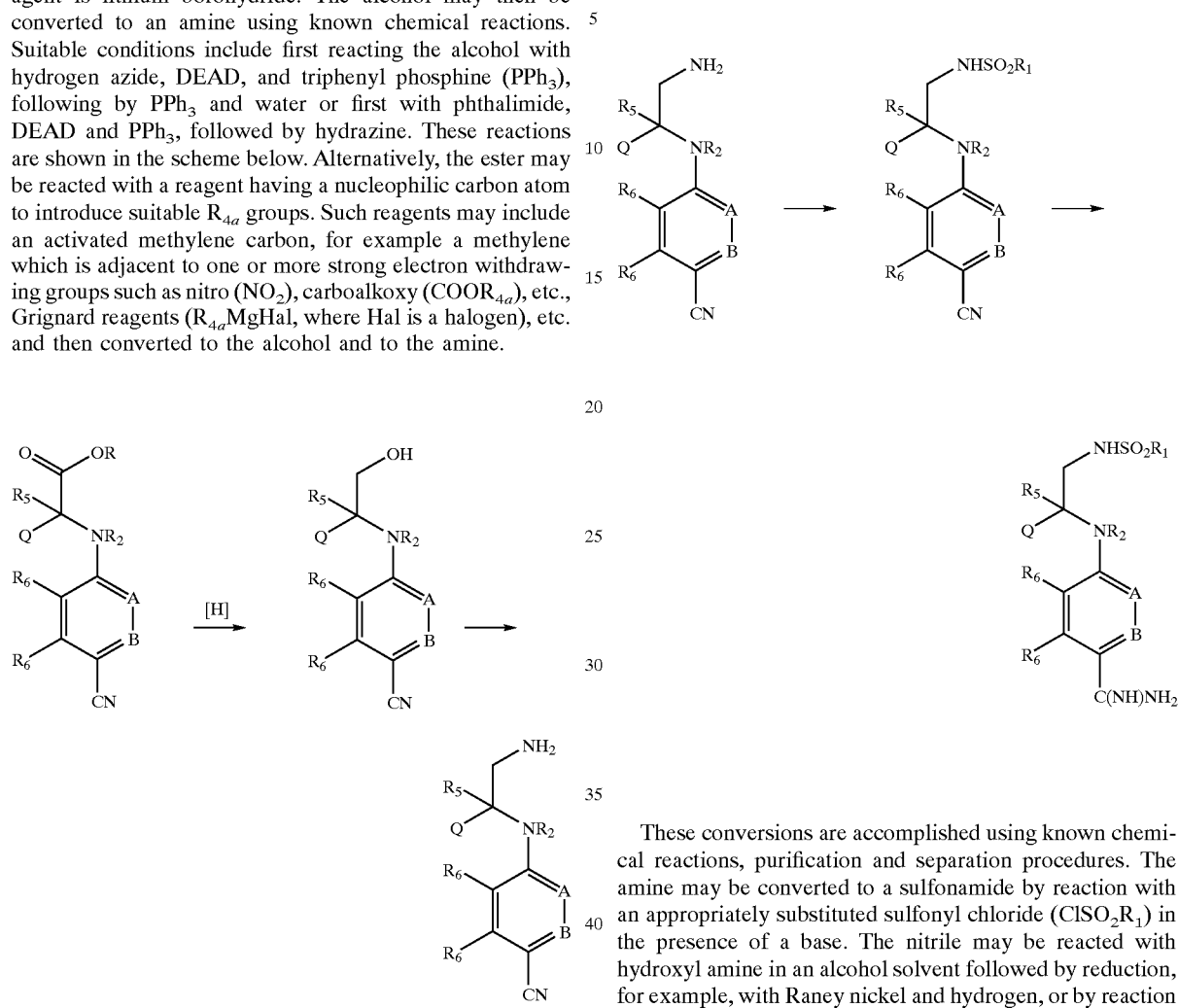

Conversion of the amine functional group to a sulfonamide and the conversion of the nitrile functional group to an These conversions are accomplished using known chemical reactions, purification and separation procedures. The amine may be converted to a sulfonamide by reaction with an appropriately substituted sulfonyl chloride ($ClSO_2R_1$) in the presence of a base. The nitrile may be reacted with hydroxyl amine in an alcohol solvent followed by reduction, for example, with Raney nickel and hydrogen, or by reaction with HCl/alcohol and then ammonia/alcohol.

An example of a suitable reaction sequence is shown below.

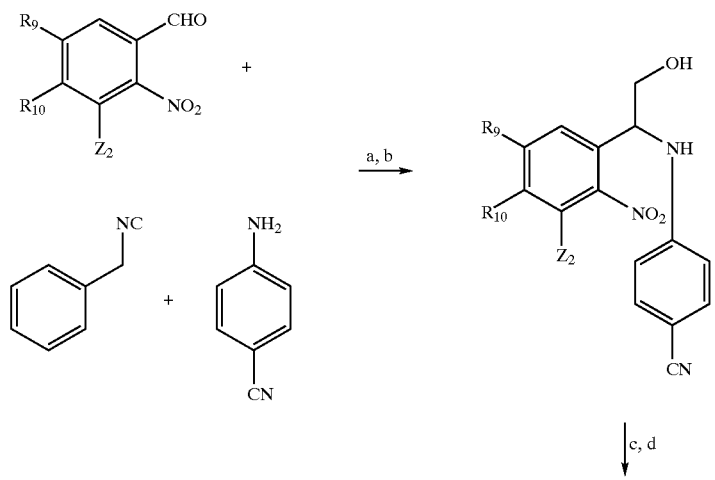

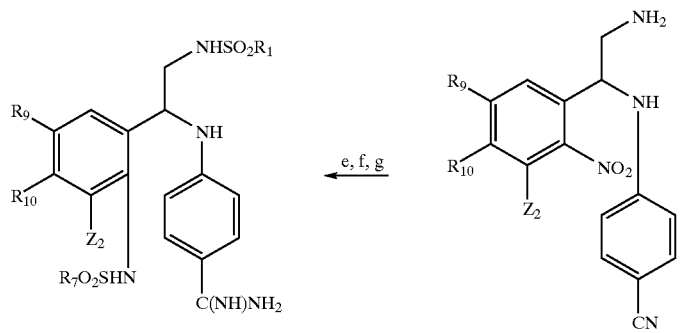

In this sequence, a=BF$_3$OEt$_2$/EtOH, b=LiBH$_4$/DME, c=phthalimide,DIAD/PPh$_3$/THF, d=H$_2$NNH$_2$/EtOH, e=R$_1$SO$_2$Cl, f=H$_2$/Pt/C/EtOH, and g=R$_7$SO$_2$Cl/NEt$_3$, NH$_2$OH—HCl/NEt$_3$, H$_2$/Ra-Ni/MeOH.

An analogous related synthetic scheme may be used to prepare the corresponding compounds in which X is a carbonyl as shown below.

Compounds in which m=2 can be prepared using according to the scheme shown below which provides an alcohol which is homologous to the alcohol shown in the scheme above and which can be converted to an amine (and further elaborated compounds) in an analogous manner. In the scheme below, (a) is a base and (b) is a reducing agent such as LiBH$_4$

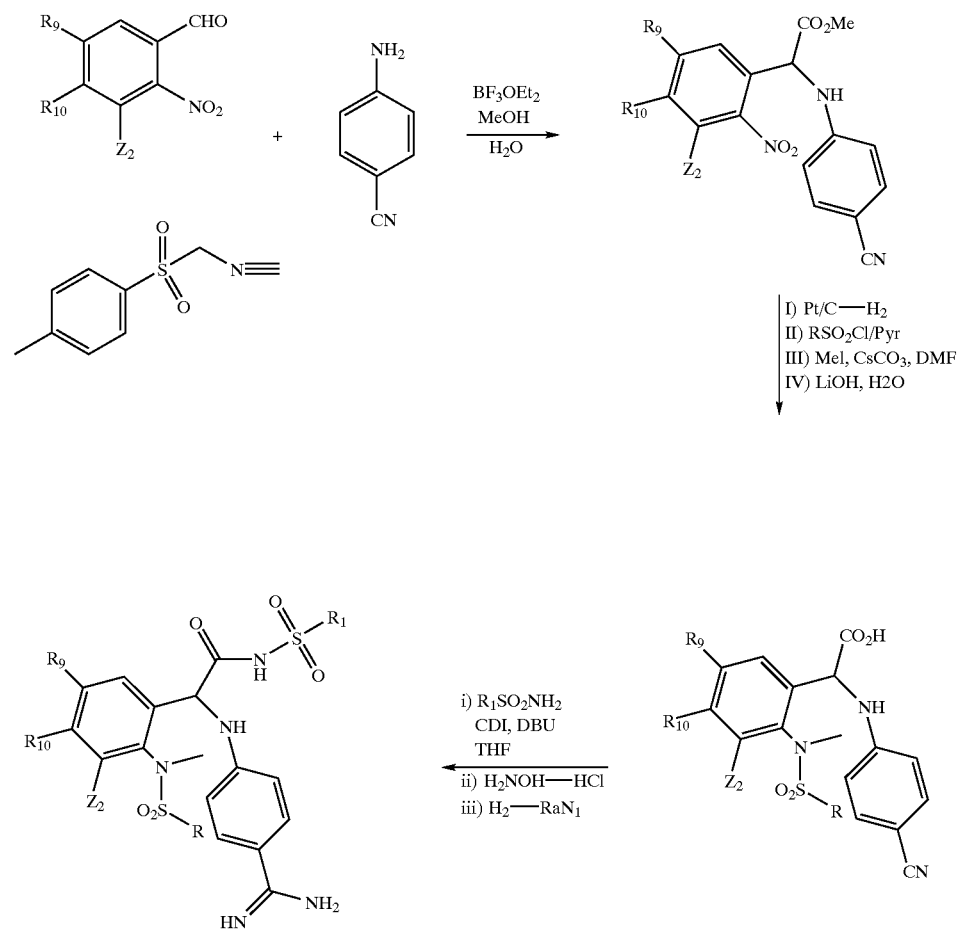

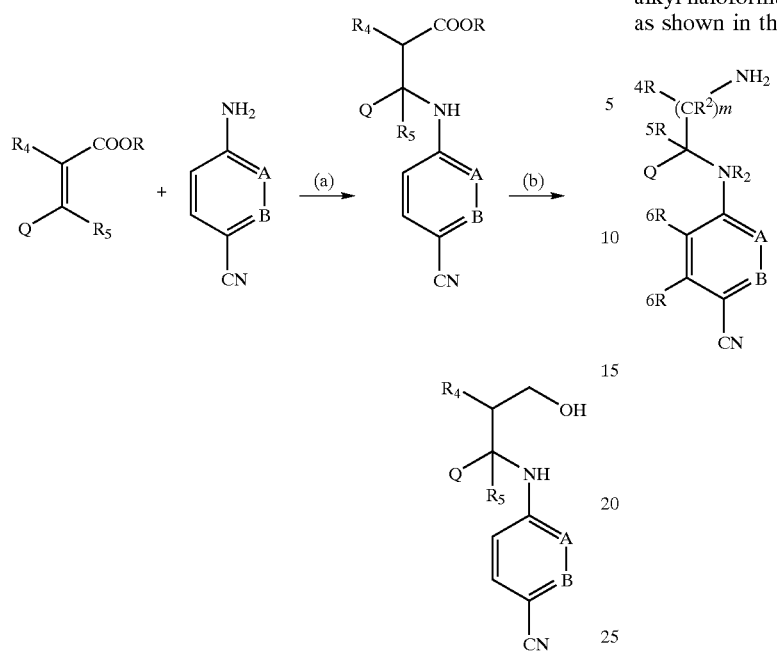
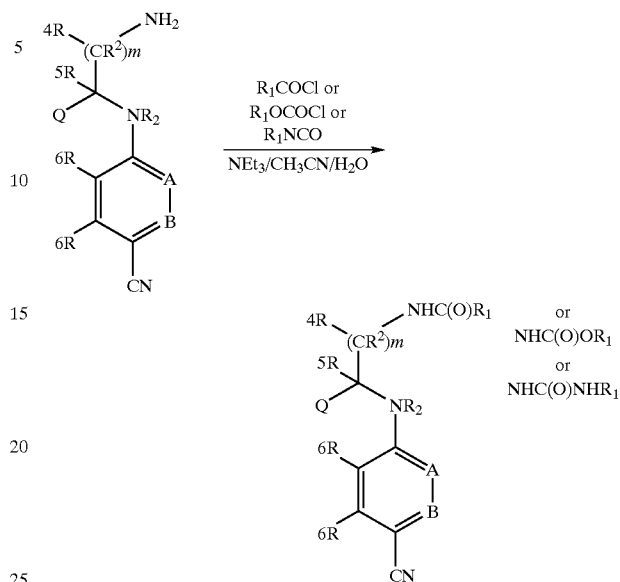
Compounds in which Y is C(O)—R¹; C(O)—OR¹; C(O)—NR¹R² are prepared as described above using the corresponding acyl halide (preferably an acyl chloride), alkyl haloformate (preferably a chloroformate) or isocyanate as shown in the scheme below:
An example of a suitable reaction sequence is shown below.
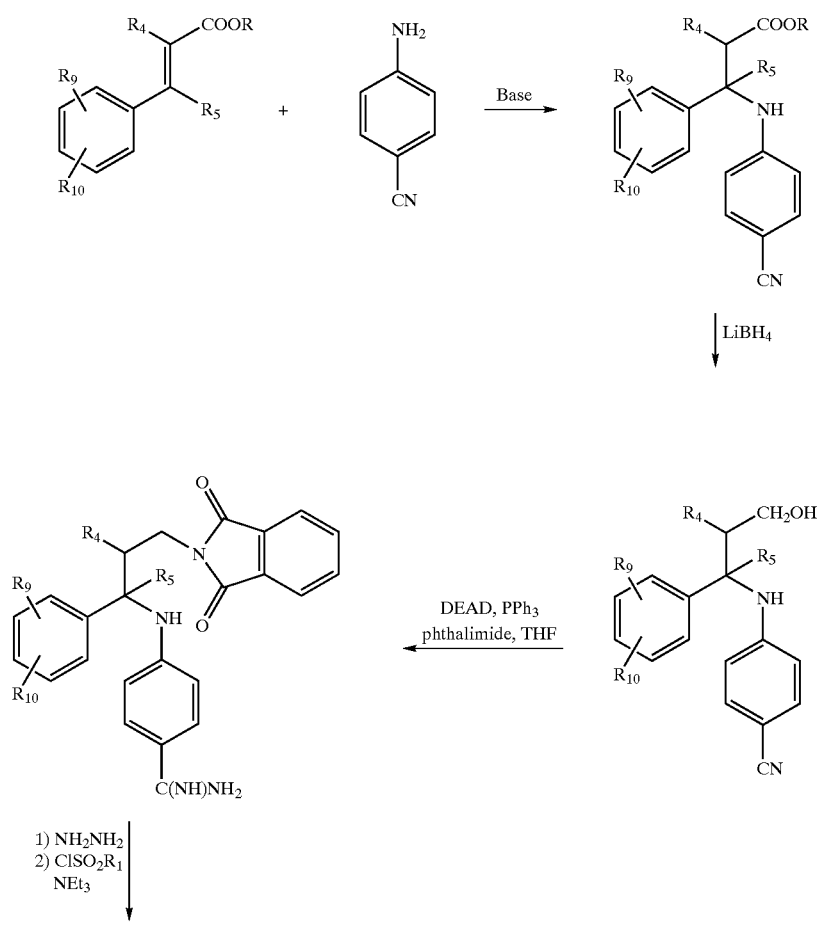

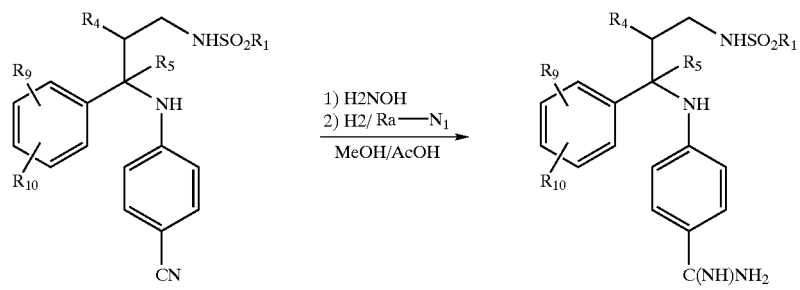

The esters resulting from the condensation reactions shown above can also function as intermediates in the synthesis of compounds in which X is a carbonyl group. Conversion of the ester to a carboxylic acid is easily performed by saponification with an alkali-metal hydroxide such as lithium, sodium, or potassium hydroxide. Coupling of a sulfonamide to the acid is accomplished by first activating the carboxylate for coupling using, for example, carbonyl diimidazole or other routine activating agents used in peptide synthesis. The second part of the coupling is done by mixing an alkyl or aryl sulfonamide with a strong base such as DBU or sodium hydride, preferably in an anhydrous solvent, such as a hydrocarbon or ether solvent, e.g. tetrahydrofuran. The nitrile is converted to an amidine by methods already described.

In a more preferred variation of this embodiment, Q is a substituted phenyl having substituents $Z_1$, $Z_2$, and $R_9$–$R_{11}$ as described below.

A further method of preparing intermediate compounds useful in preparing the compounds of the invention is shown below and involves the synthesis of imine compounds from readily available aldehydes and ketones followed by nucleophilic addition of a nucleophilic carbon atom containing reagent, i c in general "Nu". "Nu" may be a moiety such as $CHR_{4a}NO_2$, $CHR_{4a}COOR$, $CH(NO_2)(COOR)$, etc., which are generated using well known Grignard reactions, reactions in which a base is used to remove a proton from the carbon atom adjacent to an electron withdrawing group (CO, COO, $NO_2$), etc.

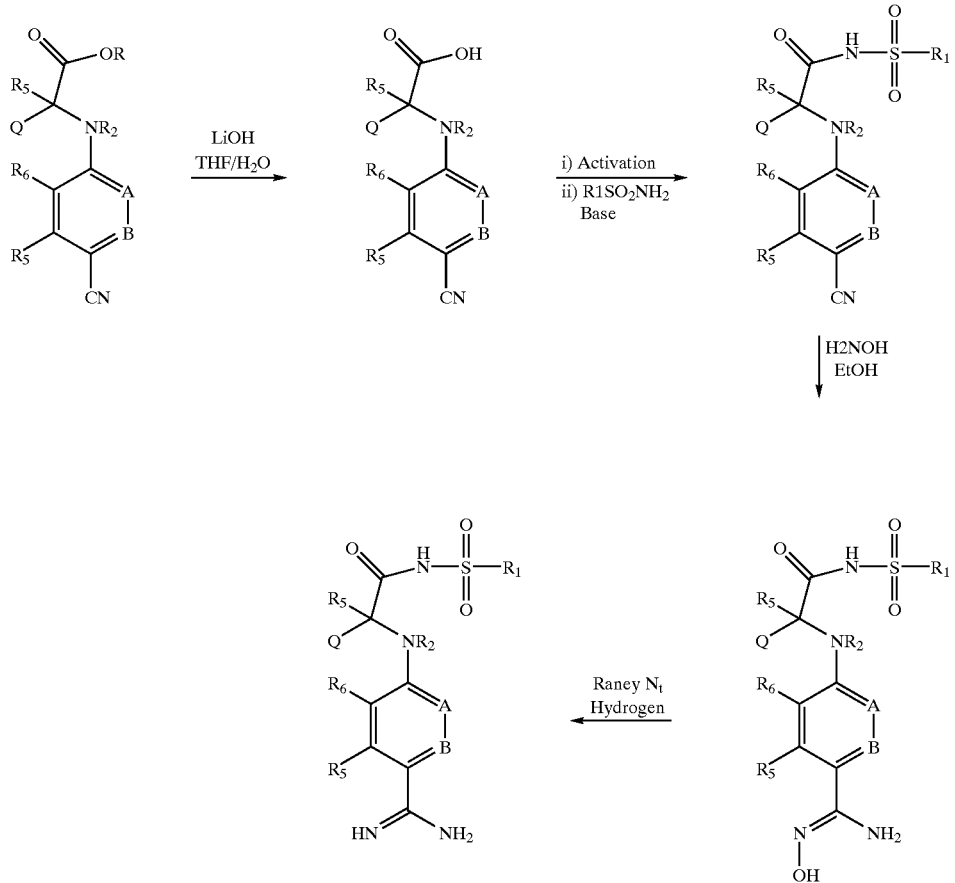

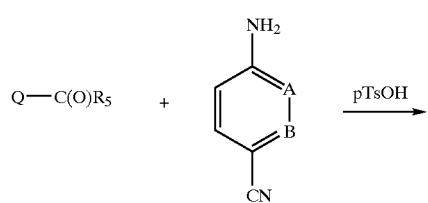

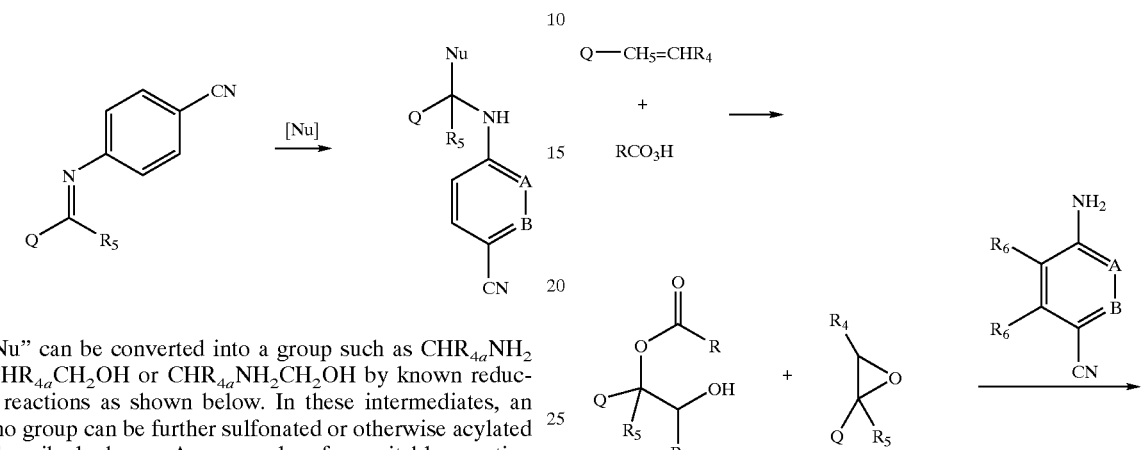

An alternative synthetic procedure can be used to prepare the alcohol intermediates described above. As shown in the scheme below, reaction of an initial styrene derivative with a peracid usually produces a mixture of products containing non-hydrogen $R_{4a}$ and/or $R_5$ substituents as shown below which can be converted without separation to the alcohol by reaction with a cyano-aniline or corresponding cyano-pyridine.

"Nu" can be converted into a group such as $CHR_{4a}NH_2$ or $CHR_{4a}CH_2OH$ or $CHR_{4a}NH_2CH_2OH$ by known reduction reactions as shown below. In these intermediates, an amino group can be further sulfonated or otherwise acylated as described above. An example of a suitable reaction sequence is shown below.

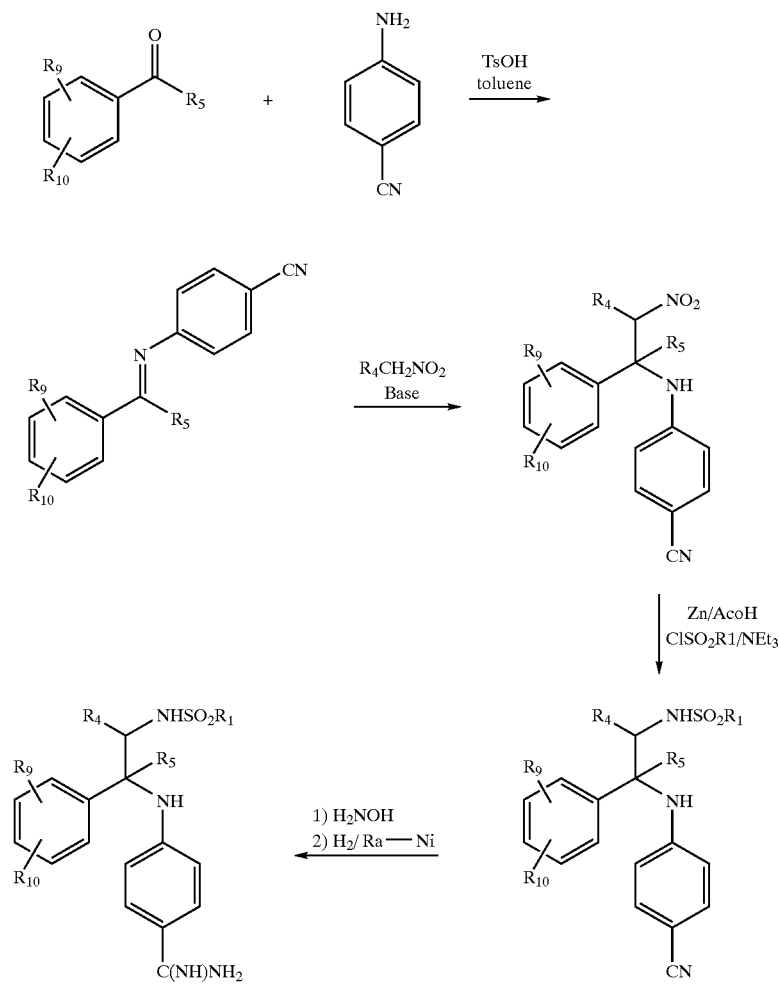

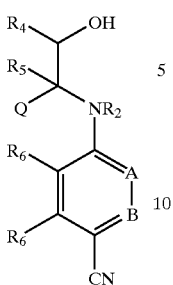

The alcohol can then be used to prepare compounds of the invention as described above.

When the corresponding compounds in which A and B are nitrogen are desired, the aniline or substituted aniline used in the reactions described above is replaced with the corresponding amino-pyridine or substituted amino-pyridine compounds.

Compounds in which the sulfonamide nitrogen bears a substituent can be prepared by conventional alkylation of the nitrogen atom using known reactions, for example, alkylation with dialkyl sulfate, alkyl halide etc. according to known procedures.

In a preferred embodiment, Q is a substituted aryl, and more preferably, a substituted phenyl group and has the structure shown below.

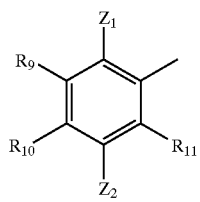

In this structure, $Z_1$, $Z_2$, $R_9$–$R_{11}$ are as defined above both generally and in preferred embodiments. Compounds of this embodiment are prepared as described in scheme 1 above using an appropriately substituted benzaldehyde having structure Q-CHO ($R_5$ is H). These substituted benzaldehydes are readily available from commercial sources or can be easily prepared from known benzaldehydes using well known synthetic chemistry.

In one embodiment, Q is substituted with a nitro group. A preferred position for the nitro group is at $R_{11}$ (where $Z_1$, $Z_2$, $R_9$ and $R_{10}$ are as defined above generally and in preferred embodiments), which nitro group can be further reduced to an amino group using a suitable reducing agent. Generally, the cyano-amine compound or the cyano-sulfonamide compound shown in scheme 3 will be reacted with a reducing agent which will preferentially reduce the nitro group at $R_{11}$ over the cyano group. Any reducing agent having these properties may be used, for example, hydrogen and a Pt/C catalyst. The aniline resulting from the reduction can then be reacted with a sulfonyl chloride ($ClSO_2W$ where W is as defined above) to produce a disulfonamide compound.

The preparation of cyclic urea derivatives in which $N_1$–$R_2$ and $N_2$–$R_2$ together form a urea linkage, i.e. $N_1$—C(O)—$N_2$, provides additional compounds of the invention and provides an additional method of preparing enentiomerically pure compounds of the invention. The cyclic urea compounds can be used, for example, to prepare dialkoxy bis-sulfonamides and other compounds of the invention as shown in the scheme below.

Alternatively, nitric acid can be replaced by sulfuric acid in the scheme below to give sulfonic acid derivatives which can be further converted to sulfonamides and sulfones by known reactions.

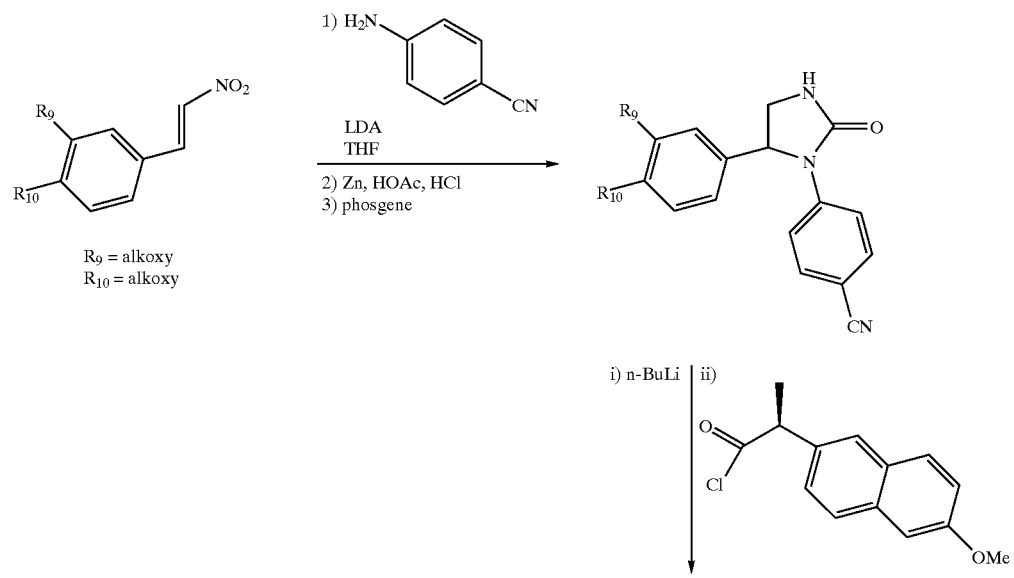

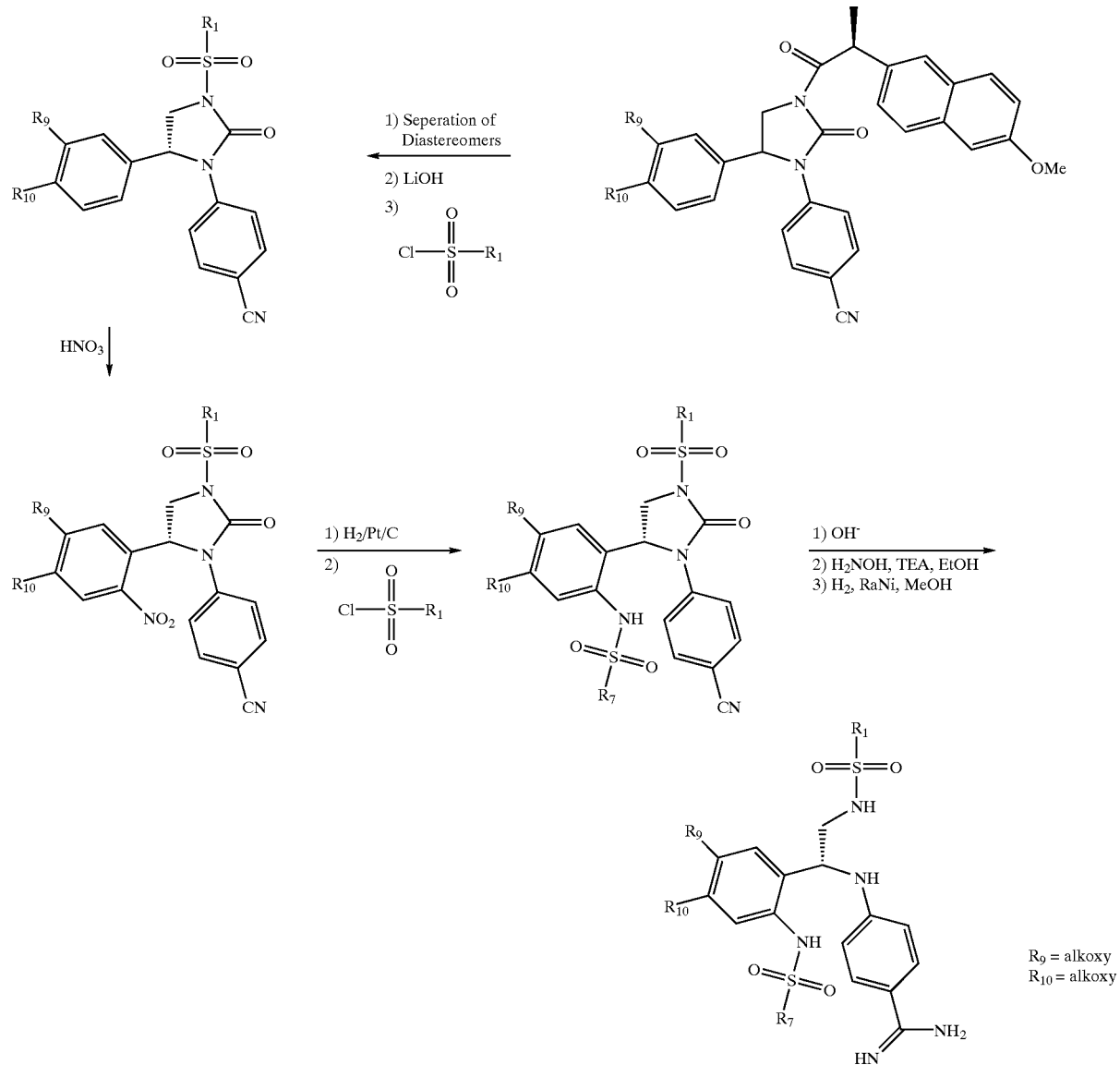

Other compounds of the invention, including heterocyclic compounds, are readily prepared from simple starting materials which can be used in the synthetic schemes described above. For example, beginning with simple nitro and hydroxy substituted aldehydes, condensation as described above provides the corresponding esters which can be converted directly to cyclic urethane or oxazole compounds which can then be further elaborated as already described to provide compounds of the invention. These reactions are shown schematically below for rings fused in the 5-position and 6-position.

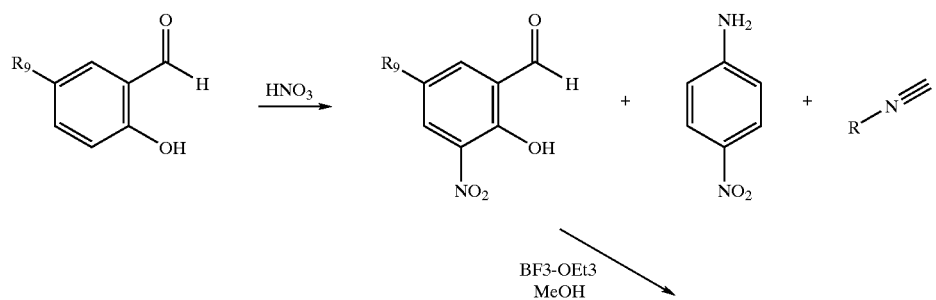

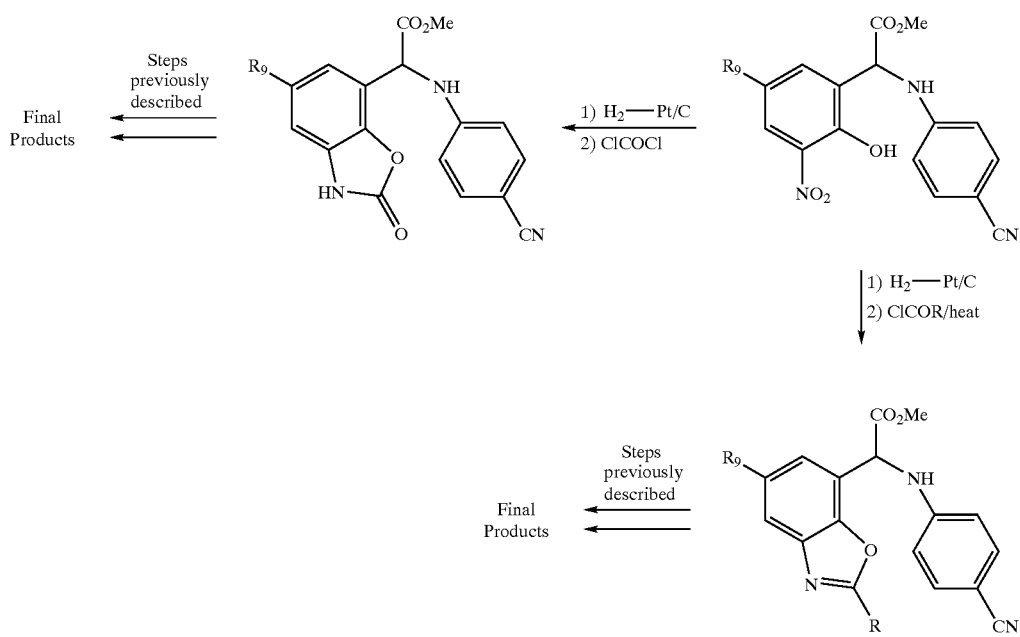

Compounds in which the ring is fused to the 4-position and the 5-position of the phenyl ring are prepared by analogous methods stating with the appropriately substituted aldehyde as shown below.

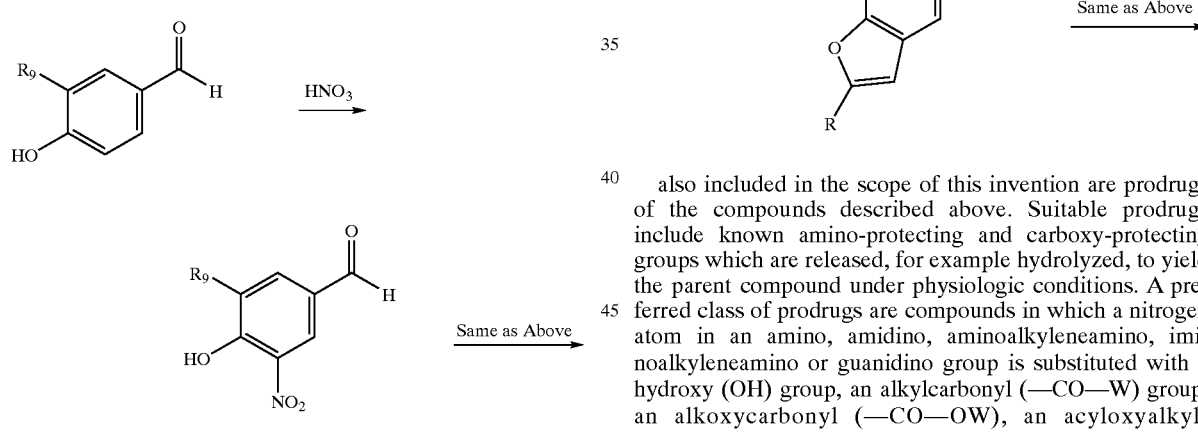

Other fused heterocyclic compounds are prepared using conventional synthetic chemical reactions and appropriately substituted starting materials which are well known in the art of chemical synthesis to provide additional compounds of the invention. For example, fused furan ring systems can be prepared from the corresponding halo and hydroxy substituted aldehydes as shown below.

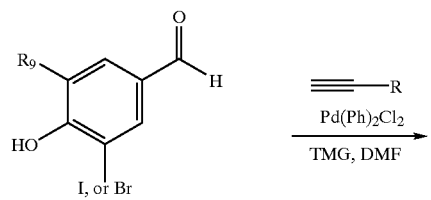

-continued also included in the scope of this invention are prodrugs of the compounds described above. Suitable prodrugs include known amino-protecting and carboxy-protecting groups which are released, for example hydrolyzed, to yield the parent compound under physiologic conditions. A preferred class of prodrugs are compounds in which a nitrogen atom in an amino, amidino, aminoalkyleneamino, iminoalkyleneamino or guanidino group is substituted with a hydroxy (OH) group, an alkylcarbonyl (—CO—W) group, an alkoxycarbonyl (—CO—OW), an acyloxyalkylalkoxycarbonyl (—CO—O—W—O—CO—W) group where W is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. Preferably the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and defluorophenoxy acyl. The reactions are generally exothermic and are carried out in inert solvents at reduced temperatures such as −78 to about 50C. The reactions are usually also carried out in the presence of an inorganic base such as potassium carbonate or sodium bicarbonate, or an organic base such as an amine, including pyridine, triethylamine, etc. One manner of preparing prodrugs is described in WO98/46576, published 22 Oct. 1998.

Using the synthetic methods described above, the following exemplary compounds of the invention shown in Table 2 below can be prepared (m=1). For each entry in the table, X may be carbonyl or $(CR_{4a}R_{4b})_m$ where m=1 or 2; and the benzamidine ring may bear a halogen, hydroxy or alkyl substituent.

TABLE 2

| Compound No | $Z^2$ | $R^1$ | $R^9$ | $R^{10}$ | $R^{11}$ |
|---|---|---|---|---|---|
| 1 | —H | phenyl | OCH$_3$ | benzyloxy | H |
| 2 | —H | 1-methylnaphthyl | OCH$_3$ | benzyloxy | H |
| 3 | —H | 2-methylnaphthyl | OCH$_3$ | benzyloxy | H |
| 4 | —H | N(CH$_3$)$_2$-methylnaphthyl | OCH$_3$ | benzyloxy | H |
| 5 | —H | benzyl | OCH$_3$ | benzyloxy | H |
| 6 | —H | styryl | OCH$_3$ | benzyloxy | H |
| 7 | —H | 2-thienyl | OCH$_3$ | benzyloxy | H |

TABLE 2-continued

[Structure: central benzene ring with substituents R9, R10, R11, Z2, and a CH(X-NHSO2R1)(NH-Ar) group where Ar is 4-amidinophenyl]

| Compound No | Z² | R¹ | R⁹ | R¹⁰ | R¹¹ |
|---|---|---|---|---|---|
| 8 | —H | 4-(acetylamino)-phenyl (N-acetyl-p-toluidide group: 4-CH₃C₆H₄NHC(O)—) | OCH₃ | benzyloxy (—OCH₂C₆H₅) | H |
| 9 | —H | phenyl (tolyl) | OCH₃ | benzyloxy | phenyl-SO₂—NH (N-methyl) |
| 10 | —H | phenyl | OCH₃ | OCH₃ | Br |
| 11 | —H | phenyl | OCH₃ | —CH(CH₂Cl)(OCH₃)-phenyl | H |
| 12 | —H | —CH(CH₃)₂ | OCH₃ | benzyloxy | H |
| 13 | —H | —CH₂CH₂CH₃ | OCH₃ | benzyloxy | CH₃SO₂—NH |
| 14 | —H | 4-nitrophenyl | OCH₃ | benzyloxy | H |
| 15 | —H | 4-fluorophenyl | OCH₃ | benzyloxy | H |
| 16 | —H | 2,4-dichlorophenyl | OCH₃ | benzyloxy | H |

TABLE 2-continued

| Compound No | Z² | R¹ | R⁹ | R¹⁰ | R¹¹ |
|---|---|---|---|---|---|
| 17 | —H | —CH₂CH₃ | OCH₃ | benzyloxymethyl (PhCH₂O-CH₂—) | H |
| 18 | —H | 3-nitrophenyl | OCH₃ | benzyloxymethyl | H |
| 19 | —H | 3-trifluoromethylphenyl | OCH₃ | benzyloxymethyl | H |
| 20 | —H | 4-bromophenyl | OCH₃ | benzyloxymethyl | H |
| 21 | —H | N-(4,5-dimethylthiazol-2-yl)acetamide | OCH₃ | benzyloxymethyl | H |
| 22 | —H | 2,3,4,5-tetramethylphenyl | OCH₃ | benzyloxymethyl | H |
| 23 | —H | 2-nitrophenyl | OCH₃ | benzyloxymethyl | H |
| 24 | —H | —CH₃ | OCH₃ | benzyloxymethyl | H |

TABLE 2-continued
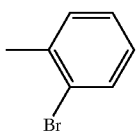
| Compound No | $Z^2$ | $R^1$ | $R^9$ | $R^{10}$ | $R^{11}$ |
|---|---|---|---|---|---|
| 25 | —H | 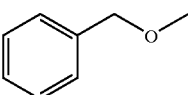 | $OCH_3$ | 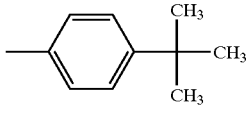 | H |
| 26 | —H | 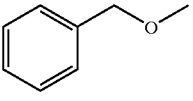 | $OCH_3$ | 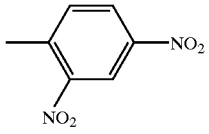 | H |
| 27 | —H | 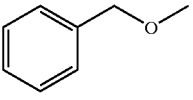 | $OCH_3$ | 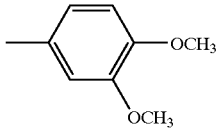 | H |
| 28 | —H | 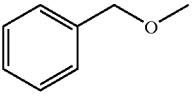 | $OCH_3$ | 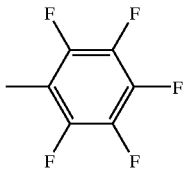 | H |
| 29 | —H | 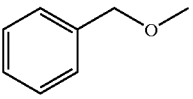 | $OCH_3$ | 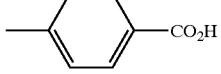 | H |
| 30 | —H | 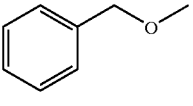 | $OCH_3$ | 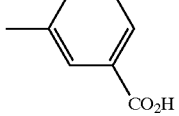 | H |
| 31 | —H | 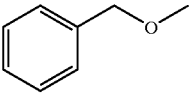 | $OCH_3$ | 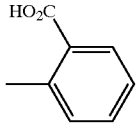 | H |
| 32 | —H | 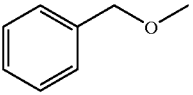 | $OCH_3$ | 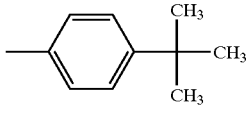 | H |

TABLE 2-continued

| Compound No | $Z^2$ | $R^1$ | $R^9$ | $R^{10}$ | $R^{11}$ |
|---|---|---|---|---|---|
| 33 | —H | —CH$_2$CH$_2$CH$_3$ | OCH$_3$ | benzyloxymethyl (PhCH$_2$OCH$_2$—) | H |
| 34 | —H | —CH$_2$CH$_2$CH$_2$CH$_3$ | OCH$_3$ | benzyloxymethyl (PhCH$_2$OCH$_2$—) | H |
| 35 | —H | 4-isopropylphenyl | OCH$_3$ | benzyloxymethyl (PhCH$_2$OCH$_2$—) | H |
| 36 | —H | 3,5-dichloro-4-hydroxy-2-methylphenyl | OCH$_3$ | benzyloxymethyl (PhCH$_2$OCH$_2$—) | H |
| 37 | —H | —CH$_2$CH$_2$CH$_3$ | OCH$_3$ | PhCH(OCH$_3$)CH$_2$Cl— | H |
| 38 | —H | —CH$_2$CO$_2$CH$_2$CH$_3$ | OCH$_3$ | benzyloxymethyl (PhCH$_2$OCH$_2$—) | H |
| 39 | —H | —CH$_2$CO$_2$H | OCH$_3$ | benzyloxymethyl (PhCH$_2$OCH$_2$—) | H |
| 40 | —H | —(CH$_2$)$_6$CH$_3$ | OCH$_3$ | benzyloxymethyl (PhCH$_2$OCH$_2$—) | H |
| 41 | —H | —CH=CH$_2$ | OCH$_3$ | benzyloxymethyl (PhCH$_2$OCH$_2$—) | H |

TABLE 2-continued

[Structure: benzene ring with substituents R9, R10, R11, Z2, and a CH(X-NHSO2R1)(NH-aryl-C(=NH)NH2) group]

| Compound No | Z² | R¹ | R⁹ | R¹⁰ | R¹¹ |
|---|---|---|---|---|---|
| 42 | —H | —CH₂—C≡CH | OCH₃ | benzyloxy | H |
| 43 | —H | cyclohexyl | OCH₃ | benzyloxy | H |
| 44 | —H | cyclopropyl | OCH₃ | benzyloxy | H |
| 45 | —H | cycloheptyl | OCH₃ | benzyloxy | H |
| 46 | —H | 2-ethylnaphthyl | OCH₃ | benzyloxy | H |
| 47 | —H | 2-methylpyridyl | OCH₃ | benzyloxy | H |
| 48 | —H | 2-methylfuryl | OCH₃ | benzyloxy | H |
| 49 | —H | 2-methylimidazolyl | OCH₃ | benzyloxy | H |
| 50 | —H | 3,4,5-trimethylisoxazolyl | OCH₃ | benzyloxy | H |

TABLE 2-continued

| Compound No | $Z^2$ | $R^1$ | $R^9$ | $R^{10}$ | $R^{11}$ |
|---|---|---|---|---|---|
| 51 | —H | 3-methyl-1H-indol-2-yl | OCH$_3$ | OCH$_2$Ph | H |
| 52 | —H | 3-methyl-1H-isoindol-1-yl | OCH$_3$ | OCH$_2$Ph | H |
| 53 | —H | 4-methylpyrimidin-2-yl | OCH$_3$ | OCH$_2$Ph | H |
| 54 | —H | 3-methylpyrazin-2-yl | OCH$_3$ | OCH$_2$Ph | H |
| 55 | —H | 3-methylpyridazin-2-yl | OCH$_3$ | OCH$_2$Ph | H |
| 56 | —H | 2-methyl-1H-pyrrol-2-yl | OCH$_3$ | OCH$_2$Ph | H |
| 57 | —H | 2-methylthiazol-2-yl | OCH$_3$ | OCH$_2$Ph | H |
| 58 | —H | 2-methyl-1H-imidazol-2-yl | OCH$_3$ | OCH$_2$Ph | H |
| 59 | —H | 1-carboxy-1-phenylethyl | OCH$_3$ | OCH$_2$Ph | H |

TABLE 2-continued

Structure: Core with X-NHSO₂R₁ at top of CH group, attached to benzene ring with R9, R10, R11 substituents and Z2; NH linking to para-amidinophenyl group.

| Compound No | Z² | R¹ | R⁹ | R¹⁰ | R¹¹ |
|---|---|---|---|---|---|
| 60 | —H | 4-methylphenyl | OCH₂CH₃ | OCH₂CH₃ | H |
| 61 | —H | 8-methylnaphth-1-yl | OCH₂CH₂CH₃ | OCH₂-phenyl-OCH₃ | H |
| 62 | —H | 6-methylnaphth-2-yl | OCH₂CH₂CH₃ | OCH₂-phenyl-OCH₃ | H |
| 63 | —H | 6-methyl-1-(N(CH₃)₂)naphthyl | OCH₂CH₃ | OCH₂-phenyl-OCH₃ | H |
| 64 | —H | 4-ethylphenyl | OCH₂CH₃ | OCH₂-phenyl-OCH₃ | H |
| 65 | —H | (E)-styryl | OCH₂CH₃ | OCH₂-phenyl-OCH₃ | H |
| 66 | —H | 5-methylthien-2-yl | OCH₂(CH₂)₄CH₃ | OCH₂-phenyl-OCH₃ | H |
| 67 | —H | 4-(N-acetylamino)-methylphenyl | OCH₂CH₃ | OCH(CH₃)-phenyl-OCH₃ | H |
| 68 | —H | 4-methylphenyl | OCH₂CH₃ | OCH₂-phenyl-OCH₃ | phenyl-SO₂NHCH₃ |

TABLE 2-continued

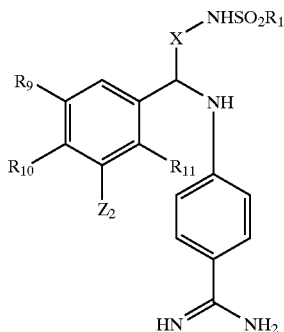

| Compound No | $Z^2$ | $R^1$ | $R^9$ | $R^{10}$ | $R^{11}$ |
|---|---|---|---|---|---|
| 69 | —H | phenyl | OCH₂CH₃ | OCH₃ | Br |
| 70 | —H | phenyl | OCH₂CH₃ | PhCH(CH₂Cl)O— | H |
| 71 | —H | —CH(CH₃)₂ | OCH₂CH₃ | PhCH₂O— | H |
| 72 | —H | —CH₂CH₂CH₃ | OCH₂CH₃ | PhCH₂O— | CH₃SO₂—NH |
| 73 | —H | 4-NO₂-phenyl | OCH₂CH₃ | PhCH₂O— | H |
| 74 | —H | —CH₂CH₂CH₃ | OCH₂CH₃ | PhCH₂O— | CH₃CH₂—O₂CCH₂SO₂NH— |
| 75 | —H | —CH₂CH₂CH₃ | OCH₂CH₃ | PhCH₂O— | HO₂CCH₂SO₂NH— |
| 76 | —H | —CH₂CH₂CH₃ | OCH₂CH₃ | PhCH₂O— | CH₃SO₂N(CH₂CO₂CH₂CH₃)— |
| 77 | —H | —CH₂CH₂CH₃ | OCH₂CH₃ | PhCH₂O— | CH₃SO₂N(CH₂CO₂H)— |
| 78 | —H | phenyl | OCH₂CH₃ | PhCH₂O— | H |

TABLE 2-continued

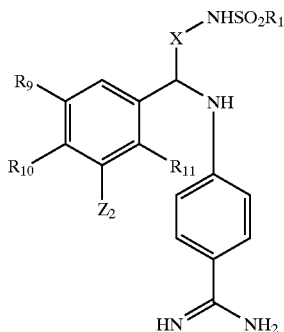

| Compound No | Z² | R¹ | R⁹ | R¹⁰ | R¹¹ |
|---|---|---|---|---|---|
| 79 | —H | 2,5-dichloro-3-methylphenyl | OCH₂CH₃ | benzyloxymethyl | H |
| 80 | —H | —CH₂CH₃ | OCH₂CH₃ | benzyloxymethyl | H |
| 81 | —H | 3-nitrophenyl | OCH₂CH₃ | benzyloxymethyl | H |
| 82 | —H | 3-trifluoromethylphenyl | OCH₂CH₃ | benzyloxymethyl | H |
| 83 | —H | 4-bromophenyl | OCH₂CH₃ | benzyloxymethyl | H |
| 84 | —H | N-(4,5-dimethylthiazol-2-yl)acetamide | OCH₂CH₃ | benzyloxymethyl | H |
| 85 | —H | 2,3,4,5-tetramethylphenyl | OCH₂CH₃ | benzyloxymethyl | H |
| 86 | —H | 2-nitrophenyl | OCH₂CH₃ | benzyloxymethyl | H |

TABLE 2-continued

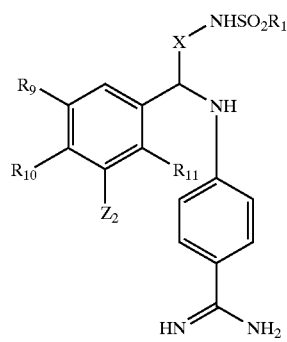

| Compound No | $Z^2$ | $R^1$ | $R^9$ | $R^{10}$ | $R^{11}$ |
|---|---|---|---|---|---|
| 87 | —H | —CH$_3$ | OCH$_2$CH$_3$ | benzyloxy | H |
| 88 | —H | 2-bromophenyl | OCH$_2$CH$_3$ | benzyloxy | H |
| 89 | —H | 4-tert-butylphenyl | OCH$_2$CH$_3$ | benzyloxy | H |
| 90 | —H | 2,4-dinitrophenyl | OCH$_2$CH$_3$ | benzyloxy | H |
| 91 | —H | 3,4-dimethoxyphenyl | OCH$_2$CH$_3$ | benzyloxy | H |
| 92 | —H | pentafluorophenyl | OCH$_2$CH$_3$ | benzyloxy | H |
| 93 | —H | 4-carboxyphenyl | OCH$_2$CH$_3$ | benzyloxy | H |
| 94 | —H | 3-carboxyphenyl | OCH$_2$CH$_3$ | benzyloxy | H |

TABLE 2-continued

[Structure: substituted benzene with R9, R10, R11, Z2 substituents; CH(X-NHSO2R1)(NH-aryl-C(=NH)NH2)]

| Compound No | Z² | R¹ | R⁹ | R¹⁰ | R¹¹ |
|---|---|---|---|---|---|
| 95 | —H | 2-(HO₂C)-phenyl-methyl | OCH₂CH₃ | PhCH₂O— | H |
| 96 | —H | —CH₂CH₂CH₃ | OCH₂CH₃ | PhCH₂O— | H |
| 97 | —H | —CH₂CH₂CH₂CH₃ | OCH₂CH₃ | PhCH₂O— | H |
| 98 | —H | 4-isopropylphenyl | OCH₂CH₃ | PhCH₂O— | H |
| 99 | —H | 3,5-dichloro-4-hydroxy-2-methylphenyl | OCH₂CH₃ | PhCH₂O— | H |
| 100 | —H | —CH₂CH₂CH₃ | OCH₂CH₃ | Ph-CH(CH₂Cl)-O— | H |
| 101 | —H | —(CH₂)₆CH₃ | OCH₂CH₃ | PhCH₂O— | H |
| 102 | —H | —CH=CH₂ | OCH₂CH₃ | PhCH₂O— | H |
| 103 | —H | —CH₂—C≡CH | OCH₂CH₃ | PhCH₂O— | H |

TABLE 2-continued
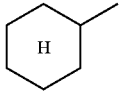
| Compound No | $Z^2$ | $R^1$ | $R^9$ | $R^{10}$ | $R^{11}$ |
|---|---|---|---|---|---|
| 104 | —H | 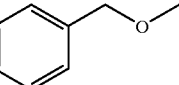 | $OCH_2CH_3$ | 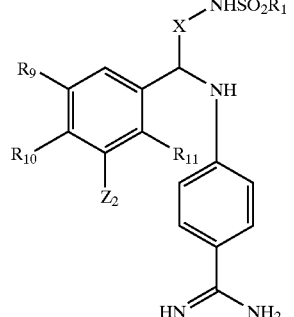 | H |
| 105 | —H | 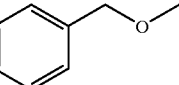 | $OCH_2CH_3$ |  | H |
| 106 | —H | 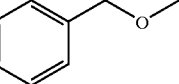 | $OCH_2CH_3$ | 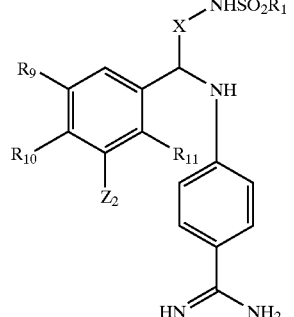 | H |
| 107 | —H | 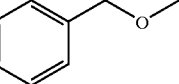 | $OCH_2CH_3$ | 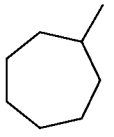 | H |
| 108 | —H | 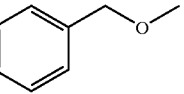 | $OCH_2CH_3$ | 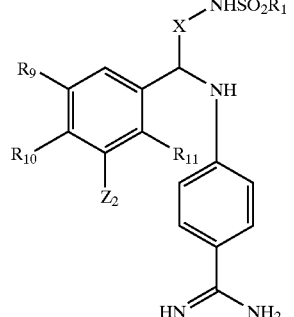 | H |
| 109 | —H | 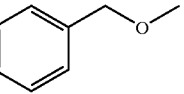 | $OCH_2CH_3$ | 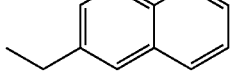 | H |
| 110 | —H | 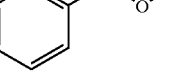 | $OCH_2CH_3$ | 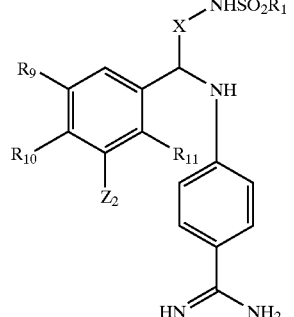 | H |
| 111 | —H | 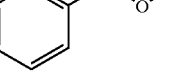 | $OCH_2CH_3$ | 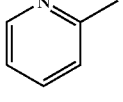 | H |
| 112 | —H | 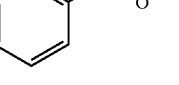 | $OCH_2CH_3$ | 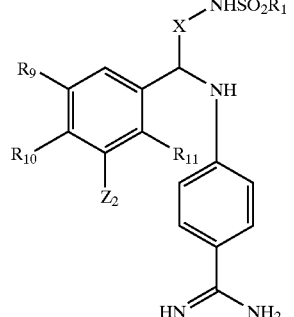 | H |

TABLE 2-continued

[Structure: benzene ring with substituents R9, R10, R11, Z2, and a CH(X-NHSO2R1)(NH-C6H4-C(=NH)NH2) group]

| Compound No | Z² | R¹ | R⁹ | R¹⁰ | R¹¹ |
|---|---|---|---|---|---|
| 113 | —H | 3-methyl-1H-isoindole | OCH₂CH₃ | OCH₂-C₆H₅ | H |
| 114 | —H | 4-methylpyrimidine | OCH₂CH₃ | OCH₂-C₆H₅ | H |
| 115 | —H | 3-methylpyrazine | OCH₂CH₃ | OCH₂-C₆H₅ | H |
| 116 | —H | 3-methylpyridazine | OCH₂CH₃ | OCH₂-C₆H₅ | H |
| 117 | —H | 2-methyl-1H-pyrrole | OCH₂CH₃ | OCH₂-C₆H₅ | H |
| 118 | —H | 2-methyl-1H-imidazole | OCH₂CH₃ | OCH₂-C₆H₅ | H |
| 119 | —H | 2-methylthiazole | OCH₂CH₃ | OCH₂-C₆H₅ | H |
| 120 | —H | 2-phenylpropanoic acid | OCH₂CH₃ | OCH₂-C₆H₅ | H |
| 121 | —H | methylbenzene (tolyl) | OH | OCH₂-C₆H₅ | H |

TABLE 2-continued
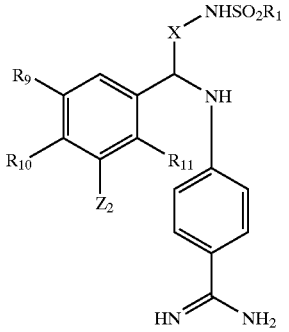
| Compound No | Z² | R¹ | R⁹ | R¹⁰ | R¹¹ |
|---|---|---|---|---|---|
| 122 | —H | 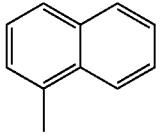 | OH | 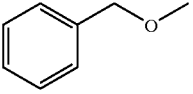 | H |
| 123 | —H | 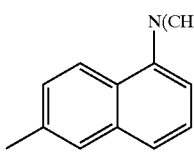 | OH | 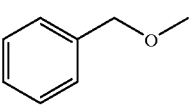 | H |
| 124 | —H | 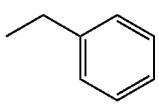 | OH | 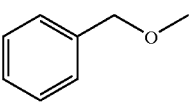 | H |
| 125 | —H | 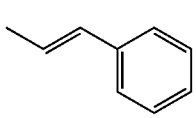 | OH | 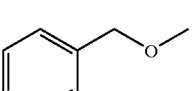 | H |
| 126 | —H | 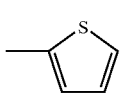 | OH | 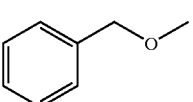 | H |
| 127 | —H | 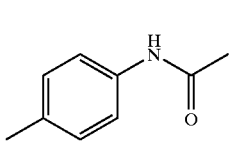 | OH | 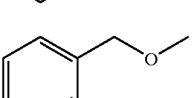 | H |
| 128 | —H | 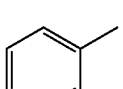 | OH | 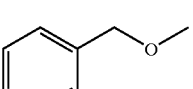 | 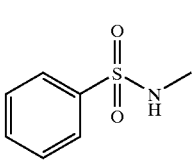 |
| 129 | —H | 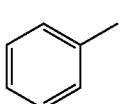 | OH | OCH₃ | Br |
| 130 | —H | 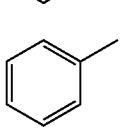 | OH | 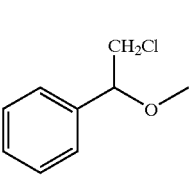 | H |

TABLE 2-continued

[Structure: A benzene ring substituted with R9, R10, Z2, R11, and a carbon bearing X-NHSO2R1, NH-linked to a para-amidinophenyl group]

| Compound No | Z² | R¹ | R⁹ | R¹⁰ | R¹¹ |
|---|---|---|---|---|---|
| 131 | —H | —CH(CH₃)₂ | OH | benzyloxy (—O—CH₂—C₆H₅) | H |
| 132 | —H | —CH₂CH₂CH₃ | OH | benzyloxy | CH₃SO₂—NH— |
| 133 | —H | 4-nitrophenyl | OH | benzyloxy | H |
| 134 | —H | 4-fluorophenyl | OH | benzyloxy | H |
| 135 | —H | 2,5-dichlorophenyl | OH | benzyloxy | H |
| 136 | —H | —CH₂CH₃ | OH | benzyloxy | H |
| 137 | —H | 3-nitrophenyl | OH | benzyloxy | H |
| 138 | —H | 3-(trifluoromethyl)phenyl | OH | benzyloxy | H |
| 139 | —H | 4-bromophenyl | OH | benzyloxy | H |

TABLE 2-continued
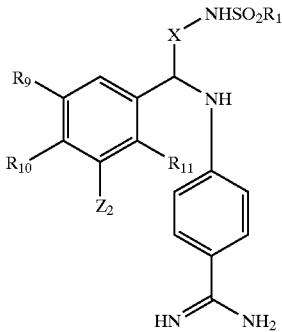
| Compound No | Z² | R¹ | R⁹ | R¹⁰ | R¹¹ |
|---|---|---|---|---|---|
| 140 | —H | 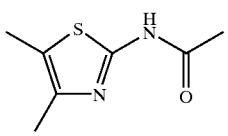 | OH | 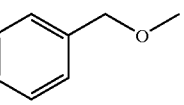 | H |
| 141 | —H | 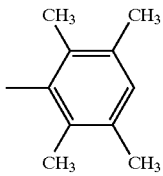 | OH | 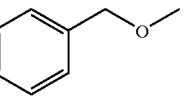 | H |
| 142 | —H | 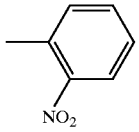 | OH | 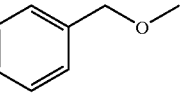 | H |
| 143 | —H | —CH₃ | OH | 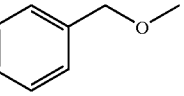 | H |
| 144 | —H |  | OH | 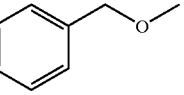 | H |
| 145 | —H | 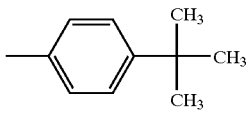 | OH | 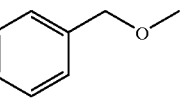 | H |
| 146 | —H | 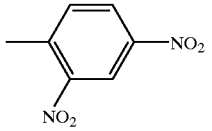 | OH | 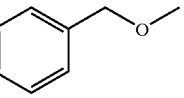 | H |
| 147 | —H | 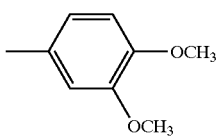 | OH | 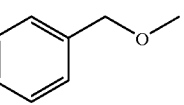 | H |

TABLE 2-continued
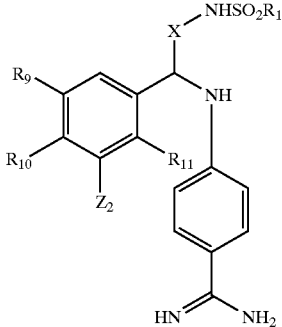
| Compound No | $Z^2$ | $R^1$ | $R^9$ | $R^{10}$ | $R^{11}$ |
|---|---|---|---|---|---|
| 148 | —H | 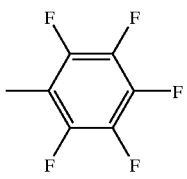 | OH | 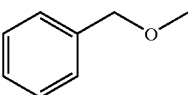 | H |
| 149 | —H | 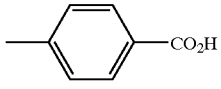 | OH | 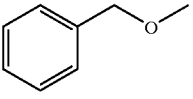 | H |
| 150 | —H | 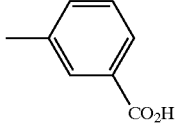 | OH | 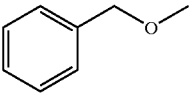 | H |
| 151 | —H | 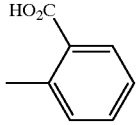 | OH | 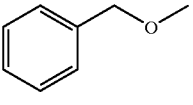 | H |
| 152 | —H | —CH$_2$CH$_2$CH$_3$ | OH | 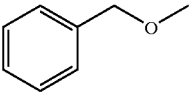 | H |
| 153 | —H | —CH$_2$CH$_2$CH$_2$CH$_3$ | OH | 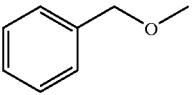 | H |
| 154 | —H | 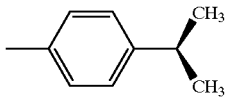 | OH | 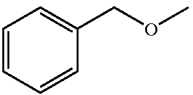 | H |
| 155 | —H | 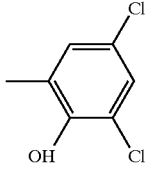 | OH | 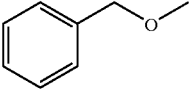 | H |

TABLE 2-continued
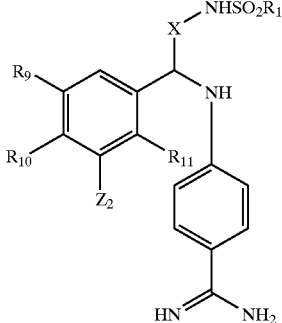
| Compound No | Z² | R¹ | R⁹ | R¹⁰ | R¹¹ |
|---|---|---|---|---|---|
| 156 | —H | —CH₂CH₂CH₃ | OH | 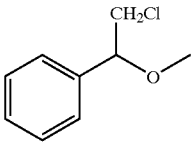 | H |
| 157 | —H | —(CH₂)₆CH₃ | OH | 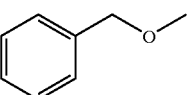 | H |
| 158 | —H | —CH=CH₂ | OH | 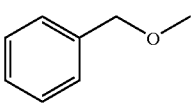 | H |
| 159 | —H | —CH₂—C≡CH | OH | 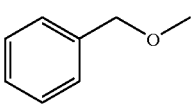 | H |
| 160 | —H | 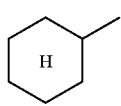 | OH | 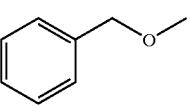 | H |
| 161 | —H |  | OH | 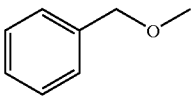 | H |
| 162 | —H | 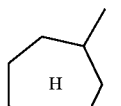 | OH | 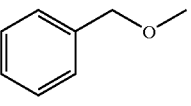 | H |
| 163 | —H | 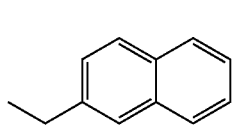 | OH | 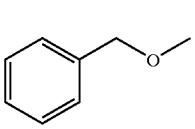 | H |
| 164 | —H | 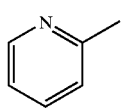 | OH | 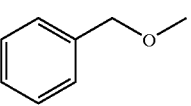 | H |

TABLE 2-continued
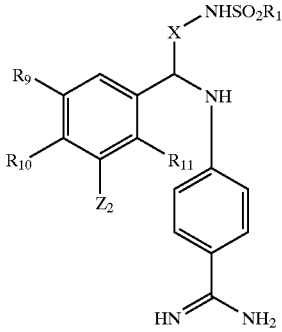
| Compound No | Z² | R¹ | R⁹ | R¹⁰ | R¹¹ |
|---|---|---|---|---|---|
| 165 | —H | 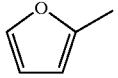 | OH | 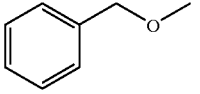 | H |
| 166 | —H | 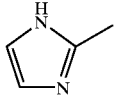 | OH | 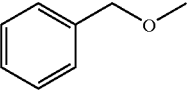 | H |
| 167 | —H | 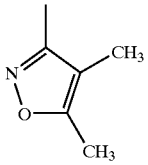 | OH | 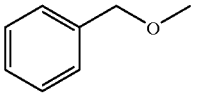 | H |
| 168 | —H | 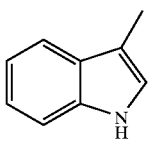 | OH | 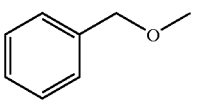 | H |
| 169 | —H | 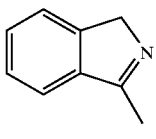 | OH | 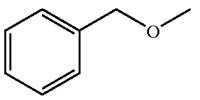 | H |
| 170 | —H | 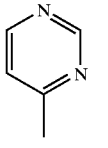 | OH | 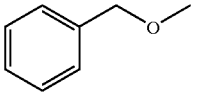 | H |
| 171 | —H | 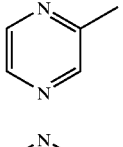 | OH | 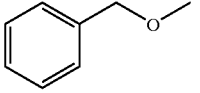 | H |
| 172 | —H | 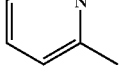 | OH | 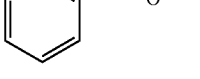 | H |
| 173 | —H | 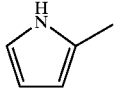 | OH | 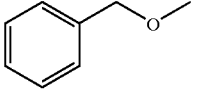 | H |

TABLE 2-continued
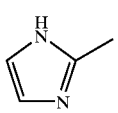
| Compound No | Z² | R¹ | R⁹ | R¹⁰ | R¹¹ |
|---|---|---|---|---|---|
| 174 | —H | 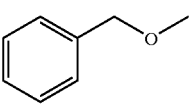 | OH | 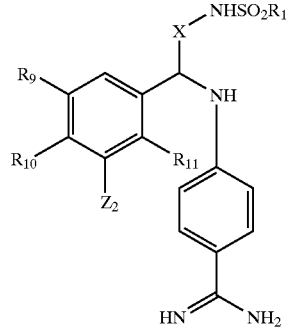 | H |
| 175 | —H |  | OH | 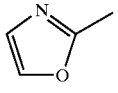 | H |
| 176 | —H | 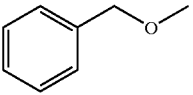 | OH | 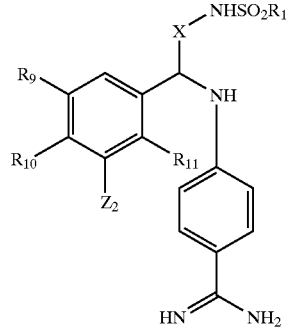 | H |
| 177 | —H |  | —CH₃ | 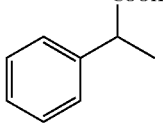 | H |
| 178 | —H | 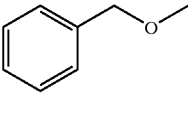 | —CH₂CH₃ | 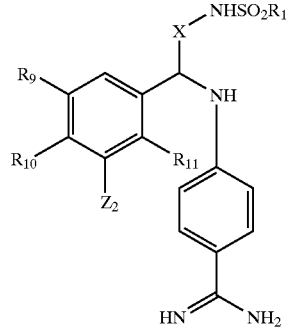 | H |
| 179 | —H |  | —CH₂CH₃ | 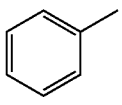 | H |
| 180 | —H | 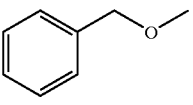 | —CH₂CH₃ | 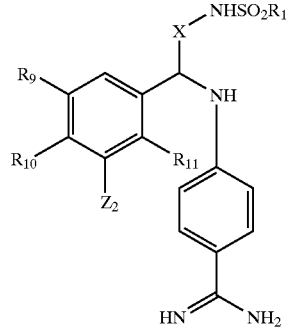 | H |
| 181 | —H |  | —CH₂CH₂CH₃ | 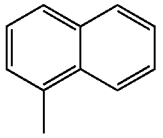 | H |
| 182 | —H | 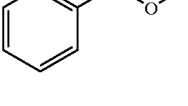 | —CH₃ | 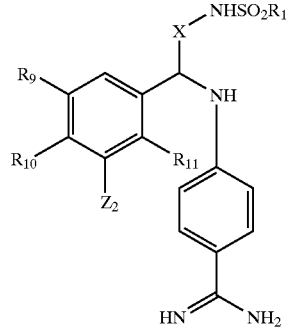 | H |

TABLE 2-continued
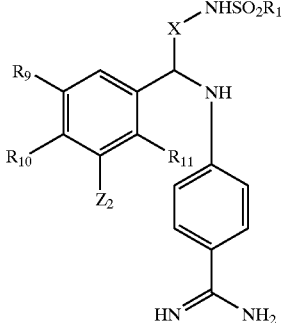
| Compound No | $Z^2$ | $R^1$ | $R^9$ | $R^{10}$ | $R^{11}$ |
|---|---|---|---|---|---|
| 183 | —H | 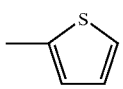 | —CH(CH$_3$)$_2$ | 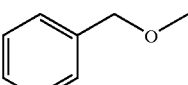 | H |
| 184 | —H | 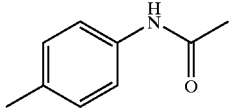 | —CH$_3$ | 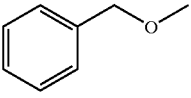 | H |
| 185 | —H | 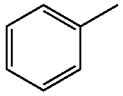 | —CH$_2$(CH$_2$)$_3$CH$_3$ | 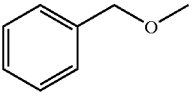 | 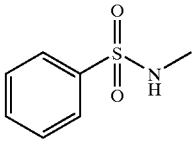 |
| 186 | —H | 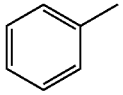 | —CH$_3$ | OCH$_3$ | Br |
| 187 | —H | 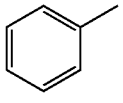 | —CH$_3$ | 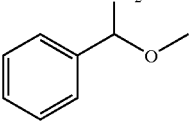 | H |
| 188 | —H | —CH(CH$_3$)$_2$ | —CH$_3$ | 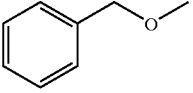 | H |
| 189 | —H | —CH$_2$CH$_2$CH$_3$ | —CH$_3$ | 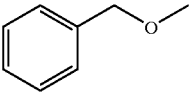 | CH$_3$SO$_2$—NH— |
| 190 | —H | 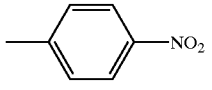 | —CH$_3$ | 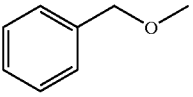 | H |
| 191 | —H | 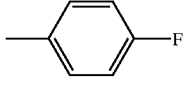 | —CH$_3$ | 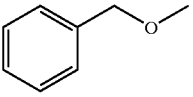 | H |

TABLE 2-continued

| Compound No | $Z^2$ | $R^1$ | $R^9$ | $R^{10}$ | $R^{11}$ |
|---|---|---|---|---|---|
| 192 | —H | 2,5-dichlorophenyl | —CH₃ | benzyloxy | H |
| 193 | —H | —CH₂CH₃ | —CH₃ | benzyloxy | H |
| 194 | —H | 3-nitrophenyl | —CH₃ | benzyloxy | H |
| 195 | —H | 3-trifluoromethylphenyl | —CH₃ | benzyloxy | H |
| 196 | —H | 4-bromophenyl | —CH₃ | benzyloxy | H |
| 197 | —H | 5-acetamidothien-2-yl | —CH₃ | benzyloxy | H |
| 198 | —H | 2,3,4,5-tetramethylphenyl | —CH₃ | benzyloxy | H |
| 199 | —H | 2-nitrophenyl | —CH₃ | benzyloxy | H |

TABLE 2-continued
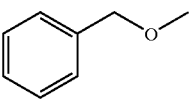
| Compound No | $Z^2$ | $R^1$ | $R^9$ | $R^{10}$ | $R^{11}$ |
|---|---|---|---|---|---|
| 200 | —H | —CH$_3$ | —CH$_3$ | 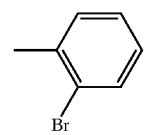 | H |
| 201 | —H | 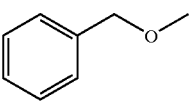 | —CH$_3$ | 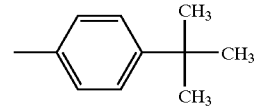 | H |
| 202 | —H | 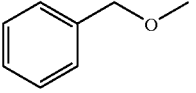 | —CH$_3$ | 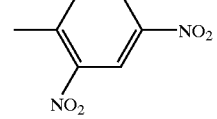 | H |
| 203 | —H | 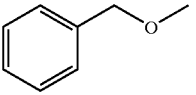 | —CH$_3$ | 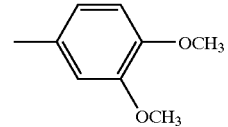 | H |
| 204 | —H | 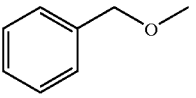 | —CH$_3$ | 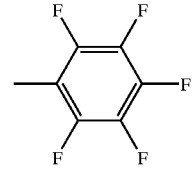 | H |
| 205 | —H | 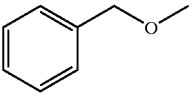 | —CH$_3$ | 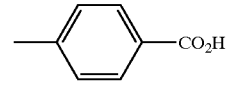 | H |
| 206 | —H | 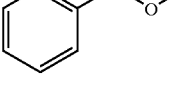 | —CH$_3$ | 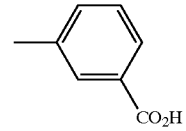 | H |
| 207 | —H | 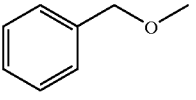 | —CH$_3$ | 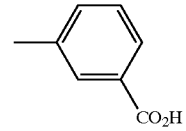 | H |

TABLE 2-continued
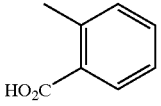
| Compound No | Z² | R¹ | R⁹ | R¹⁰ | R¹¹ |
|---|---|---|---|---|---|
| 208 | —H | 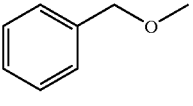 | —CH₃ | 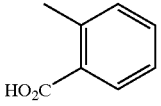 | H |
| 209 | —H | —CH₂CH₂CH₃ | —CH₃ | 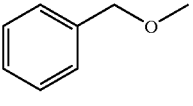 | H |
| 210 | —H | —CH₂CH₂CH₂CH₃ | —CH₃ | 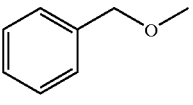 | H |
| 211 | —H | 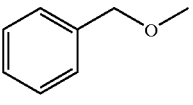 | —CH₃ | 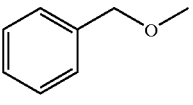 | H |
| 212 | —H | 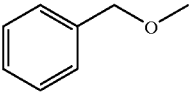 | —CH₃ | 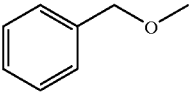 | H |
| 213 | —H | —CH₂CH₂CH₃ | —CH₃ | 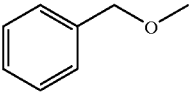 | H |
| 214 | —H | —(CH₂)₆CH₃ | —CH₃ | 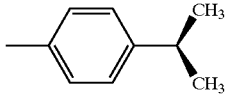 | H |
| 215 | —H | —CH=CH₂ | —CH₃ | 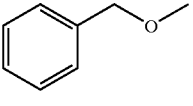 | H |
| 216 | —H | —CH₂—C≡CH | —CH₃ | 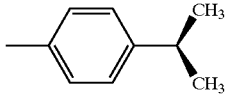 | H |

TABLE 2-continued
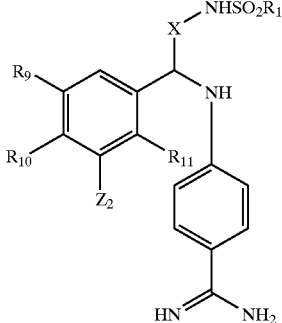
| Compound No | $Z^2$ | $R^1$ | $R^9$ | $R^{10}$ | $R^{11}$ |
|---|---|---|---|---|---|
| 217 | —H | 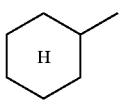 | —CH$_3$ | 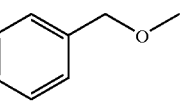 | H |
| 218 | —H |  | —CH$_3$ | 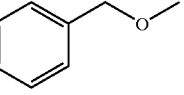 | H |
| 219 | —H | 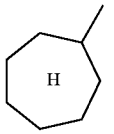 | —CH$_3$ | 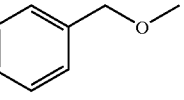 | H |
| 220 | —H | 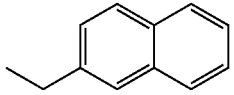 | —CH$_3$ | 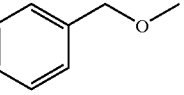 | H |
| 221 | —H | 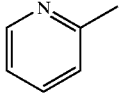 | —CH$_3$ | 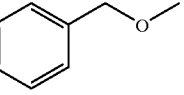 | H |
| 222 | —H | 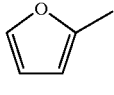 | —CH$_3$ | 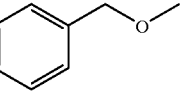 | H |
| 223 | —H | 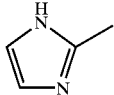 | —CH$_3$ | 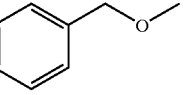 | H |
| 224 | —H | 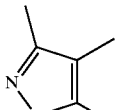 | —CH$_3$ | 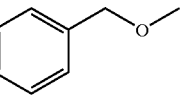 | H |
| 225 | —H | 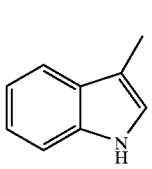 | —CH$_3$ | 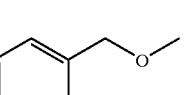 | H |

TABLE 2-continued
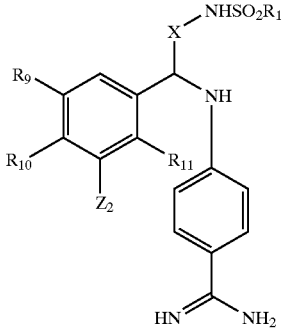
| Compound No | Z² | R¹ | R⁹ | R¹⁰ | R¹¹ |
|---|---|---|---|---|---|
| 226 | —H | 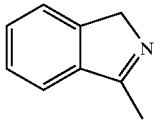 | —CH₃ | 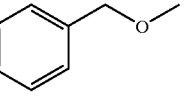 | H |
| 227 | —H | 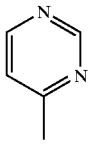 | —CH₃ | 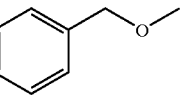 | H |
| 228 | —H | 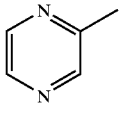 | —CH₃ | 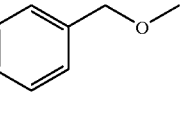 | H |
| 229 | —H | 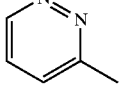 | —CH₃ | 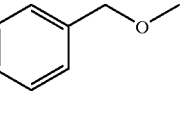 | H |
| 230 | —H | 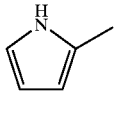 | —CH₃ | 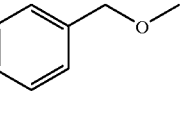 | H |
| 231 | —H | 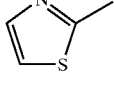 | —CH₃ | 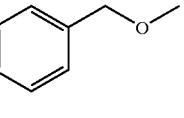 | H |
| 232 | —H | 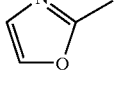 | —CH₃ | 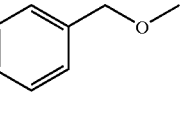 | H |
| 233 | —H | 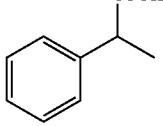 | —CH₃ | 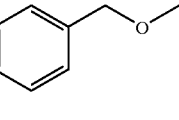 | H |
| 234 | —H | 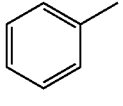 | —CH=CH₂ | 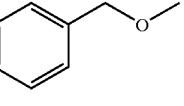 | H |

TABLE 2-continued
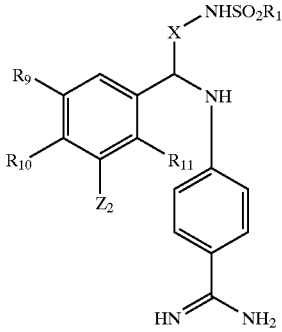
| Compound No | $Z^2$ | $R^1$ | $R^9$ | $R^{10}$ | $R^{11}$ |
| --- | --- | --- | --- | --- | --- |
| 235 | —H | 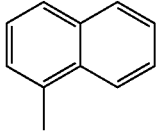 | —CH=CH$_2$ | 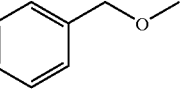 | H |
| 236 | —H | 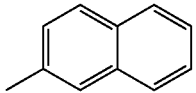 | —CH=CH$_2$ | 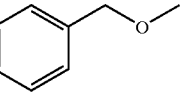 | H |
| 237 | —H | 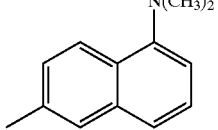 | —CH=CH$_2$ | 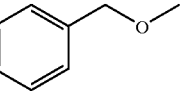 | H |
| 238 | —H | 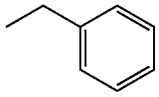 | —CH=CH$_2$ | 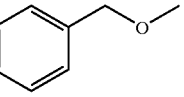 | H |
| 239 | —H | 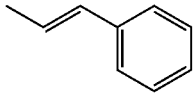 | —CH=CHCH$_3$ | 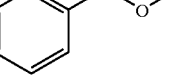 | H |
| 240 | —H | 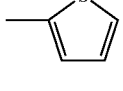 | —CH=CH$_2$ | 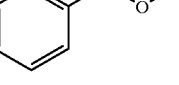 | H |
| 241 | —H | 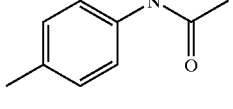 | —CH=CH$_2$ | 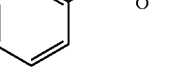 | H |
| 242 | —H | 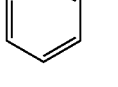 | —CH=CH$_2$ | 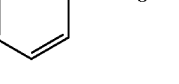 | 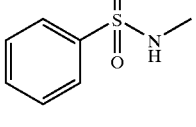 |
| 243 | —H | 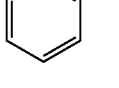 | —CH=CH$_2$ | OCH$_3$ | Br |

TABLE 2-continued

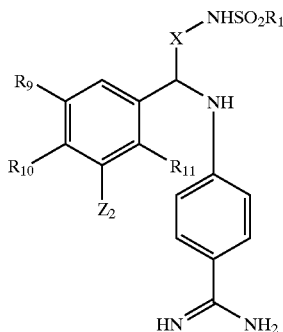

| Compound No | $Z^2$ | $R^1$ | $R^9$ | $R^{10}$ | $R^{11}$ |
|---|---|---|---|---|---|
| 244 | —H | phenyl | —CH=CH$_2$ | 1-(chloromethyl)-1-methoxy benzyl (PhCH(OMe)CH$_2$Cl) | H |
| 245 | —H | —CH(CH$_3$)$_2$ | —CH=CHCH$_2$CH$_3$ | benzyloxymethyl (PhCH$_2$OCH$_2$—) | H |
| 246 | —H | —CH$_2$CH$_2$CH$_3$ | —CH=CH$_2$ | benzyloxymethyl (PhCH$_2$OCH$_2$—) | CH$_3$SO$_2$—NH— |
| 247 | —H | 4-nitrophenyl | —CH=CH$_2$ | benzyloxymethyl (PhCH$_2$OCH$_2$—) | H |
| 248 | —H | 4-fluorophenyl | —CH=CH$_2$ | benzyloxymethyl (PhCH$_2$OCH$_2$—) | H |
| 249 | —H | 2,5-dichlorophenyl | —CH=CH$_2$ | benzyloxymethyl (PhCH$_2$OCH$_2$—) | H |
| 250 | —H | —CH$_2$CH$_3$ | —CH=CH$_2$ | benzyloxymethyl (PhCH$_2$OCH$_2$—) | H |
| 251 | —H | 3-nitrophenyl | —CH=CH$_2$ | benzyloxymethyl (PhCH$_2$OCH$_2$—) | H |
| 252 | —H | 3-(trifluoromethyl)phenyl | —CH$_2$CH=CH$_2$ | benzyloxymethyl (PhCH$_2$OCH$_2$—) | H |

TABLE 2-continued

| Compound No | $Z^2$ | $R^1$ | $R^9$ | $R^{10}$ | $R^{11}$ |
|---|---|---|---|---|---|
| 253 | —H | 4-bromophenyl | —CH=CH$_2$ | benzyloxymethyl | H |
| 254 | —H | 5-methyl-2-acetamidothiophene | —CH=CH$_2$ | benzyloxymethyl | H |
| 255 | —H | 2,3,5,6-tetramethylphenyl | —CH=CH$_2$ | benzyloxymethyl | H |
| 256 | —H | 2-nitrophenyl | —CH=CH$_2$ | benzyloxymethyl | H |
| 257 | —H | —CH$_3$ | —CH$_2$CH=CH$_2$ | benzyloxymethyl | H |
| 258 | —H | 2-bromophenyl | —CH=CH$_2$ | benzyloxymethyl | H |
| 259 | —H | 4-tert-butylphenyl | —CH=CH$_2$ | benzyloxymethyl | H |
| 260 | —H | 2,4-dinitrophenyl | —CH=CH$_2$ | benzyloxymethyl | H |

TABLE 2-continued
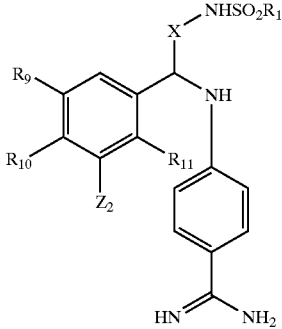
| Compound No | $Z^2$ | $R^1$ | $R^9$ | $R^{10}$ | $R^{11}$ |
|---|---|---|---|---|---|
| 261 | —H | 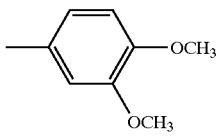 3,4-dimethoxyphenyl | —CH=CH$_2$ | 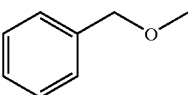 OBn | H |
| 262 | —H | 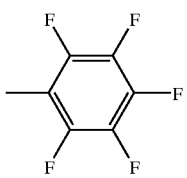 pentafluorophenyl | —CH=CH$_2$ | 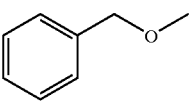 OBn | H |
| 263 | —H | 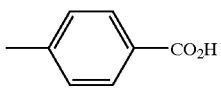 4-CO$_2$H-phenyl | —CH=CH$_2$ | 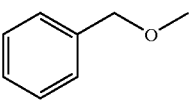 OBn | H |
| 264 | —H | 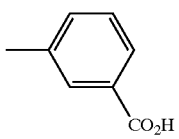 3-CO$_2$H-phenyl | —CH=CH$_2$ | 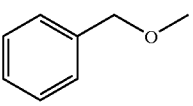 OBn | H |
| 265 | —H | —CH$_2$CH$_2$CH$_3$ | —CH=CH$_2$ | 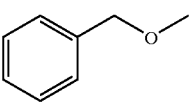 OBn | H |
| 266 | —H | —CH$_2$CH$_2$CH$_2$CH$_3$ | —CH=CH$_2$ | 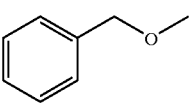 OBn | H |
| 267 | —H | 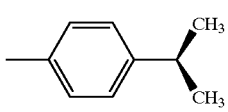 4-isopropylphenyl | —CH=CH$_2$ | 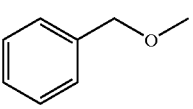 OBn | H |
| 268 | —H | 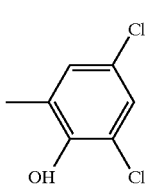 3,5-dichloro-4-hydroxyphenyl | —CH=CH$_2$ | 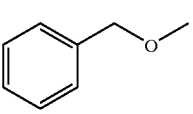 OBn | H |

TABLE 2-continued
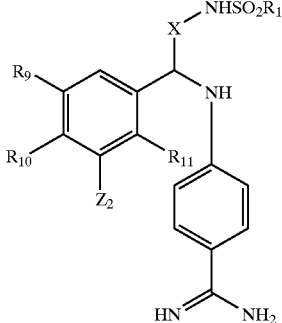
| Compound No | Z² | R¹ | R⁹ | R¹⁰ | R¹¹ |
|---|---|---|---|---|---|
| 269 | —H | —CH₂CH₂CH₃ | —CH=CH₂ | 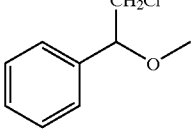 | H |
| 270 | —H | —(CH₂)₆CH₃ | —CH=CH₂ | 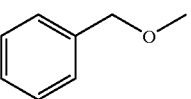 | H |
| 271 | —H | —CH=CH₂ | —CH=CH₂ | 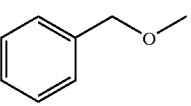 | H |
| 272 | —H | —CH₂—C≡CH | —CH=CH₂ | 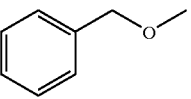 | H |
| 273 | —H | 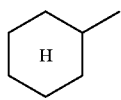 | —CH=CH₂ | 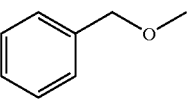 | H |
| 274 | —H |  | —CH=CH₂ | 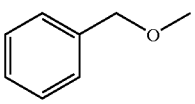 | H |
| 275 | —H | 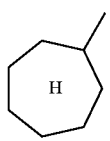 | —CH=CH₂ | 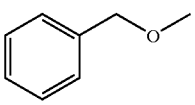 | H |
| 276 | —H | 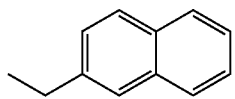 | —CH=CH₂ | 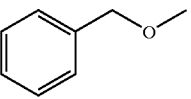 | H |
| 277 | —H | 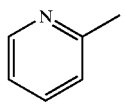 | —CH=CH₂ | 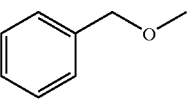 | H |

TABLE 2-continued

| Compound No | Z² | R¹ | R⁹ | R¹⁰ | R¹¹ |
|---|---|---|---|---|---|
| 278 | —H | 2-furyl | —CH=CH₂ | benzyloxy | H |
| 279 | —H | 2-(1H-imidazolyl) | —CH=CH₂ | benzyloxy | H |
| 280 | —H | 3-(1H-indolyl) | —CH=CH₂ | benzyloxy | H |
| 281 | —H | 3-isoindolyl | —CH=CH₂ | benzyloxy | H |
| 282 | —H | 4-pyrimidinyl | —CH=CH₂ | benzyloxy | H |
| 283 | —H | 2-pyrazinyl | —CH=CH₂ | benzyloxy | H |
| 284 | —H | 3-pyridazinyl | —CH=CH₂ | benzyloxy | H |
| 285 | —H | 2-(1H-pyrrolyl) | —CH=CH₂ | benzyloxy | H |
| 286 | —H | 2-thiazolyl | —CH=CH₂ | benzyloxy | H |

TABLE 2-continued
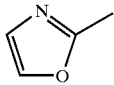
| Compound No | Z² | R¹ | R⁹ | R¹⁰ | R¹¹ |
|---|---|---|---|---|---|
| 287 | —H | 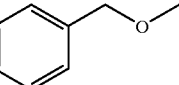 | —CH=CH₂ | 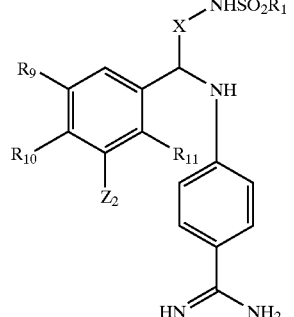 | H |
| 288 | —H | 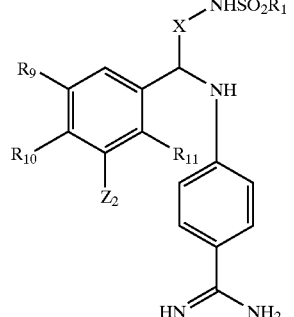 | —CH=CH₂ | 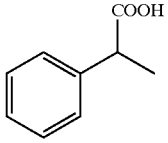 | H |
| 289 | —H | 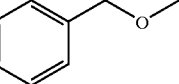 | —CH₂C≡CH | 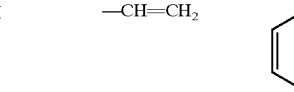 | H |
| 290 | —H | 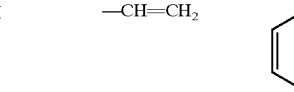 | —CH₂C≡CH | 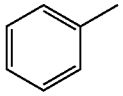 | H |
| 291 | —H | 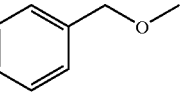 | —CH₂C≡CH | 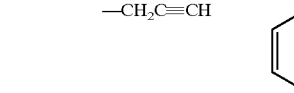 | H |
| 292 | —H | 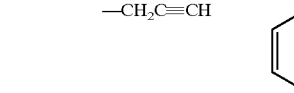 | —CH₂C≡CH | 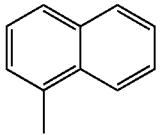 | H |
| 293 | —H | 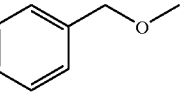 | —CH₂C≡CH | 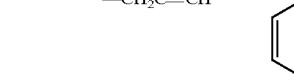 | H |
| 294 | —H | 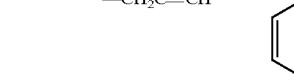 | —CH₂C≡CH | 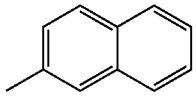 | H |
| 295 | —H | 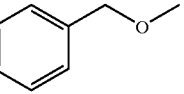 | —CH₂C≡CH | 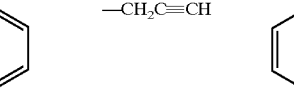 | H |

TABLE 2-continued
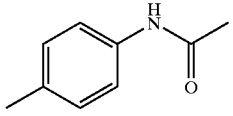
| Compound No | Z² | R¹ | R⁹ | R¹⁰ | R¹¹ |
|---|---|---|---|---|---|
| 296 | —H | 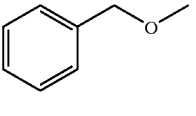 | —CH₂C≡CH | 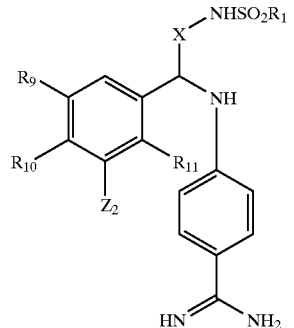 | H |
| 297 | —H | 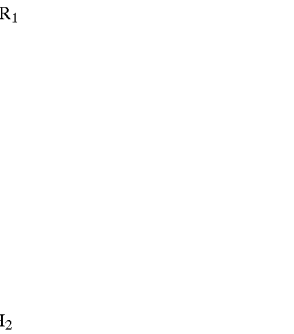 | —CH₂C≡CH | 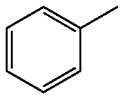 | 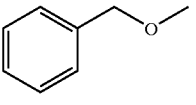 |
| 298 | —H | 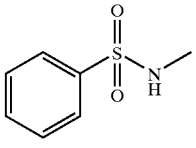 | —CH₂C≡CH | OCH₃ | Br |
| 299 | —H | 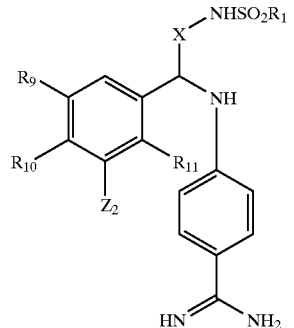 | —CH₂C≡CH | 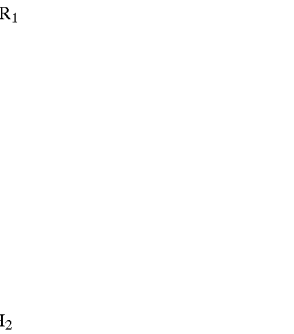 | H |
| 300 | —H | —CH(CH₃)₂ | —CH₂C≡CH | 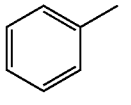 | H |
| 301 | —H | —CH₂CH₂CH₃ | —CH₂C≡CH | 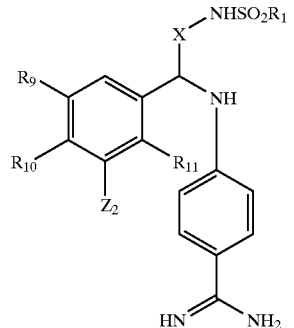 | CH₃SO₂—NH— |
| 302 | —H | 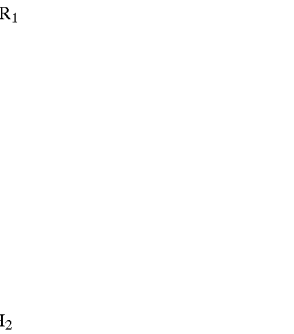 | —CH₂C≡CH | 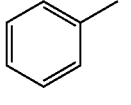 | H |
| 303 | —H | 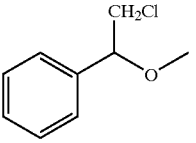 | —CH₂C≡CH | 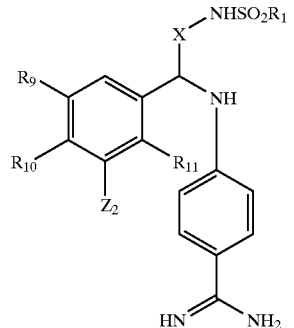 | H |
| 304 | —H | 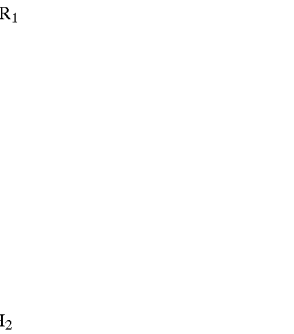 | —CH₂C≡CH | 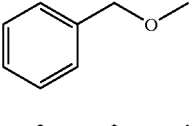 | H |

TABLE 2-continued
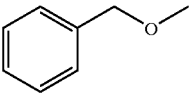
| Compound No | Z² | R¹ | R⁹ | R¹⁰ | R¹¹ |
|---|---|---|---|---|---|
| 305 | —H | —CH₂CH₃ | —CH₂C≡CH | 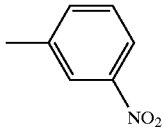 | H |
| 306 | —H | 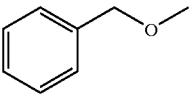 | —CH₂C≡CH | 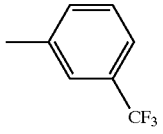 | H |
| 307 | —H | 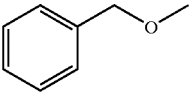 | —CH₂C≡CH | 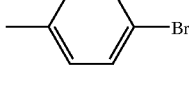 | H |
| 308 | —H | 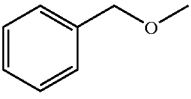 | —CH₂C≡CH | 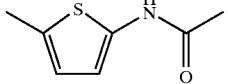 | H |
| 309 | —H | 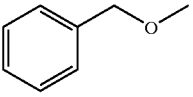 | —CH₂C≡CH | 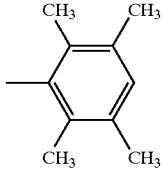 | H |
| 310 | —H | 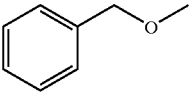 | —CH₂C≡CH | 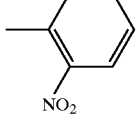 | H |
| 311 | —H | 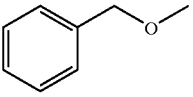 | —CH₂C≡CH | 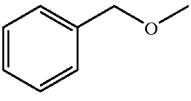 | H |
| 312 | —H | —CH₃ | —CH₂C≡CH |  | H |

TABLE 2-continued

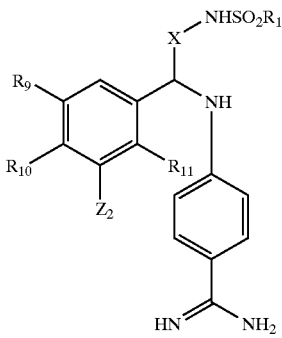

| Compound No | $Z^2$ | $R^1$ | $R^9$ | $R^{10}$ | $R^{11}$ |
|---|---|---|---|---|---|
| 313 | —H | 2-bromophenyl | —CH$_2$C≡CH | benzyloxymethyl | H |
| 314 | —H | 4-tert-butylphenyl | —CH$_2$C≡CH | benzyloxymethyl | H |
| 315 | —H | 2,4-dinitrophenyl | —CH$_2$C≡CH | benzyloxymethyl | H |
| 316 | —H | 3,4-dimethoxyphenyl | —CH$_2$C≡CH | benzyloxymethyl | H |
| 317 | —H | pentafluorophenyl | —CH$_2$C≡CH | benzyloxymethyl | H |
| 318 | —H | 4-carboxyphenyl | —CH$_2$C≡CH | benzyloxymethyl | H |
| 319 | —H | 3-carboxyphenyl | —CH$_2$C≡CH | benzyloxymethyl | H |
| 320 | —H | —CH$_2$CH$_2$CH$_3$ | —CH$_2$C≡CH | benzyloxymethyl | H |

TABLE 2-continued

| Compound No | Z² | R¹ | R⁹ | R¹⁰ | R¹¹ |
|---|---|---|---|---|---|
| 321 | —H | —CH₂CH₂CH₂CH₃ | —CH₂C≡CH | benzyloxymethyl (PhCH₂O-CH<) | H |
| 322 | —H | 4-isopropylphenyl | —CH₂C≡CH | benzyloxymethyl | H |
| 323 | —H | 2,4-dichloro-6-methyl-3-hydroxyphenyl | —CH₂C≡CH | benzyloxymethyl | H |
| 324 | —H | CH₂CH₂CH₃ | —CH₂C≡CH | 1-(chloromethyl)-1-methoxy-phenylmethyl | H |
| 325 | —H | —(CH₂)₆CH₃ | —CH₂C≡CH | benzyloxymethyl | H |
| 326 | —H | —CH=CH₂ | —CH₂C≡CH | benzyloxymethyl | H |
| 327 | —H | —CH₂—C≡CH | —CH₂C≡CH | benzyloxymethyl | H |
| 328 | —H | methylcyclohexyl | —CH₂C≡CH | benzyloxymethyl | H |
| 329 | —H | cyclopropyl | —CH₂C≡CH | benzyloxymethyl | H |

TABLE 2-continued

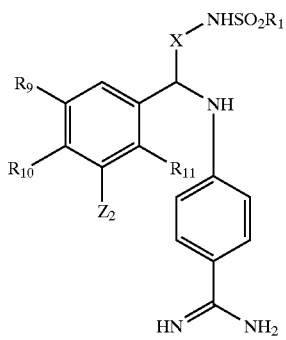

| Compound No | $Z^2$ | $R^1$ | $R^9$ | $R^{10}$ | $R^{11}$ |
|---|---|---|---|---|---|
| 330 | —H | 2-methylcycloheptyl | —CH$_2$C≡CH | benzyloxy | H |
| 331 | —H | 2-ethylnaphthyl | —CH$_2$C≡CH | benzyloxy | H |
| 332 | —H | 2-methylpyridyl | —CH$_2$C≡CH | benzyloxy | H |
| 333 | —H | 2-methylfuryl | —CH$_2$C≡CH | benzyloxy | H |
| 334 | —H | 2-methylimidazolyl | —CH$_2$C≡CH | benzyloxy | H |
| 335 | —H | 3-methylindolyl | —CH$_2$C≡CH | benzyloxy | H |
| 336 | —H | 3-methylisoindolyl | —CH$_2$C≡CH | benzyloxy | H |
| 337 | —H | 4-methylpyrimidinyl | —CH$_2$C≡CH | benzyloxy | H |
| 338 | —H | 3-methylpyrazinyl | —CH$_2$C≡CH | benzyloxy | H |

US 6,919,369 B2

TABLE 2-continued

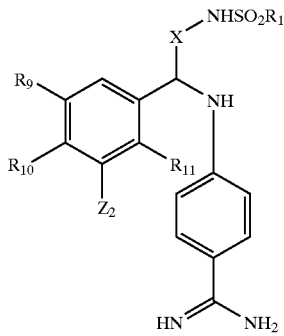

| Compound No | $Z^2$ | $R^1$ | $R^9$ | $R^{10}$ | $R^{11}$ |
|---|---|---|---|---|---|
| 339 | —H | 3-methylpyridazinyl | —CH$_2$C≡CH | benzyloxymethyl | H |
| 340 | —H | 2-methyl-1H-pyrrolyl | —CH$_2$C≡CH | benzyloxymethyl | H |
| 341 | —H | 2-methylthiazolyl | —CH$_2$C≡CH | benzyloxymethyl | H |
| 342 | —H | 2-methyloxazolyl | —CH$_2$C≡CH | benzyloxymethyl | H |
| 343 | —H | 2-phenylpropanoic acid | —CH$_2$C≡CH | benzyloxymethyl | H |
| 344 | —H | o-tolyl | OCH$_3$ | OCH$_3$ | H |
| 345 | —H | 1-methylnaphthyl | OCH$_3$ | OCH$_3$ | H |
| 346 | —H | 2-methylnaphthyl | OCH$_3$ | OCH$_3$ | H |
| 347 | —H | 5-dimethylamino-3-methylnaphthyl | OCH$_3$ | OCH$_3$ | H |

TABLE 2-continued

[Structure shown: a benzene ring with substituents R9, R10, R11, Z2, and a side chain —CH(NH-Ar-C(=NH)NH2)(X—NHSO2R1)]

| Compound No | Z² | R¹ | R⁹ | R¹⁰ | R¹¹ |
|---|---|---|---|---|---|
| 348 | —H | benzyl-CH2CH3 (phenethyl) | OCH₃ | OCH₃ | H |
| 349 | —H | cinnamyl (PhCH=CHCH2-) | OCH₃ | OCH₃ | H |
| 350 | —H | 2-thienylmethyl | OCH₃ | OCH₃ | H |
| 351 | —H | 4-(acetylamino)benzyl | OCH₃ | OCH₃ | H |
| 352 | —H | benzyl | OCH₃ | OCH₃ | C6H5-SO2-NH-CH3 (phenylsulfonyl-N-methylamide) |
| 353 | —H | benzyl | OCH₃ | OCH₃ | Br |
| 354 | —H | benzyl | OCH₃ | OCH₃ | H |
| 355 | —H | —CH(CH₃)₂ | OCH₃ | OCH₃ | H |
| 356 | —H | —CH₂CH₂CH₃ | OCH₃ | OCH₃ | CH₃SO₂—NH— |
| 357 | —H | 4-nitrobenzyl | OCH₃ | OCH₃ | H |
| 358 | —H | 4-fluorobenzyl | OCH₃ | OCH₃ | H |

TABLE 2-continued

| Compound No | $Z^2$ | $R^1$ | $R^9$ | $R^{10}$ | $R^{11}$ |
| --- | --- | --- | --- | --- | --- |
| 359 | —H | 2,5-dichlorophenyl | $OCH_3$ | $OCH_3$ | H |
| 360 | —H | —$CH_2CH_3$ | $OCH_3$ | $OCH_3$ | H |
| 361 | —H | 3-nitrophenyl | $OCH_3$ | $OCH_3$ | H |
| 362 | —H | 3-trifluoromethylphenyl | $OCH_3$ | $OCH_3$ | H |
| 363 | —H | 4-bromophenyl | $OCH_3$ | $OCH_3$ | H |
| 364 | —H | 5-methyl-2-acetamidothiophene | $OCH_3$ | $OCH_3$ | H |
| 365 | —H | 2,3,4,5-tetramethylphenyl | $OCH_3$ | $OCH_3$ | H |
| 366 | —H | 2-nitrophenyl | $OCH_3$ | $OCH_3$ | H |
| 367 | —H | —$CH_3$ | $OCH_3$ | $OCH_3$ | H |

TABLE 2-continued

[Structure: benzene ring with R9, R10, R11, Z2 substituents, connected via CH(X-NHSO2R1)-NH to a phenyl-amidine group]

| Compound No | Z² | R¹ | R⁹ | R¹⁰ | R¹¹ |
|---|---|---|---|---|---|
| 368 | —H | 2-bromophenyl | OCH₃ | OCH₃ | H |
| 369 | —H | 4-tert-butylphenyl | OCH₃ | OCH₃ | H |
| 370 | —H | 2,4-dinitrophenyl | OCH₃ | OCH₃ | H |
| 371 | —H | 3,4-dimethoxyphenyl | OCH₃ | OCH₃ | H |
| 372 | —H | pentafluorophenyl | OCH₃ | OCH₃ | H |
| 373 | —H | 4-carboxyphenyl | OCH₃ | OCH₃ | H |
| 374 | —H | 3-carboxyphenyl | OCH₃ | OCH₃ | H |
| 375 | —H | —CH₂CH₂CH₃ | OCH₃ | OCH₃ | H |
| 376 | —H | —CH₂CH₂CH₂CH₃ | OCH₃ | OCH₃ | H |
| 377 | —H | 4-(1-methylethyl)phenyl (chiral) | OCH₃ | OCH₃ | H |

TABLE 2-continued

| Compound No | $Z^2$ | $R^1$ | $R^9$ | $R^{10}$ | $R^{11}$ |
|---|---|---|---|---|---|
| 378 | —H | 2-methyl-4,6-dichlorophenol | $OCH_3$ | $OCH_3$ | H |
| 379 | —H | —$CH_2CH_2CH_3$ | $OCH_3$ | $OCH_3$ | H |
| 380 | —H | —$(CH_2)_6CH_3$ | $OCH_3$ | $OCH_3$ | H |
| 381 | —H | —CH=$CH_2$ | $OCH_3$ | $OCH_3$ | H |
| 382 | —H | —$CH_2$C≡CH | $OCH_3$ | $OCH_3$ | H |
| 383 | —H | cyclohexyl | $OCH_3$ | $OCH_3$ | H |
| 384 | —H | cyclopropyl | $OCH_3$ | $OCH_3$ | H |
| 385 | —H | cycloheptyl | $OCH_3$ | $OCH_3$ | H |
| 386 | —H | naphthyl-ethyl | $OCH_3$ | $OCH_3$ | H |
| 387 | —H | 2-pyridyl | $OCH_3$ | $OCH_3$ | H |
| 388 | —H | 2-furyl | $OCH_3$ | $OCH_3$ | H |
| 389 | —H | 2-imidazolyl | $OCH_3$ | $OCH_3$ | H |

TABLE 2-continued

| Compound No | $Z^2$ | $R^1$ | $R^9$ | $R^{10}$ | $R^{11}$ |
|---|---|---|---|---|---|
| 390 | —H | 3-methylindole | $OCH_3$ | $OCH_3$ | H |
| 391 | —H | 3-methylisoindole | $OCH_3$ | $OCH_3$ | H |
| 392 | —H | 4-methylpyrimidine | $OCH_3$ | $OCH_3$ | H |
| 393 | —H | 2-methylpyrazine | $OCH_3$ | $OCH_3$ | H |
| 394 | —H | 3-methylpyridazine | $OCH_3$ | $OCH_3$ | H |
| 395 | —H | 2-methylpyrrole | $OCH_3$ | $OCH_3$ | H |
| 396 | —H | 2-methylthiazole | $OCH_3$ | $OCH_3$ | H |
| 397 | —H | 2-methyloxazole | $OCH_3$ | $OCH_3$ | H |
| 398 | —H | 2-phenylpropanoic acid | $OCH_3$ | $OCH_3$ | H |

TABLE 2-continued

| Compound No | $Z^2$ | $R^1$ | $R^9$ | $R^{10}$ | $R^{11}$ |
|---|---|---|---|---|---|
| 399 | —H | phenyl | $OCH_3$ | $OCH_2CH_3$ | H |
| 400 | —H | naphthalen-1-yl | $OCH_3$ | $OCH_2CH_3$ | H |
| 401 | —H | naphthalen-2-yl | $OCH_3$ | $OCH_2CH_3$ | H |
| 402 | —H | 5-(dimethylamino)naphthalen-2-yl | $OCH_3$ | $OCH_2CH_3$ | H |
| 403 | —H | benzyl | $OCH_3$ | $OCH_2CH_3$ | H |
| 404 | —H | (E)-styryl | $OCH_3$ | $OCH_2CH_3$ | H |
| 405 | —H | thiophen-2-yl | $OCH_3$ | $OCH_2CH_3$ | H |
| 406 | —H | 4-acetamidophenyl | $OCH_3$ | $OCH_2CH_3$ | H |
| 407 | —H | phenyl | $OCH_3$ | $OCH_2CH_3$ | $C_6H_5SO_2NH$— |

TABLE 2-continued

[Structure: substituted benzene with R9, R10, R11, Z2 substituents, bearing a CH(X-NHSO2R1)(NH-aryl-C(=NH)NH2) group]

| Compound No | Z² | R¹ | R⁹ | R¹⁰ | R¹¹ |
|---|---|---|---|---|---|
| 408 | —H | phenyl | OCH₃ | OCH₂CH₃ | Br |
| 409 | —H | phenyl | OCH₃ | OCH₂CH₃ | H |
| 410 | —H | —CH(CH₃)₂ | OCH₃ | OCH₂CH₃ | H |
| 411 | —H | —CH₂CH₂CH₃ | OCH₃ | OCH₂CH₃ | CH₃SO₂—NH— |
| 412 | —H | 4-NO₂-phenyl | OCH₃ | OCH₂CH₃ | H |
| 413 | —H | 4-F-phenyl | OCH₃ | OCH₂CH₃ | H |
| 414 | —H | 2,5-dichlorophenyl | OCH₃ | OCH₂CH₃ | H |
| 415 | —H | —CH₂CH₃ | OCH₃ | OCH₂CH₃ | H |
| 416 | —H | 3-NO₂-phenyl | OCH₃ | OCH₂CH₃ | H |
| 417 | —H | 3-CF₃-phenyl | OCH₃ | OCH₂CH₃ | H |
| 418 | —H | 4-Br-phenyl | OCH₃ | OCH₂CH₃ | H |

TABLE 2-continued
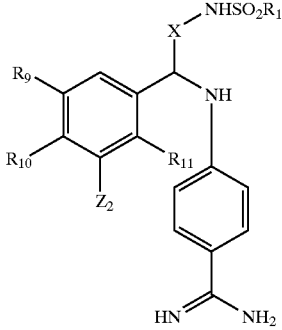
| Compound No | $Z^2$ | $R^1$ | $R^9$ | $R^{10}$ | $R^{11}$ |
|---|---|---|---|---|---|
| 419 | —H | 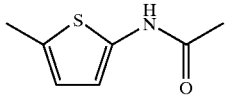 | $OCH_3$ | $OCH_2CH_3$ | H |
| 420 | —H | 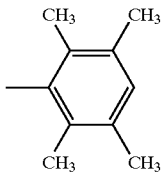 | $OCH_3$ | $OCH_2CH_3$ | H |
| 421 | —H | 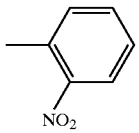 | $OCH_3$ | $OCH_2CH_3$ | H |
| 422 | —H | —$CH_3$ | $OCH_3$ | $OCH_2CH_3$ | H |
| 423 | —H | 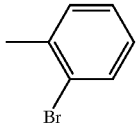 | $OCH_3$ | $OCH_2CH_3$ | H |
| 424 | —H | 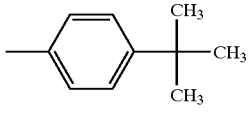 | $OCH_3$ | $OCH_2CH_3$ | H |
| 425 | —H | 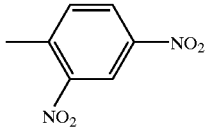 | $OCH_3$ | $OCH_2CH_3$ | H |
| 426 | —H | 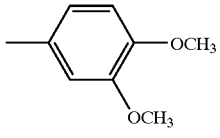 | $OCH_3$ | $OCH_2CH_3$ | H |

TABLE 2-continued

| Compound No | $Z^2$ | $R^1$ | $R^9$ | $R^{10}$ | $R^{11}$ |
|---|---|---|---|---|---|
| 427 | —H | pentafluorophenyl | $OCH_3$ | $OCH_2CH_3$ | H |
| 428 | —H | 4-carboxyphenyl | $OCH_3$ | $OCH_2CH_3$ | H |
| 429 | —H | 3-carboxyphenyl | $OCH_3$ | $OCH_2CH_3$ | H |
| 430 | —H | —$CH_2CH_2CH_3$ | $OCH_3$ | $OCH_2CH_3$ | H |
| 431 | —H | —$CH_2CH_2CH_2CH_3$ | $OCH_3$ | $OCH_2CH_3$ | H |
| 432 | —H | 4-isopropylphenyl | $OCH_3$ | $OCH_2CH_3$ | H |
| 433 | —H | 3,5-dichloro-4-hydroxyphenyl | $OCH_3$ | $OCH_2CH_3$ | H |
| 434 | —H | —$CH_2CH_2CH_3$ | $OCH_3$ | $OCH_2CH_3$ | H |
| 435 | —H | —$(CH_2)_6CH_3$ | $OCH_3$ | $OCH_2CH_3$ | H |
| 436 | —H | —$CH=CH_2$ | $OCH_3$ | $OCH_2CH_3$ | H |
| 437 | —H | —$CH_2$—$C{\equiv}CH$ | $OCH_3$ | $OCH_2CH_3$ | H |
| 438 | —H | cyclohexyl | $OCH_3$ | $OCH_2CH_3$ | H |
| 439 | —H | cyclopropyl | $OCH_3$ | $OCH_2CH_3$ | H |

TABLE 2-continued

[Structure: substituted benzene with R9, R10, R11, Z2 substituents; CH(X-NHSO2R1)(NH-phenyl-C(=NH)NH2)]

| Compound No | Z² | R¹ | R⁹ | R¹⁰ | R¹¹ |
|---|---|---|---|---|---|
| 440 | —H | 1-methylcycloheptyl (with H) | OCH₃ | OCH₂CH₃ | H |
| 441 | —H | 2-ethylnaphthyl | OCH₃ | OCH₂CH₃ | H |
| 442 | —H | 2-methylpyridyl | OCH₃ | OCH₂CH₃ | H |
| 443 | —H | 2-methylfuryl | OCH₃ | OCH₂CH₃ | H |
| 444 | —H | 2-methylimidazolyl | OCH₃ | OCH₂CH₃ | H |
| 445 | —H | 3-methylindolyl | OCH₃ | OCH₂CH₃ | H |
| 446 | —H | 3-methylisoindolyl | OCH₃ | OCH₂CH₃ | H |
| 447 | —H | 4-methylpyrimidinyl | OCH₃ | OCH₂CH₃ | H |
| 448 | —H | 3-methylpyrazinyl | OCH₃ | OCH₂CH₃ | H |

TABLE 2-continued
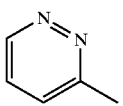
| Compound No | $Z^2$ | $R^1$ | $R^9$ | $R^{10}$ | $R^{11}$ |
|---|---|---|---|---|---|
| 449 | —H | 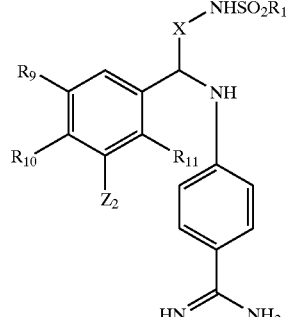 | $OCH_3$ | $OCH_2CH_3$ | H |
| 450 | —H | 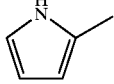 | $OCH_3$ | $OCH_2CH_3$ | H |
| 451 | —H | 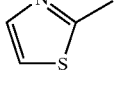 | $OCH_3$ | $OCH_2CH_3$ | H |
| 452 | —H | 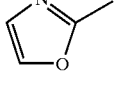 | $OCH_3$ | $OCH_2CH_3$ | H |
| 453 | —H | 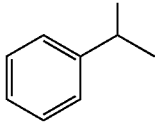 | $OCH_3$ | $OCH_2CH_3$ | H |
| 454 | —H | 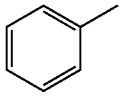 | $OCH_3$ | OH | H |
| 455 | —H | 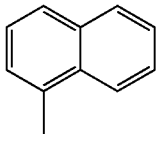 | $OCH_3$ | OH | H |
| 456 | —H | 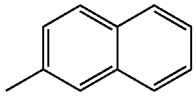 | $OCH_3$ | OH | H |
| 457 | —H | 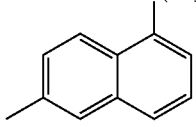 | $OCH_3$ | OH | H |

TABLE 2-continued

[Structure: A benzene ring with substituents R9, R10, R11, Z2, and a CH(NH-)(X-NHSO2R1) group attached, where NH connects to a phenyl-C(=NH)NH2 (benzamidine) group]

| Compound No | Z² | R¹ | R⁹ | R¹⁰ | R¹¹ |
|---|---|---|---|---|---|
| 458 | —H | benzyl (CH2-C6H5) | OCH₃ | OH | H |
| 459 | —H | cinnamyl (CH=CH-CH2 attached to phenyl) / (E)-propenyl-phenyl | OCH₃ | OH | H |
| 460 | —H | 2-thienylmethyl | OCH₃ | OH | H |
| 461 | —H | 4-(acetylamino)benzyl | OCH₃ | OH | H |
| 462 | —H | benzyl | OCH₃ | OH | C6H5-SO2-NH- (N-methyl phenylsulfonamido) |
| 463 | —H | benzyl | OCH₃ | OH | Br |
| 464 | —H | benzyl | OCH₃ | OH | H |
| 465 | —H | —CH(CH₃)₂ | OCH₃ | OH | H |
| 466 | —H | —CH₂CH₂CH₃ | OCH₃ | OH | CH₃SO₂—NH— |
| 467 | —H | 4-nitrobenzyl | OCH₃ | OH | H |
| 468 | —H | 4-fluorobenzyl | OCH₃ | OH | H |

TABLE 2-continued
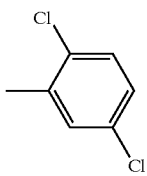
| Compound No | Z² | R¹ | R⁹ | R¹⁰ | R¹¹ |
|---|---|---|---|---|---|
| 469 | —H | 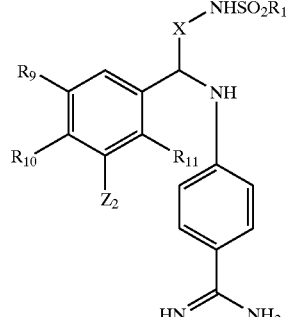 | OCH₃ | OH | H |
| 470 | —H | —CH₂CH₃ | OCH₃ | OH | H |
| 471 | —H | 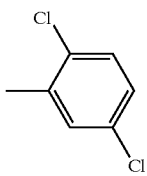 | OCH₃ | OH | H |
| 472 | —H | 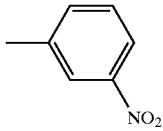 | OCH₃ | OH | H |
| 473 | —H | 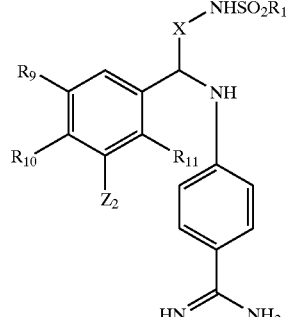 | OCH₃ | OH | H |
| 474 | —H | 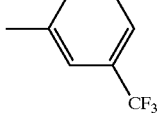 | OCH₃ | OH | H |
| 475 | —H | 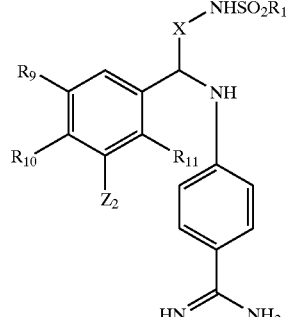 | OCH₃ | OH | H |
| 476 | —H | 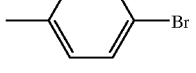 | OCH₃ | OH | H |
| 477 | —H | 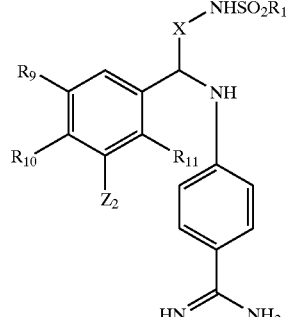 | OCH₃ | OH | H |

TABLE 2-continued
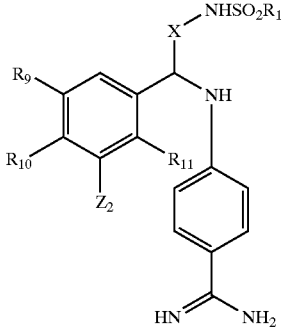
| Compound No | $Z^2$ | $R^1$ | $R^9$ | $R^{10}$ | $R^{11}$ |
|---|---|---|---|---|---|
| 478 | —H | 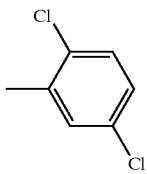 | OCH$_3$ | OH | H |
| 479 | —H | —CH$_2$CH$_3$ | OCH$_3$ | OH | H |
| 480 | —H | 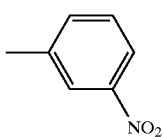 | OCH$_3$ | OH | H |
| 481 | —H | 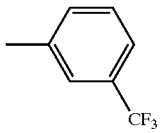 | OCH$_3$ | OH | H |
| 482 | —H | 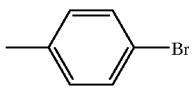 | OCH$_3$ | OH | H |
| 483 | —H | 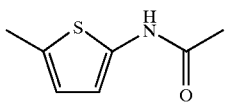 | OCH$_3$ | OH | H |
| 484 | —H | 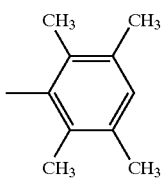 | OCH$_3$ | OH | H |
| 485 | —H | 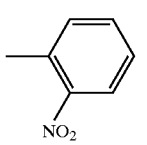 | OCH$_3$ | OH | H |
| 486 | —H | —CH$_3$ | OCH$_3$ | OH | H |

TABLE 2-continued
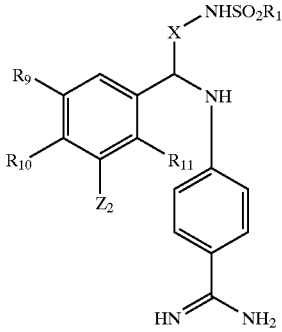
| Compound No | Z² | R¹ | R⁹ | R¹⁰ | R¹¹ |
|---|---|---|---|---|---|
| 487 | —H |  | OCH₃ | OH | H |
| 488 | —H | 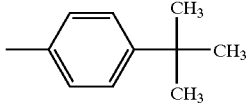 | OCH₃ | OH | H |
| 489 | —H | 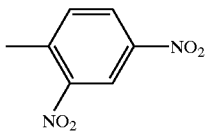 | OCH₃ | OH | H |
| 490 | —H | 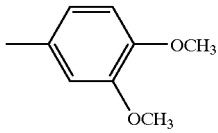 | OCH₃ | OH | H |
| 491 | —H | 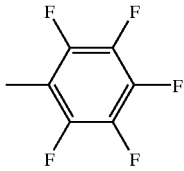 | OCH₃ | OH | H |
| 492 | —H | 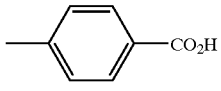 | OCH₃ | OH | H |
| 493 | —H | 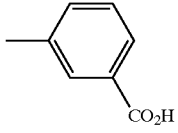 | OCH₃ | OH | H |
| 494 | —H | —CH₂CH₂CH₃ | OCH₃ | OH | H |
| 495 | —H | —CH₂CH₂CH₂CH₃ | OCH₃ | OH | H |
| 496 | —H | 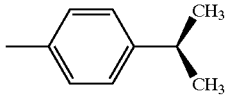 | OCH₃ | OH | H |

TABLE 2-continued

[Structure: substituted benzene with R9, R10, R11, Z2 substituents; CH group bearing X-NHSO2R1 and NH linked to para-amidinophenyl (HN=C(NH2)-)]

| Compound No | Z² | R¹ | R⁹ | R¹⁰ | R¹¹ |
|---|---|---|---|---|---|
| 497 | —H | 2,4-dichloro-6-methylphenol (Cl, Cl, CH3, OH-substituted phenyl) | OCH₃ | OH | H |
| 498 | —H | —CH₂CH₂CH₃ | OCH₃ | OH | H |
| 499 | —H | —(CH₂)₆CH₃ | OCH₃ | OH | H |
| 500 | —H | —CH=CH₂ | OCH₃ | OH | H |
| 501 | —H | —CH₂—C≡CH | OCH₃ | OH | H |
| 502 | —H | cyclohexyl | OCH₃ | OH | H |
| 503 | —H | cyclopropyl | OCH₃ | OH | H |
| 504 | —H | cycloheptyl | OCH₃ | OH | H |
| 505 | —H | 2-naphthyl | OCH₃ | OH | H |
| 506 | —H | 2-pyridyl | OCH₃ | OH | H |
| 507 | —H | 2-furyl | OCH₃ | OH | H |
| 508 | —H | 2-imidazolyl | OCH₃ | OH | H |

TABLE 2-continued
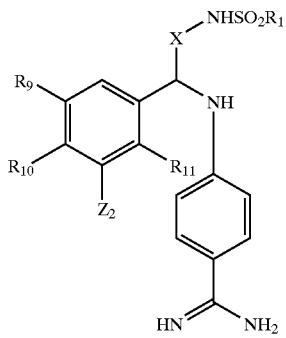
| Compound No | $Z^2$ | $R^1$ | $R^9$ | $R^{10}$ | $R^{11}$ |
|---|---|---|---|---|---|
| 509 | —H | 3-methylindol-2-yl | $OCH_3$ | OH | H |
| 510 | —H | 3-methylisoindol-1-yl | $OCH_3$ | OH | H |
| 511 | —H | 4-methylpyrimidin-2-yl | $OCH_3$ | OH | H |
| 512 | —H | 3-methylpyrazin-2-yl | $OCH_3$ | OH | H |
| 513 | —H | 3-methylpyridazin-6-yl | $OCH_3$ | OH | H |
| 514 | —H | 2-methylpyrrol-1-yl | $OCH_3$ | OH | H |
| 515 | —H | 2-methylthiazol-2-yl | $OCH_3$ | OH | H |
| 516 | —H | 2-methylimidazol-2-yl | $OCH_3$ | OH | H |
| 517 | —H | α-methylphenylacetic acid | $OCH_3$ | OH | H |

TABLE 2-continued
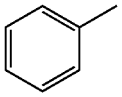
| Compound No | $Z^2$ | $R^1$ | $R^9$ | $R^{10}$ | $R^{11}$ |
|---|---|---|---|---|---|
| 518 | —H | 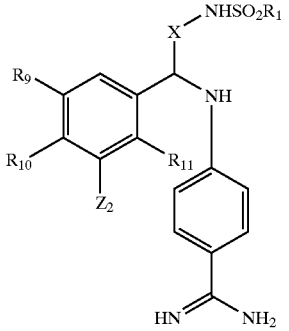 | $OCH_3$ | OH | $CH_3CH_2SO_2NH—$ |
| 519 | —H |  | $OCH_3$ | OH | $CH_3(CH_2)_2SO_2NH—$ |
| 520 | —H | 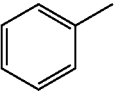 | $OCH_3$ | OH | $CH_3(CH_2)_3SO_2NH—$ |
| 521 | —H | 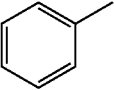 | $OCH_3$ | OH | $(CH_3)_3CSO_2NH—$ |
| 522 | —H | 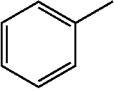 | $OCH_3$ | OH | $(CH_3)_2CHSO_2NH—$ |
| 523 | —H | 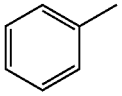 | $OCH_3$ | OH | 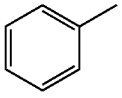—$SO_2NH—$ |
| 524 | —H | 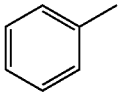 | $OCH_3$ | $OCH_3$ | $CH_3CH_2SO_2NH—$ |
| 525 | —H | 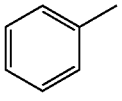 | $OCH_3$ | $OCH_3$ | $CH_3(CH_2)_2SO_2NH—$ |
| 526 | —H | 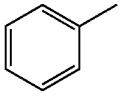 | $OCH_3$ | $OCH_3$ | $CH_3(CH_2)_3SO_2NH—$ |
| 527 | —H | 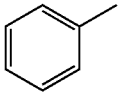 | $OCH_3$ | $OCH_3$ | $(CH_3)_3CSO_2NH—$ |

TABLE 2-continued

| Compound No | $Z^2$ | $R^1$ | $R^9$ | $R^{10}$ | $R^{11}$ |
|---|---|---|---|---|---|
| 528 | —H | phenyl | $OCH_3$ | $OCH_3$ | $(CH_3)_2CHSO_2NH—$ |
| 529 | —H | phenyl | $OCH_3$ | $OCH_3$ | cyclopropyl-$SO_2NH—$ |
| 530 | —H | phenyl | $OCH_3$ | $OCH_2CH_3$ | $CH_3CH_2SO_2NH—$ |
| 531 | —H | phenyl | $OCH_3$ | $OCH_2CH_3$ | $CH_3(CH_2)_2SO_2NH—$ |
| 532 | —H | phenyl | $OCH_3$ | $OCH_2CH_3$ | $CH_3(CH_2)_3SO_2NH—$ |
| 533 | —H | phenyl | $OCH_3$ | $OCH_2CH_3$ | $(CH_3)_3CSO_2NH—$ |
| 534 | —H | phenyl | $OCH_3$ | $OCH_2CH_3$ | $(CH_3)_2CHSO_2NH—$ |
| 535 | —H | phenyl | $OCH_3$ | $OCH_2CH_3$ | cyclopropyl-$SO_2NH—$ |
| 536 | —H | phenyl-CH(CH$_3$)COOH | $OCH_3$ | OH | $CH_3CH_2SO_2NH—$ |

TABLE 2-continued
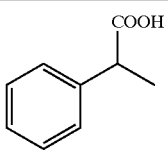
| Compound No | $Z^2$ | $R^1$ | $R^9$ | $R^{10}$ | $R^{11}$ |
|---|---|---|---|---|---|
| 537 | —H | 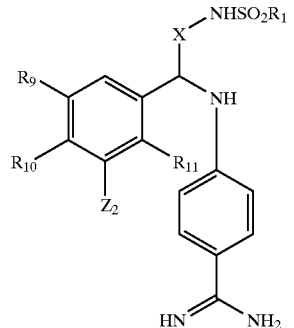 | $OCH_3$ | OH | $CH_3(CH_2)_2SO_2NH$— |
| 538 | —H | 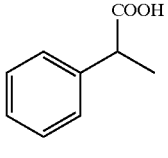 | $OCH_3$ | OH | $CH_3(CH_2)_3SO_2NH$— |
| 539 | —H | 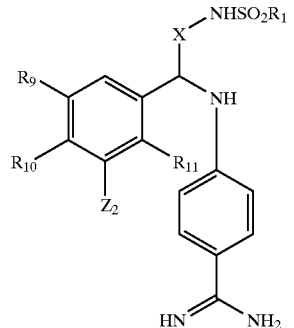 | $OCH_3$ | OH | $(CH_3)_3CSO_2NH$— |
| 540 | —H | 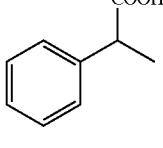 | $OCH_3$ | OH | $(CH_3)_2CHSO_2NH$— |
| 541 | —H | 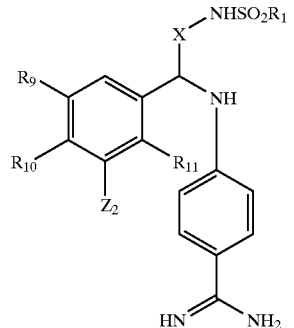 | $OCH_3$ | OH | 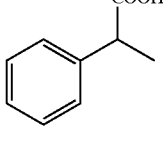 |
| 542 | —H | —$CH_2CH_2CH_3$ | —$OCH_2CH_3$ | —$OCH_2CH_3$ | —$OCH_2CO_2H$ |
| 543 | —H | —$CH_2CH_2CH_3$ | —$OCH_2CH_3$ | —$OCH_2Ph$ | —$OCH_2CO_2H$ |
| 544 | —H | 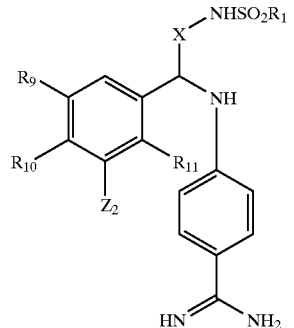 | —$OCH_2CH_3$ | —$OCH_2CH_3$ | —$OCH_2CO_2H$ |
| 545 | —H | 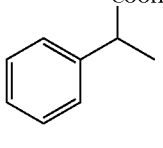 | —$OCH_2CH_3$ | —$OCH_2Ph$ | —$OCH_2CO_2H$ |
| 546 | —H | 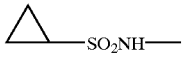 | —$OCH_2CH_3$ | —$OCH_2Ph$ | —$OCH_2CO_2H$ |

TABLE 2-continued

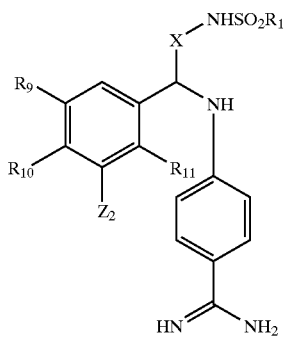

| Compound No | $Z^2$ | $R^1$ | $R^9$ | $R^{10}$ | $R^{11}$ |
|---|---|---|---|---|---|
| 547 | —H | 2-thienyl | —OCH$_2$CH$_3$ | —OCH$_2$CH$_3$ | —OCH$_2$CO$_2$H |
| 548 | —H | -n-Butyl | —OCH$_2$CH$_3$ | —OCH$_2$CH$_3$ | —OCH$_2$CO$_2$H |
| 549 | —H | -isopropyl | —OCH$_2$CH$_3$ | —OCH$_2$CH$_3$ | —OCH$_2$CO$_2$H |
| 550 | —H | -isobutyl | —OCH$_2$CH$_3$ | —OCH$_2$CH$_3$ | —OCH$_2$CO$_2$H |
| 551 | —H | -sec-butyl | —OCH$_2$CH$_3$ | —OCH$_2$CH$_3$ | —OCH$_2$CO$_2$H |
| 552 | —H | —CH$_2$CH$_2$Cl | —OCH$_2$CH$_3$ | —OCH$_2$CH$_3$ | —OCH$_2$CO$_2$H |
| 553 | —H | —CH$_2$CH$_2$CH$_2$Cl | —OCH$_2$CH$_3$ | —OCH$_2$CH$_3$ | —OCH$_2$CO$_2$H |
| 554 | —H | —CH$_2$CH$_2$CH$_3$ | —OCH$_2$CH$_3$ | —OCH$_2$CH$_3$ | —N(SO$_2$CH$_3$)CH$_2$CO$_2$H |
| 555 | —H | —CH$_2$CH$_2$CH$_3$ | —OCH$_2$CH$_3$ | —OCH$_2$Ph | —N(SO$_2$CH$_3$)CH$_2$CO$_2$Et |
| 556 | —H | phenyl | —OCH$_2$CH$_3$ | —OCH$_2$CH$_3$ | —N(SO$_2$CH$_3$)CH$_2$CO$_2$H |
| 557 | —H | phenyl | —OCH$_2$CH$_3$ | —OCH$_2$Ph | —N(SO$_2$CH$_3$)CH$_2$CO$_2$Et |
| 558 | —H | 2-thienyl | —OCH$_2$CH$_3$ | —OCH$_2$Ph | —N(SO$_2$CH$_3$)CH$_2$CO$_2$H |
| 559 | —H | 2-thienyl | —OCH$_2$CH$_3$ | —OCH$_2$CH$_3$ | —N(SO$_2$CH$_3$)CH$_2$CO$_2$H |
| 560 | —H | -n-Butyl | —OCH$_2$CH$_3$ | —OCH$_2$CH$_3$ | —N(SO$_2$CH$_3$)CH$_2$CO$_2$H |
| 561 | —H | -isopropyl | —OCH$_2$CH$_3$ | —OCH$_2$CH$_3$ | —N(SO$_2$CH$_3$)CH$_2$CO$_2$H |
| 562 | —H | -isobutyl | —OCH$_2$CH$_3$ | —OCH$_2$CH$_3$ | —N(SO$_2$CH$_3$)CH$_2$CO$_2$H |

TABLE 2-continued

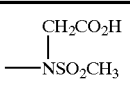

| Compound No | $Z^2$ | $R^1$ | $R^9$ | $R^{10}$ | $R^{11}$ |
|---|---|---|---|---|---|
| 563 | —H | -sec-butyl | —OCH$_2$CH$_3$ | —OCH$_2$CH$_3$ | 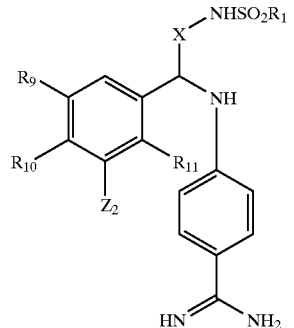 |
| 564 | —H | —CH$_2$CH$_2$Cl | —OCH$_2$CH$_3$ | —OCH$_2$CH$_3$ | 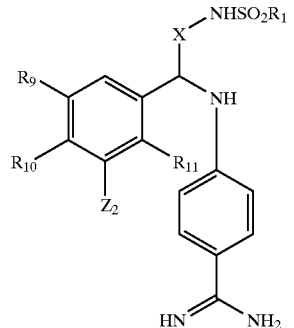 |
| 565 | —H | —CH$_2$CH$_2$CH$_2$Cl | —OCH$_2$CH$_3$ | —OCH$_2$CH$_3$ | 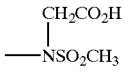 |
| 566 | —H | —CH$_2$CH$_2$CH$_3$ | —OCH$_2$CH$_3$ | —OCH(CH$_3$)$_2$ | —NHSO$_2$CH$_3$ |
| 567 | —H | 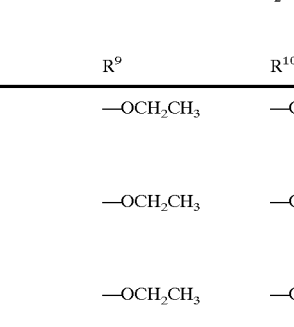 | —OCH$_2$CH$_3$ | —OCH(CH$_3$)$_2$ | —NHSO$_2$CH$_3$ |
| 568 | —H | 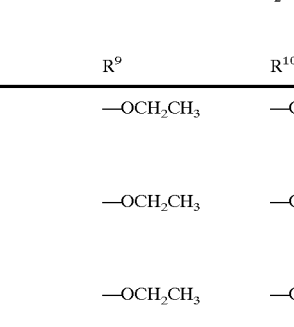 | —OCH$_2$CH$_3$ | —OCH(CH$_3$)$_2$ | —NHSO$_2$CH$_3$ |
| 569 | —H | -n-Butyl | —OCH$_2$CH$_3$ | —OCH(CH$_3$)$_2$ | —NHSO$_2$CH$_3$ |
| 570 | —H | -isopropyl | —OCH$_2$CH$_3$ | —OCH(CH$_3$)$_2$ | —NHSO$_2$CH$_3$ |
| 571 | —H | -isobutyl | —OCH$_2$CH$_3$ | —OCH(CH$_3$)$_2$ | —NHSO$_2$CH$_3$ |
| 572 | —H | -sec-butyl | —OCH$_2$CH$_3$ | —OCH(CH$_3$)$_2$ | —NHSO$_2$CH$_3$ |
| 573 | —H | —CH$_2$CH$_2$Cl | —OCH$_2$CH$_3$ | —OCH(CH$_3$)$_2$ | —NHSO$_2$CH$_3$ |
| 574 | —H | —CH$_2$CH$_2$CH$_2$Cl | —OCH$_2$CH$_3$ | —OCH(CH$_3$)$_2$ | —NHSO$_2$CH$_3$ |
| 575 | —H | —CH$_2$CH$_2$CH$_3$ | —OCH$_2$CH$_3$ | —OCH(CH$_3$)Et | —NHSO$_2$CH$_3$ |
| 576 | —H | -isobutyl | —OCH$_2$CH$_3$ | —OCH(CH$_3$)Et | —NHSO$_2$CH$_3$ |
| 577 | —H | -sec-butyl | —OCH$_2$CH$_3$ | —OCH(CH$_3$)Et | —NHSO$_2$CH$_3$ |
| 578 | —H | —CH$_2$CH$_2$CH$_3$ | —OCH$_2$CH$_3$ | —OCH$_2$CH$_3$ | 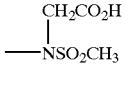 |
| 579 | —H | —CH$_2$CH$_2$CH$_3$ | —OCH$_2$CH$_3$ | —OCH$_2$Ph | 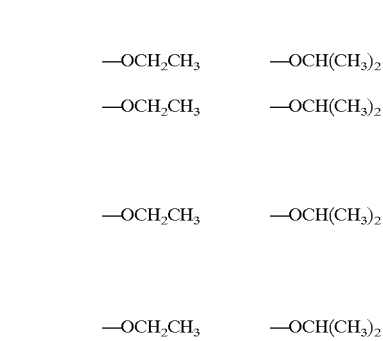 |

TABLE 2-continued

| Compound No | Z² | R¹ | R⁹ | R¹⁰ | R¹¹ |
|---|---|---|---|---|---|
| 580 | —H | phenyl | —OCH₂CH₃ | —OCH₂CH₃ | isothiazolidine 1,1-dioxide |
| 581 | —H | phenyl | —OCH₂CH₃ | —OCH₂Ph | isothiazolidine 1,1-dioxide |
| 582 | —H | 2-thienyl | —OCH₂CH₃ | —OCH₂Ph | isothiazolidine 1,1-dioxide |
| 583 | —H | 2-thienyl | —OCH₂CH₃ | —OCH₂CH₃ | isothiazolidine 1,1-dioxide |
| 584 | —H | n-Butyl | —OCH₂CH₃ | —OCH₂CH₃ | isothiazolidine 1,1-dioxide |
| 585 | —H | -isobutyl | —OCH₂CH₃ | —OCH₂CH₃ | isothiazolidine 1,1-dioxide |
| 586 | —H | -sec-butyl | —OCH₂CH₃ | —OCH₂CH₃ | isothiazolidine 1,1-dioxide |
| 587 | —H | —CH₂CH₂Cl | —OCH₂CH₃ | —OCH₂CH₃ | isothiazolidine 1,1-dioxide |

TABLE 2-continued

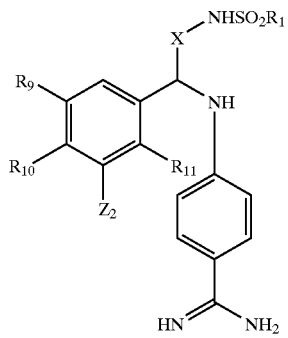

| Compound No | $Z^2$ | $R^1$ | $R^9$ | $R^{10}$ | $R^{11}$ |
|---|---|---|---|---|---|
| 588 | —H | —CH$_2$CH$_2$CH$_2$Cl | —OCH$_2$CH$_3$ | —OCH$_2$CH$_3$ | (N-isothiazolidine 1,1-dioxide) |
| 589 | —H | —CH$_2$CH$_2$CH$_3$ | —OCH$_2$CH$_3$ | —OCH$_2$CH$_3$ | —NHSO$_2$CH$_2$CO$_2$Et |
| 590 | —H | —CH$_2$CH$_2$CH$_3$ | —OCH$_2$CH$_3$ | —OCH$_2$Ph | —NHSO$_2$CH$_2$CO$_2$Et |
| 591 | —H | phenyl | —OCH$_2$CH$_3$ | —OCH$_2$CH$_3$ | —NHSO$_2$CH$_2$CO$_2$H |
| 592 | —H | phenyl | —OCH$_2$CH$_3$ | —OCH$_2$Ph | —NHSO$_2$CH$_2$CO$_2$Et |
| 593 | —H | 2-thienyl | —OCH$_2$CH$_3$ | —OCH$_2$Ph | —NHSO$_2$CH$_2$CO$_2$H |
| 594 | —H | 2-thienyl | —OCH$_2$CH$_3$ | —OCH$_2$CH$_3$ | —NHSO$_2$CH$_2$CO$_2$Et |
| 595 | —H | -n-Butyl | —OCH$_2$CH$_3$ | —OCH$_2$CH$_3$ | —NHSO$_2$CH$_2$CO$_2$Et |
| 596 | —H | -propyl | —OCH$_2$CH$_3$ | —OCH$_2$CH$_3$ | —NHSO$_2$CH$_2$CO$_2$H |
| 597 | —H | -isobutyl | —OCH$_2$CH$_3$ | —OCH$_2$CH$_3$ | —NHSO$_2$CH$_2$CO$_2$Et |
| 598 | —H | -sec-butyl | —OCH$_2$CH$_3$ | —OCH$_2$CH$_3$ | —NHSO$_2$CH$_2$CO$_2$Et |
| 599 | —H | —CH$_2$CH$_2$Cl | —OCH$_2$CH$_3$ | —OCH$_2$CH$_3$ | —NHSO$_2$CH$_2$CO$_2$Et |
| 600 | —H | —CH$_2$CH$_2$CH$_2$Cl | —OCH$_2$CH$_3$ | —OCH$_2$CH$_3$ | —NHSO$_2$CH$_2$CO$_2$Et |
| 601 | —H | —CH$_2$CH$_2$CH$_3$ | —OCH$_2$CH$_3$ | —OCH$_2$CH$_3$ | —N CH$_3$SO$_2$CH$_3$ |
| 602 | —H | —CH$_2$CH$_2$CH$_3$ | —OCH$_2$CH$_3$ | —OCH$_2$Ph | —N CH$_3$SO$_2$CH$_3$ |
| 603 | —H | phenyl | —OCH$_2$CH$_3$ | —OCH$_2$CH$_3$ | —N CH$_3$SO$_2$CH$_3$ |
| 604 | —H | phenyl | —OCH$_2$CH$_3$ | —OCH$_2$Ph | —N CH$_3$SO$_2$CH$_3$ |

TABLE 2-continued

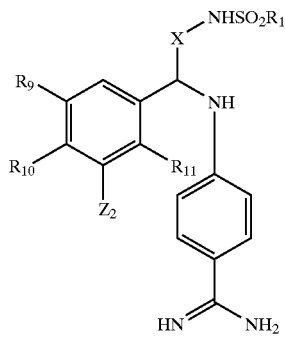

| Compound No | $Z^2$ | $R^1$ | $R^9$ | $R^{10}$ | $R^{11}$ |
|---|---|---|---|---|---|
| 605 | —H | 2-thienyl | —OCH$_2$CH$_3$ | —OCH$_2$Ph | —N CH$_3$SO$_2$CH$_3$ |
| 606 | —H | 2-thienyl | —OCH$_2$CH$_3$ | —OCH$_2$CH$_3$ | —N CH$_3$SO$_2$CH$_3$ |
| 607 | —H | -n-Butyl | —OCH$_2$CH$_3$ | —OCH$_2$CH$_3$ | —N CH$_3$SO$_2$CH$_3$ |
| 608 | —H | -isopropyl | —OCH$_2$CH$_3$ | —OCH$_2$CH$_3$ | —N CH$_3$SO$_2$CH$_3$ |
| 609 | —H | -isobutyl | —OCH$_2$CH$_3$ | —OCH$_2$CH$_3$ | —N CH$_3$SO$_2$CH$_3$ |
| 610 | —H | -sec-butyl | —OCH$_2$CH$_3$ | —OCH$_2$CH$_3$ | —N CH$_3$SO$_2$CH$_3$ |
| 611 | —H | —CH$_2$CH$_2$Cl | —OCH$_2$CH$_3$ | —OCH$_2$CH$_3$ | —N CH$_3$SO$_2$CH$_3$ |
| 612 | —H | —CH$_2$CH$_2$CH$_2$Cl | —OCH$_2$CH$_3$ | —OCH$_2$CH$_3$ | —N CH$_3$SO$_2$CH$_3$ |
| 613 | —H | —CH$_2$CH$_2$CH$_3$ | —OCH$_2$CH$_3$ | —OCH$_2$CH$_3$ | —NHSO$_2$i-Pr |
| 614 | —H | —CH$_2$CH$_2$CH$_3$ | —OCH$_2$CH$_3$ | —OCH$_2$Ph | —NHSO$_2$i-Pr |
| 615 | —H | phenyl | —OCH$_2$CH$_3$ | —OCH$_2$CH$_3$ | —NHSO$_2$i-Pr |
| 616 | —H | phenyl | —OCH$_2$CH$_3$ | —OCH$_2$Ph | —NHSO$_2$i-Pr |
| 617 | —H | 2-thienyl | —OCH$_2$CH$_3$ | —OCH$_2$Ph | —NHSO$_2$i-Pr |
| 618 | —H | 2-thienyl | —OCH$_2$CH$_3$ | —OCH$_2$CH$_3$ | —NHSO$_2$i-Pr |
| 619 | —H | -n-Butyl | —OCH$_2$CH$_3$ | —OCH$_2$CH$_3$ | —NHSO$_2$i-Pr |
| 620 | —H | -isopropyl | —OCH$_2$CH$_3$ | —OCH$_2$CH$_3$ | —NHSO$_2$i-Pr |
| 621 | —H | -isobutyl | —OCH$_2$CH$_3$ | —OCH$_2$CH$_3$ | —NHSO$_2$i-Pr |
| 622 | —H | -sec-butyl | —OCH$_2$CH$_3$ | —OCH$_2$CH$_3$ | —NHSO$_2$i-Pr |
| 623 | —H | —CH$_2$CH$_2$Cl | —OCH$_2$CH$_3$ | —OCH$_2$CH$_3$ | —NHSO$_2$i-Pr |
| 624 | —H | —CH$_2$CH$_2$CH$_2$Cl | —OCH$_2$CH$_3$ | —OCH$_2$CH$_3$ | —NHSO$_2$i-Pr |

TABLE 2-continued

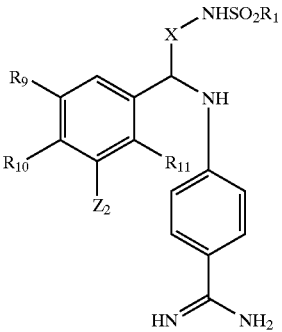

| Compound No | $Z^2$ | $R^1$ | $R^9$ | $R^{10}$ | $R^{11}$ |
|---|---|---|---|---|---|
| 625 | —H | —CH₂CH₂CH₃ | —OCH₂CH₃ | —OCH₂CH₃ | —NHSO₂Ph |
| 626 | —H | —CH₂CH₂CH₃ | —OCH₂CH₃ | —OCH₂Ph | —NHSO₂Ph |
| 627 | —H | 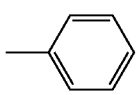 | —OCH₂CH₃ | —OCH₂CH₃ | —NHSO₂Ph |
| 628 | —H | 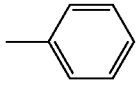 | —OCH₂CH₃ | —OCH₂Ph | —NHSO₂Ph |
| 629 | —H | 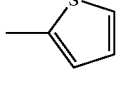 | —OCH₂CH₃ | —OCH₂Ph | —NHSO₂Ph |
| 630 | —H | 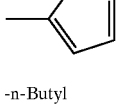 | —OCH₂CH₃ | —OCH₂CH₃ | —NHSO₂Ph |
| 631 | —H | -n-Butyl | —OCH₂CH₃ | —OCH₂CH₃ | —NHSO₂Ph |
| 632 | —H | -isopropyl | —OCH₂CH₃ | —OCH₂CH₃ | —NHSO₂Ph |
| 633 | —H | -isobutyl | —OCH₂CH₃ | —OCH₂CH₃ | —NHSO₂Ph |
| 634 | —H | -sec-butyl | —OCH₂CH₃ | —OCH₂CH₃ | —NHSO₂Ph |
| 635 | —H | —CH₂CH₂Cl | —OCH₂CH₃ | —OCH₂CH₃ | —NHSO₂Ph |
| 636 | —H | —CH₂CH₂CH₂Cl | —OCH₂CH₃ | —OCH₂CH₃ | —NHSO₂Ph |
| 637 | —H | —CH₂CH₂CH₃ | —OCH₂CH₃ | —OCH₂CH₃ | 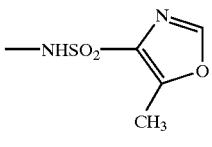 |
| 638 | —H | —CH₂CH₂CH₃ | —OCH₂CH₃ | —OCH₂Ph | 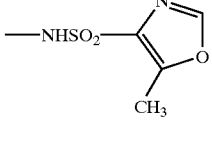 |
| 639 | —H | 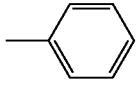 | —OCH₂CH₃ | —OCH₂CH₃ | 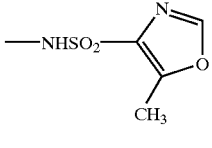 |

TABLE 2-continued
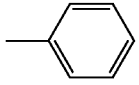
| Compound No | $Z^2$ | $R^1$ | $R^9$ | $R^{10}$ | $R^{11}$ |
|---|---|---|---|---|---|
| 640 | —H | 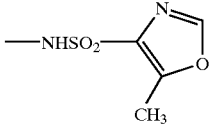 | —OCH$_2$CH$_3$ | —OCH$_2$Ph | 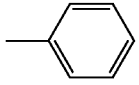 |
| 641 | —H | 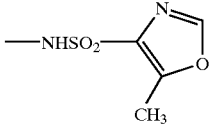 | —OCH$_2$CH$_3$ | —OCH$_2$Ph | 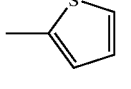 |
| 642 | —H | 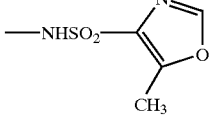 | —OCH$_2$CH$_3$ | —OCH$_2$CH$_3$ | 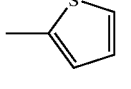 |
| 643 | —H | -n-Butyl | —OCH$_2$CH$_3$ | —OCH$_2$CH$_3$ | 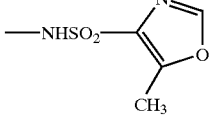 |
| 644 | —H | -isopropyl | —OCH$_2$CH$_3$ | —OCH$_2$CH$_3$ | 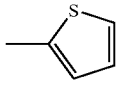 |
| 645 | —H | -isobutyl | —OCH$_2$CH$_3$ | —OCH$_2$CH$_3$ | 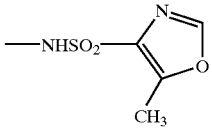 |
| 646 | —H | -sec-butyl | —OCH$_2$CH$_3$ | —OCH$_2$CH$_3$ | 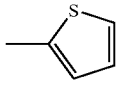 |
| 647 | —H | —CH$_2$CH$_2$Cl | —OCH$_2$CH$_3$ | —OCH$_2$CH$_3$ | 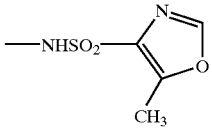 |

TABLE 2-continued

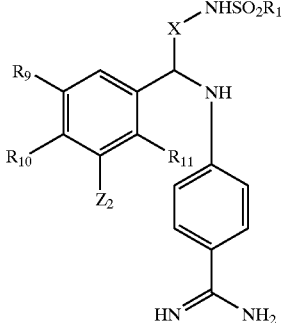

| Compound No | $Z^2$ | $R^1$ | $R^9$ | $R^{10}$ | $R^{11}$ |
|---|---|---|---|---|---|
| 648 | —H | —CH$_2$CH$_2$CH$_3$ | —OCH$_2$CH$_3$ | —OCH$_2$CH$_3$ | —NHSO$_2$- 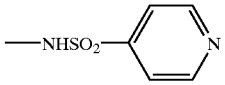 |
| 649 | —H | —CH$_2$CH$_2$CH$_3$ | —OCH$_2$CH$_3$ | —OCH$_2$Ph | —NHSO$_2$- 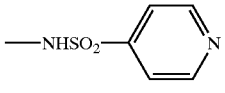 |
| 650 | —H | 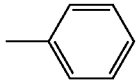 | —OCH$_2$CH$_3$ | —OCH$_2$CH$_3$ | —NHSO$_2$- 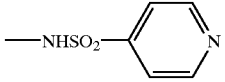 |
| 651 | —H | 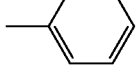 | —OCH$_2$CH$_3$ | —OCH$_2$Ph | —NHSO$_2$- 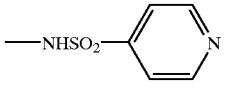 |
| 652 | —H | 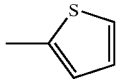 | —OCH$_2$CH$_3$ | —OCH$_2$Ph | —NHSO$_2$- 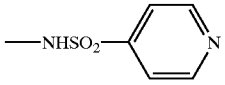 |
| 653 | —H | 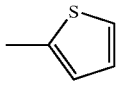 | —OCH$_2$CH$_3$ | —OCH$_2$CH$_3$ | —NHSO$_2$- 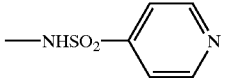 |
| 654 | —H | -n-Butyl | —OCH$_2$CH$_3$ | —OCH$_2$CH$_3$ | —NHSO$_2$- 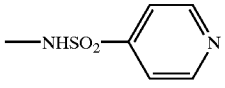 |
| 655 | —H | -isopropyl | —OCH$_2$CH$_3$ | —OCH$_2$CH$_3$ | —NHSO$_2$- 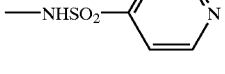 |
| 656 | —H | -isobutyl | —OCH$_2$CH$_3$ | —OCH$_2$CH$_3$ | —NHSO$_2$- 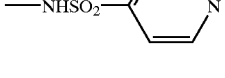 |
| 657 | —H | -sec-butyl | —OCH$_2$CH$_3$ | —OCH$_2$CH$_3$ | —NHSO$_2$-  |
| 658 | —H | —CH$_2$CH$_2$Cl | —OCH$_2$CH$_3$ | —OCH$_2$CH$_3$ | —NHSO$_2$-  |

TABLE 2-continued

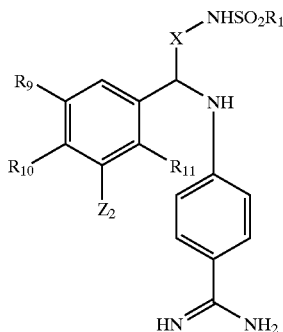

| Compound No | $Z^2$ | $R^1$ | $R^9$ | $R^{10}$ | $R^{11}$ |
|---|---|---|---|---|---|
| 659 | —H | —CH$_2$CH$_2$CH$_2$Cl | —OCH$_2$CH$_3$ | —OCH$_2$CH$_3$ | —NHSO$_2$-(4-pyridyl) |
| 660 | —H | —CH$_2$CH$_2$CH$_3$ | —OCH$_2$CH$_3$ | —OCH$_2$CH$_3$ | —OCHMeCO$_2$H |
| 661 | —H | —CH$_2$CH$_2$CH$_3$ | —OCH$_2$CH$_3$ | —OCH$_2$Ph | —OCHMeCO$_2$H |
| 662 | —H | phenyl | —OCH$_2$CH$_3$ | —OCH$_2$CH$_3$ | —OCHMeCO$_2$H |
| 663 | —H | phenyl | —OCH$_2$CH$_3$ | —OCH$_2$Ph | —OCHMeCO$_2$H |
| 664 | —H | 2-thienyl | —OCH$_2$CH$_3$ | —OCH$_2$Ph | —OCHMeCO$_2$H |
| 665 | —H | 2-thienyl | —OCH$_2$CH$_3$ | —OCH$_2$CH$_3$ | —OCHMeCO$_2$H |
| 666 | —H | n-Butyl | —OCH$_2$CH$_3$ | —OCH$_2$CH$_3$ | —OCHMeCO$_2$H |
| 667 | —H | -isopropyl | —OCH$_2$CH$_3$ | —OCH$_2$CH$_3$ | —OCHMeCO$_2$H |
| 668 | —H | -isobutyl | —OCH$_2$CH$_3$ | —OCH$_2$CH$_3$ | —OCHMeCO$_2$H |
| 669 | —H | -sec-butyl | —OCH$_2$CH$_3$ | —OCH$_2$CH$_3$ | —OCHMeCO$_2$H |
| 670 | —H | —CH$_2$CH$_2$Cl | —OCH$_2$CH$_3$ | —OCH$_2$CH$_3$ | —OCHMeCO$_2$H |
| 671 | —H | —CH$_2$CH$_2$CH$_2$Cl | —OCH$_2$CH$_3$ | —OCH$_2$CH$_3$ | —OCHMeCO$_2$H |
| 672 | —H | —CH$_2$CH$_2$CH$_3$ | —OCH$_2$CH$_3$ | —OCH$_2$CH$_3$ | —NHSO$_2$CH$_3$ |
| 673 | —H | phenyl | —OCH$_2$CH$_3$ | —OCH$_2$CH$_3$ | —NHSO$_2$CH$_3$ |
| 674 | —H | phenyl | —OCH$_2$CH$_3$ | —OCH$_2$Ph | —NHSO$_2$CH$_3$ |
| 675 | —H | 2-thienyl | —OCH$_2$CH$_3$ | —OCH$_2$Ph | —NHSO$_2$CH$_3$ |

TABLE 2-continued

| Compound No | $Z^2$ | $R^1$ | $R^9$ | $R^{10}$ | $R^{11}$ |
|---|---|---|---|---|---|
| 676 | —H | 2-thienyl | —OCH$_2$CH$_3$ | —OCH$_2$CH$_3$ | —NHSO$_2$CH$_3$ |
| 677 | —H | -propyl | —OCH$_2$CH$_3$ | —OH | —NHSO$_2$CH$_3$ |
| 678 | —H | -isopropyl | —OCH$_2$CH$_3$ | —OCH$_2$CH$_3$ | —NHSO$_2$CH$_3$ |
| 679 | —H | -isobutyl | —OCH$_2$CH$_3$ | —OCH$_2$CH$_3$ | —NHSO$_2$CH$_3$ |
| 680 | —H | -sec-butyl | —OCH$_2$CH$_3$ | —OCH$_2$CH$_3$ | —NHSO$_2$CH$_3$ |
| 681 | —H | —CH$_2$CH$_2$Cl | —OCH$_2$CH$_3$ | —OCH$_2$CH$_3$ | —NHSO$_2$CH$_3$ |
| 682 | —H | —CH$_2$CH$_2$CH$_2$Cl | —OCH$_2$CH$_3$ | —OCH$_2$CH$_3$ | —NHSO$_2$CH$_3$ |
| 683 | —OCH$_2$CH$_3$ | —CH$_2$CH$_2$CH$_3$ | —OCH$_2$CH$_3$ | —H | —H |
| 684 | —OCH$_2$CH$_3$ | —CH$_2$CH$_3$ | —OCH$_2$CH$_3$ | —H | —H |
| 685 | —OCH$_2$CH$_3$ | —CH$_2$CH$_2$CH$_2$CH$_3$ | —OCH$_2$CH$_3$ | —H | —H |
| 686 | —OCH$_2$CH$_3$ | phenyl | —OCH$_2$CH$_3$ | —H | —H |
| 687 | —OCH$_2$CH$_3$ | 2-thienyl | —OCH$_2$CH$_3$ | —H | —H |
| 688 | —OCH(CH$_3$)$_2$ | —CH$_2$CH$_2$CH$_3$ | —OCH$_2$CH$_3$ | —H | —H |
| 689 | —OCH(CH$_3$)$_2$ | —CH$_2$CH$_3$ | —OCH$_2$CH$_3$ | —H | —H |
| 690 | —OCH(CH$_3$)$_2$ | —CH$_2$CH$_2$CH$_2$CH$_3$ | —OCH$_2$CH$_3$ | —H | —H |
| 691 | —OCH(CH$_3$)$_2$ | phenyl | —OCH$_2$CH$_3$ | —H | —H |
| 692 | —OCH(CH$_3$)$_2$ | 2-thienyl | —OCH$_2$CH$_3$ | —H | —H |
| 693 | -CH$_2$-(pyrrolidin-1-yl) | phenyl | —OCH$_2$CH$_3$ | —H | —H |
| 694 | -CH$_2$-(pyrrolidin-1-yl) | —CH$_2$CH$_2$CH$_3$ | —OCH$_2$CH$_3$ | —H | —H |

TABLE 2-continued

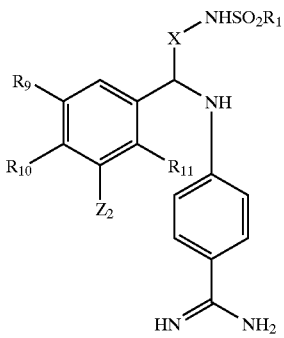

| Compound No | $Z^2$ | $R^1$ | $R^9$ | $R^{10}$ | $R^{11}$ |
|---|---|---|---|---|---|
| 695 | —H | CH(CH₃)CH₂NH₂ | —OCH₂CH₃ | —OCH₂CH₃ | —NHSO₂CH₃ |
| 696 | —H | CH(CH₃)CH₂NH₂ | —OCH₂CH₃ | —OCH₂CH₃ | —N(CH₃)SO₂CH₃ |
| 697 | —H | CH(CH₃)CH₂NH₂ | —OCH₂CH₃ | —OCH₂CH₃ | —NHSO₂CH₂CO₂H |
| 698 | —H | CH(CH₃)CH₂NH₂ | —OCH₂CH₃ | —OCH₂CH₃ | —NHSO₂CH₂SO₂CH₃ |
| 699 | —H | 2-thienyl | —OCH₂CH₃ | —OCH₂CH₃ | —NHSO₂CH₂SO₂CH₃ |
| 700 | —H | —CH₂CH₂CH₃ | —OCH₂CH₃ | —OCH₂CH₃ | —NHSO₂CH₂SO₂CH₃ |
| 701 | —H | —CH₂CH₃ | —OCH₂CH₃ | —OCH₂CH₃ | —NHSO₂CH₂SO₂CH₃ |
| 702 | —H | —CH₂CH₂CH₂CH₃ | —OCH₂CH₃ | —OCH₂CH₃ | —NHSO₂CH₂SO₂CH₃ |
| 703 | —H | phenyl | —OCH₂CH₃ | —OCH₂CH₃ | —NHSO₂CH₂SO₂CH₃ |

TABLE 2-continued
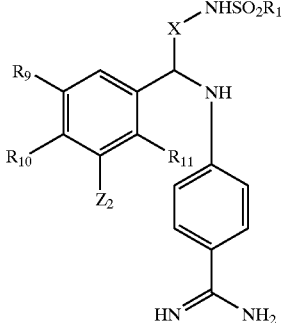
| Compound No | Z² | R¹ | R⁹ | R¹⁰ | R¹¹ |
|---|---|---|---|---|---|
| 704 | —H | —CH₂CH₂CO₂H | —OCH₂CH₃ | —OCH₂CH₃ | 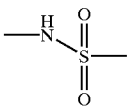 |
| 705 | —H | —CH₂CH₂CONH₂ | —OCH₂CH₃ | —OCH₂CH₃ | 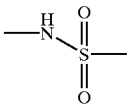 |
| 706 | —H | —CH₂CH₂CH₂OH | —OCH₂CH₃ | —OCH₂CH₃ | 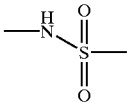 |
| 707 | —H |  | —OCH₂CH₃ | —OCH₂CH₃ | 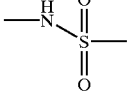 |
| 708 | —H | 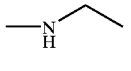 | —OCH₂CH₃ | —OCH₂CH₃ | 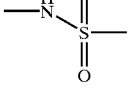 |
| 709 | —H | 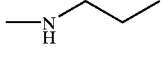 | —OCH₂CH₃ | —OCH₂CH₃ | 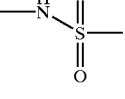 |
| 710 | —H | 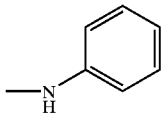 | —OCH₂CH₃ | —OCH₂CH₃ | 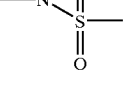 |
| 711 | —H | 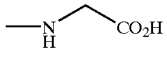 | —OCH₂CH₃ | —OCH₂CH₃ | 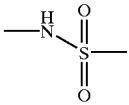 |
| 712 | —H | 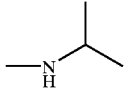 | —OCH₂CH₃ | —OCH₂CH₃ | 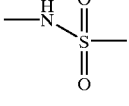 |

TABLE 2-continued

[Structure: benzene ring with substituents R9, R10, R11, Z2, and a CH(X-NHSO2R1)(NH-Ar) group where Ar is 4-amidinophenyl]

| Compound No | Z² | R¹ | R⁹ | R¹⁰ | R¹¹ |
|---|---|---|---|---|---|
| 713 | —H | —N(CH₃)₂ | —OCH₂CH₃ | —OCH₂CH₃ | —NH—S(O)₂—CH₃ |
| 714 | —H | —N(CH₃)(C₂H₅) | —OCH₂CH₃ | —OCH₂CH₃ | —NH—S(O)₂—CH₃ |
| 715 | —H | —N(C₂H₅)₂ | —OCH₂CH₃ | —OCH₂CH₃ | —NH—S(O)₂—CH₃ |
| 716 | —H | 4-(CH₂NH₂)-C₆H₄— | —OCH₂CH₃ | —OCH₂CH₃ | —NH—S(O)₂—CH₃ |
| 717 | —H | 4-(NH₂)-C₆H₄— | —OCH₂CH₃ | —OCH₂CH₃ | —NH—S(O)₂—CH₃ |
| 718 | —H | 3-(NH₂)-C₆H₄— | —OCH₂CH₃ | —OCH₂CH₃ | —NH—S(O)₂—CH₃ |
| 719 | —H | —NH(CH₃) | —OCH₂CH₃ | —OCH₂CH₃ | —NH—S(O)₂—CH₂CO₂H |
| 720 | —H | —NH(C₂H₅) | —OCH₂CH₃ | —OCH₂CH₃ | —NH—S(O)₂—CH₂CO₂H |
| 721 | —H | —NH(C₃H₇) | —OCH₂CH₃ | —OCH₂CH₃ | —NH—S(O)₂—CH₂CO₂H |

TABLE 2-continued

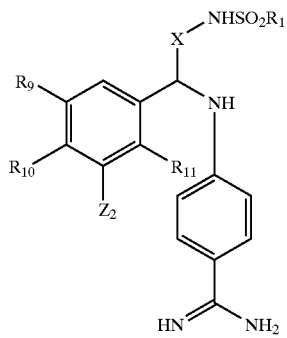

| Compound No | $Z^2$ | $R^1$ | $R^9$ | $R^{10}$ | $R^{11}$ |
|---|---|---|---|---|---|
| 722 | —H | NHPh | —OCH$_2$CH$_3$ | —OCH$_2$CH$_3$ | —NHSO$_2$CH$_2$CO$_2$H |
| 723 | —H | NHCH$_2$CO$_2$H | —OCH$_2$CH$_3$ | —OCH$_2$CH$_3$ | —NHSO$_2$CH$_2$CO$_2$H |
| 724 | —H | NHiPr | —OCH$_2$CH$_3$ | —OCH$_2$CH$_3$ | —NHSO$_2$CH$_2$CO$_2$H |
| 725 | —H | N(CH$_3$)$_2$ | —OCH$_2$CH$_3$ | —OCH$_2$CH$_3$ | —NHSO$_2$CH$_2$CO$_2$H |
| 726 | —H | N(CH$_3$)(Et) | —OCH$_2$CH$_3$ | —OCH$_2$CH$_3$ | —NHSO$_2$CH$_2$CO$_2$H |
| 727 | —H | N(Et)$_2$ | —OCH$_2$CH$_3$ | —OCH$_2$CH$_3$ | —NHSO$_2$CH$_2$CO$_2$H |
| 728 | —H | 4-(CH$_2$NH$_2$)C$_6$H$_4$— | —OCH$_2$CH$_3$ | —OCH$_2$CH$_3$ | —NHSO$_2$CH$_2$CO$_2$H |
| 729 | —H | 4-(NH$_2$)C$_6$H$_4$— | —OCH$_2$CH$_3$ | —OCH$_2$CH$_3$ | —NHSO$_2$CH$_2$CO$_2$H |
| 730 | —H | 3-(NH$_2$)C$_6$H$_4$— | —OCH$_2$CH$_3$ | —OCH$_2$CH$_3$ | —NHSO$_2$CH$_2$CO$_2$H |

The compounds of the invention contain one or more asymmetric carbon atoms. Accordingly, the compounds may exist as diastereomers, enantiomers or mixtures thereof. The syntheses described above may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

Utility

It has been discovered that the compounds of the invention when made and selected as disclosed herein are inhibitors of serine protease enzymes, for example, factor VIIa, TF/factor VIIa, factor Xa, kallikrein and/or thrombin. These compounds are capable of inhibiting the catalytic activity of these enzymes and as such function to inhibit the coagulation cascade and prevent or limit coagulation and/or the formation of thrombi or emboli in blood vessels and/or increase the time of coagulation of blood. The compounds of the present invention, therefore, inhibit the ability of TF/factor VIIa to convert factor X to factor Xa, inhibit the ability of factor Xa to convert prothrombin to thrombin (factor IIa); and/or the ability of thrombin to convert fibrinogen to fibrin monomers.

The selectivity of the compounds of the invention as inhibitors of these enzymes can be determined using Ki values as described in the examples below. Representative selectivities are shown in the tables below.

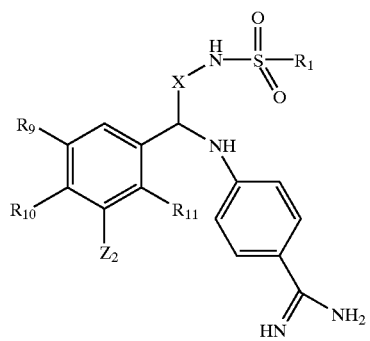

| R1 | X | R9 | R10 | Z2 | R11 | Ki(TFVIIa) uM |
|---|---|---|---|---|---|---|
| Ph | C=O | OEt | OiPr | H | H | 0.003 |
| Pr | CH2 | OEt | OCH2Ph | H | NHSO2Me | 0.004 |
| Ph | C=O | OEt | OEt | H | H | 0.005 |
| Ph | C=O | OEt | H | OEt | H | 0.007 |

| R1 | X | R9 | R10 | Z2 | R11 | Ki(IIa) uM |
|---|---|---|---|---|---|---|
| Ph | CH2 | OMe | OCH(CH2Cl)Ph | H | H | 0.001 |
| 2-thiophene | CH2 | OMe | OCH2Ph | H | H | 0.016 |
| Ph | C=O | OEt | OiPr | H | H | 0.113 |
| Pr | CH2 | OMe | OCH(CH2Cl)Ph | H | H | 0.001 |

| R1 | X | R9 | R10 | Z2 | R11 | Ki(Kallikrein) uM |
|---|---|---|---|---|---|---|
| Pr | CH2 | OEt | OiBu | H | NHSO2Pr | 0.001 |
| Pr | CH2 | OEt | OiPr | H | NHSO2Me | 0.001 |
| Et | C=O | OEt | OiPr | H | H | 0.011 |
| Ph | C=O | OEt | OEt | H | H | 0.002 |

| R1 | X | R9 | R10 | Z2 | R11 | Ki(Xa) uM |
|---|---|---|---|---|---|---|
| Et | C=O | OEt | OiPr | H | H | 0.565 |
| Bu | C=O | OEt | OiPr | H | H | 0.624 |
| Ph | C=O | OEt | OiPr | H | H | 0.898 |
| Pr | CH2 | OMe | OCH(CH2Cl)Ph | H | H | 0.140 |

The anti-coagulant activity of the compounds of the invention can be tested using assays. Prothrombin time (PT) and activated partial thromboplastin time (APTT) clotting time assays can be performed in pooled normal plasmas (human or various animal species) following addition of increasing concentrations of inhibitors to the plasma. Clotting times are determined using an ACL 300 Automated Coagulation Analyzer (Coulter Corp., Miami, Fla.) and commercially available reagents as follows.

PT assay: Aqueous solutions of inhibitor at various concentrations are added to pooled normal plasma in a ratio of 1 part inhibitor to 9 parts plasma. These mixtures are then added to the analyzer's sample cups. Innovin® (Dade International Inc., Miami, Fla.), a mixture of human relipidated tissue factor and $Ca^{++}$ ions is added to the reagent cup.

Precise volumes of sample and Innovin® are automatically transferred to cells of an acrylic rotor that is pre-equilibrated to 37C. Following a 2 minute incubation period, coagulation is initiated when the two components are mixed together by centrifugation. Coagulation is monitored optically and clotting time is reported in seconds. In agreement with Janson et al. (Janson, T. L., et al., 1984, *Haemostasis* 14: 440–444) relipidated human tissue factor is a potent initiator of coagulation in all species tested. In this system, the clotting time of control plasmas (plasma plus inhibitor diluent) is typically 8 to 10 seconds. A curve is fit to the clotting time versus inhibitor concentration data and the concentration at which the PT is doubled compared to control plasma is determined for each inhibitor.

APTT assay: Inhibitor and plasma are mixed together and transferred to the ACL 300 sample cups as described above. Actin FS® and $CaCl_2$ (Dade International Inc., Miami, Fla.), are added to reagent cups 1 and 2 respectively. Precise volumes of sample and activator (Actin FS® ) are automatically transferred to cells of a pre-equilibrated rotor (37C) and mixed by centrifugation. Following a 2 minute activation period, coagulation is initiated by the addition of $CaCl_2$. Coagulation is monitored and data calculated as described in the PT method. APTT of plasma controls is typically 12 to 32 seconds, depending on the species of plasma used in the assay.

Representative PT and APTT assay results are shown in Table 3 below.

TABLE 3

| Compound No. | 2 × PT ($\mu$M) | 2 × APTT ($\mu$M) |
| --- | --- | --- |
| 7 | 14 | 8 |
| 13 | 16 | 57 |
| 33 | 5.5 | 11 |
| 72 | 30 | 60 |
| 589 | 22 | 40 |
| 596 | 8 | 140 |
| 628 | 125 | 90 |
| 672 | 34 | 78 |

The compounds of the invention are useful as diagnostic reagents in vitro for inhibiting clotting in blood drawing tubes. The use of stoppered test tubes having a vacuum therein as a means to draw blood is well known. Kasten, B. L., "Specimen Collection", Laboratory Test Handbook, 2nd Ed., Lexi-Comp Inc., Cleveland, PP 16–17, Jacobs, D. S. et al, 1990. Such vacuum tubes may be free of clot-inhibiting additives, in which case, they are useful for the isolation of mammalian serum from the blood. They may also contain clot-inhibiting additives, such as heparin salts, citrate salts or oxalate salts, in which case they are useful for the isolation of mammalian plasma from the blood. The compounds of the invention may be incorporated into blood collection tubes and function to inhibit TF/factor VIIa, factor Xa, thrombin and/or kallikrein and to prevent clotting of the mammalian blood drawn into the tubes.

When used in blood collection tubes, the compounds of the invention may be used alone, as mixtures or in combination with other clotting inhibiting compounds known in this art. The amount of the compound of the invention should be an amount sufficient to prevent or inhibit the formation of a clot when blood is drawn into the tube. These compounds may be introduced into the tubes in the same manner as known clot-inhibiting compounds such as heparin salts. Liquids are usually lyophilized using known methods. Typically, the tubes will contain about 2 to about 10 ml of mammalian blood and the compounds are added in an amount sufficient to prevent coagulation of this amount of blood. A suitable concentration is about 10–1000 nM.

These compounds also inhibit the formation of emboli and thrombi in the circulatory system in mammals and therefore are useful in vivo. Thromboembolic disorders have been shown to be directly related to the susceptibility of the mammal to formation of emboli and thrombi. For example, the formation of a thrombus in a veinous vessel results in thrombophlebitis, which is typically treated with rest and the administration of anticoagulants. Other conditions which can be treated with the anticoagulant compounds of the invention include, thrombolymphangitis, thrombosinusitis, thromboendocarditis, thromboangiitis, and thromboarteritis.

Mammals exposed to medical procedures such as angioplasty and thrombolytic therapy are particularly susceptible to thrombus formation. The compounds of the present invention can be used to inhibit thrombus formation following angioplasty. They may also be used in combination with antithrombolytic agents such as tissue plasminogen activator and its derivatives (U.S. Pat. Nos. 4,752,603; 4,766,075; 4,777,043; EP 199 574; EP 238 304; EP 228 862; EP 297 860; PCT WO89/04368; PCT WO89/00197), streptokinase and its derivatives, or urokinase and its derivatives to prevent arterial reocclusion following thrombolytic therapy. When used in combination with the above thrombolytic agents, the compounds of the present invention may be administered prior to, simultaneously with, or subsequent to tile antithrombolytic agent.

Mammals exposed to renal dialysis, blood oxygenation, cardiac catheterization and similar medical procedures as well as mammals fitted with certain prosthetic devices are also susceptible to thromboembolic disorders. Physiologic conditions, with or without known cause may also lead to thromboembolic disorders.

Thus, the compounds described herein may be useful in treating thromboembolic disorders in mammals. The compounds described herein may also be used as adjuncts to anticoagulant therapy, for example in combination with aspirin, heparin or warfarin and other anticoagulant agents. The various coagulation disorders described above are treated with the compounds of the invention in such a fashion as to prevent bleeding as a result of the disorder. The application of the compounds described herein for these and related disorders will be apparent to those skilled in the art.

Compounds of this invention are also useful as intermediates generally, or as precursors of coagulation serine protease inhibitors and thus in addition to treating cardiovascular disease, these compounds may be usefully employed in metastatic disease, or for any disease where inhibition of coagulation is indicated.

Typically, the inhibitors used in the method of this invention is formulated by mixing it at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but preferably ranges anywhere from about 3 to about 8. Formulation in an acetate buffer at pH 5 is a suitable embodiment.

The inhibitory compound for use herein is preferably sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01–100 mg/kg, preferably about 0.1 to 20 mg/kg of patient body weight per day, with the typical initial range of compound used being 0.3 to 15 mg/kg/day.

The compound of the invention is administered by any suitable means, including oral, topical, transdermal, parenteral, subcutaneous, intraperitoneal, intrapulmonary, and intranasal, and, if desired for local immunosuppressive treatment, intralesional administration (including perfusing or otherwise contacting the graft with the inhibitor before transplantation). Parenteral infusions include intramuscular, intravenous, intraarterial, intraperitoneal, or subcutaneous administration.

The invention will be more fully understood by reference to the following examples. They should not, however, be construed as limiting the scope of the invention. All patent and literature citations are herein incorporated by reference in their entirety.

EXAMPLES

The compounds of the invention can be prepared generally by the reaction scheme shown below.

Compounds other than the specific product shown are prepared as described above using corresponding starting materials. For example, additional compounds can be prepared by using different starting styrene compounds, which are readily prepared from commercially available starting compounds and standard reactions which are well known in this art.

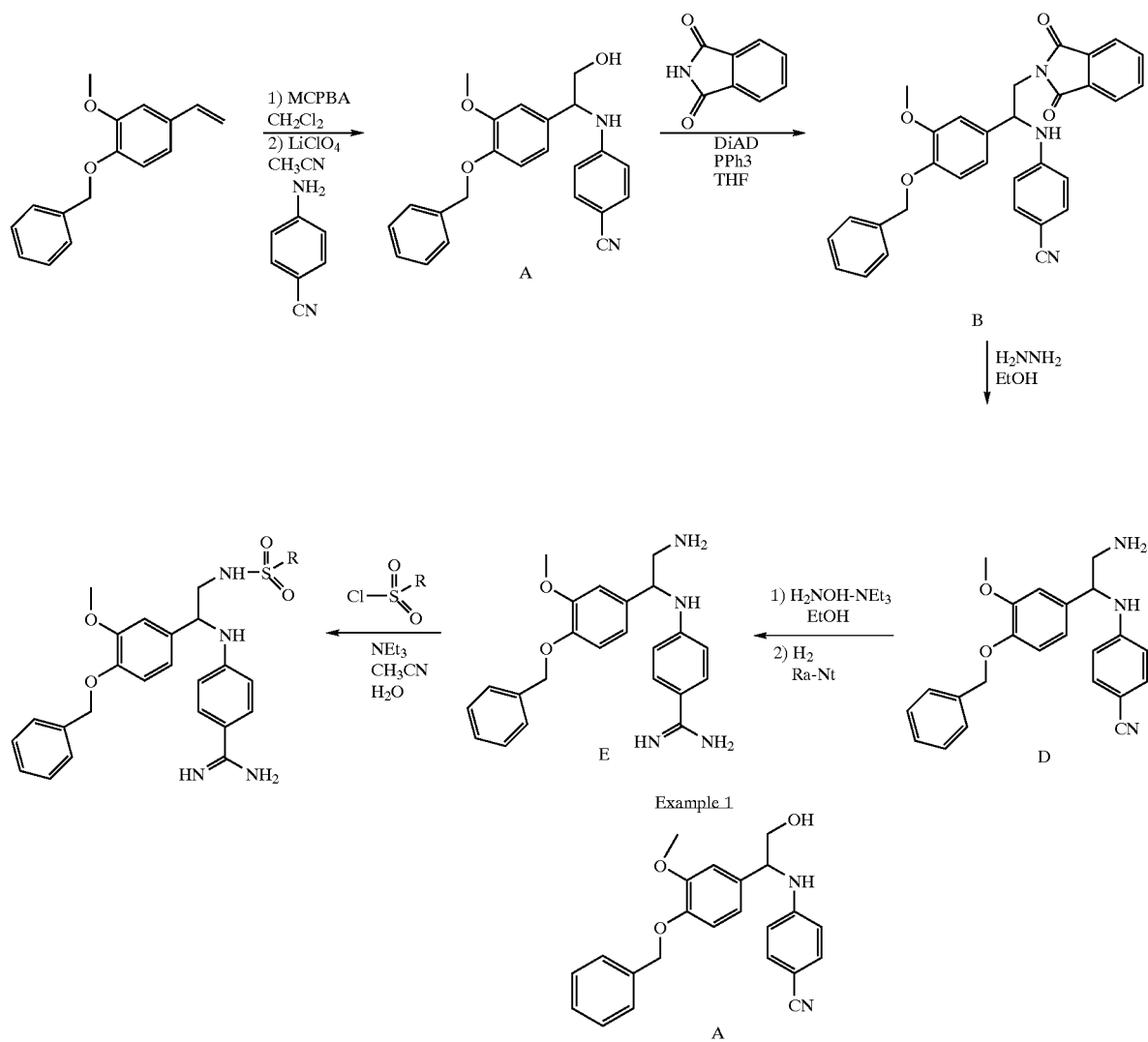

4-benzyloxy-3-methoxy-styrene (10 g, 42 mmoles) was dissolved in dichloromethane (400 ml). Solid potassium bicarbonate (11 g, 110 mmoles) was added and the reaction cooled to zero degrees Celsius. Meta-chloroperbenzoic acid (12 g, ca. 42 mmoles) was added and the reaction allowed to wane to room temperature and stirred for 16 hours. The reaction was monitored by thin-layer chromatography. An additional amount of meta-chloroperbenzoic acid (4 g) was added and the reaction stirred for an additional 4 hours to completely consume starting material. The reaction was poured into a separatory funnel and washed first with water, then with sodium bicarbonate and finally with NaOH. The organic layer was separated and dried over anhydrous sodium sulfate. The solution was filtered and the solvent removed in vacuo to yield approximately 11 g of crude product.

The crude product was then dissolved in acetonitrile (60 ml) and lithium perchlorate (8.5 g, 80 mmoles) added The suspension was stirred for five minutes at which time the reaction became homogeneous. 4-amino-benzonitrile (9.5 g, 80 mmoles) was added and the reaction heated to 60 degrees C. for 12 hours Thin layer chromatography showed the presence of a new product at lower Rf. The solvent was removed in vacuo and the residue taken up in ethyl acetate, washed with water an dried over anhydrous sodium sulfate. The crude product was then submitted to flash chromatography (hexanes:ethyl acetate 1:1) to yield 6 grams of 4-[1-(4-Benzyloxy-3-methoxy-phenyl)-2-hydroxy-ethylamino]-benzonitrile A $^1$HNMR(CDCl$_3$): 7.3–7 45, (m, 7H), 6.8 (m, 3H), 6.5 (d, 2H), 5.18 (s, 2H), 4.42 (m, 1H), 3.95 (dd, 1H), 3.85 (s, 3H), 3.8 (dd, 1H).

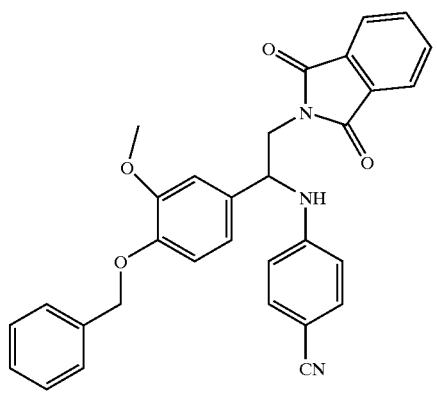

B

4-[1-(4-Benzyloxy-3-methoxy-phenyl)-2-hydroxy-ethylamino]-benzonitrile A (470 mg, 1.25 mmoles), phthalimide (1.47 g, 10 mmoles), and triphenylphosphine (787 mg, 3 mmoles) were added to 40 ml of tetrahydrofuran. The mixture was stirred for 10 minutes and then cooled to zero degrees Celsius. Diisopropylazodiacarboxylate (DIAD, 0.6 ml, 3 mmoles) was then added slowly. The reaction was allowed to stir 1 hour. TLC indicated new product. The solvent was removed in vacuo and the residue taken up in 50 ml of ethyl acetate. The solution was washed three times with 2N sodium hydroxide and twice with water. The organic layer was separated, dried over anhydrous sodium sulfate and filtered. The solvent was removed in vacuo and the residue submitted to flash chromatography (hexanes:ethyl acetate, 1:1) to yield 478 mg of product 4-[1-(4-Benzyloxy-3-methoxy-phenyl)-2-(1,3-dioxo-1,3-diydro-isoindol-2-yl)-ethylamino]-benzonitrile B (76% yield). $^1$HNMR(CDCl$_3$): 7.85 (m, 2H,), 7.75 (m, 2H), 7.23–7.45 (m, 9H), 6.9 (m, 3H), 6.42 (d, 2H), 5.45 (d, 1H), 5.15 (s, 2H), 4.62 (m, 1H), 4.0 (m, 2H), 3.83 (s, 3H).

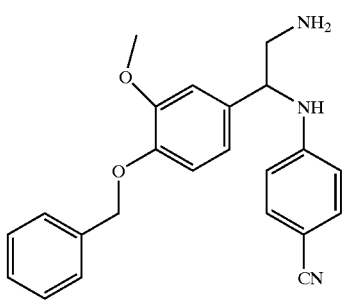

D

4-[1-(4-Benzyloxy-3-methoxy-phenyl)-2-(1,3-dioxo-1,3-dihydro-isoindol-2-yl)-ethylamino]-benzonitrile B was then dissolved in ethanol (60 ml) and hydrazine hydrate (2 g) was added. The solution was heated to 60–70 degrees C. for 1.5 hours. TLC showed reaction was complete. The suspension was filtered to remove by-product and the ethanol removed in vacuo. The residue was submitted to flash chromatography on silica gel (ethyl acetate: 2N NH3 in methanol, 9:1) to yield 372 mg of 4-[2-Amino-1-(4-benzyloxy-3methoxy-phenyl)-ethylamino]-benzonitrile D (100%). $^1$HNMR (CDCl$_3$): 7.3–7.45 (m, 7H), 6.32 (m, 3H), 6.5 (d, 2H), 5.52 (d, 1H), 4.3 (q, 1H), 3.83 (s, 3H), 3.08 (m, 2H), 1.95 (s,

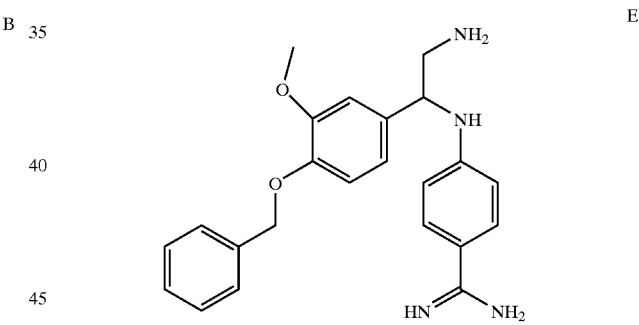

E

4-[2-Amino-1-(4-benzyloxy-3-methoxy-phenyl)-ethylamino]-benzonitrile D (300 mg, 0.8 mmoles) was dissolved in ethanol (3 ml) and hydroxylamine-hydrochloride (350 mg, 5 mmoles) and triethylamine (1 ml, 5.7 mmoles) were added. The reaction was heated to 65–70 degrees C. for 2 hours. The residue was taken up in ethyl acetate and water. The organic layer was separated, dried over anhydrous sodium sulfate and filtered. The solvent was removed in vacuo and replaced with 4 ml methanol with 0.5 ml acetic acid. Raney nickel (ca. 300 ul suspension in sodium hydroxide, Aldrich) was added and the reaction placed under a hydrogen atmosphere. The reaction was stirred vigorously for 3 hours, the catalyst filtered off and the solvent removed in vacuo. The crude product was purified by flash chromatography on silica gel (ethyl acetate:acetone:methanol: ammonia, 2:1:1:0.05) to yield 160 mgs of 4-[2-Amino-1-(4-benzyloxy-3-methoxy-phenyl)-ethylamino]-benzamidine E. MS (M+H)=391.

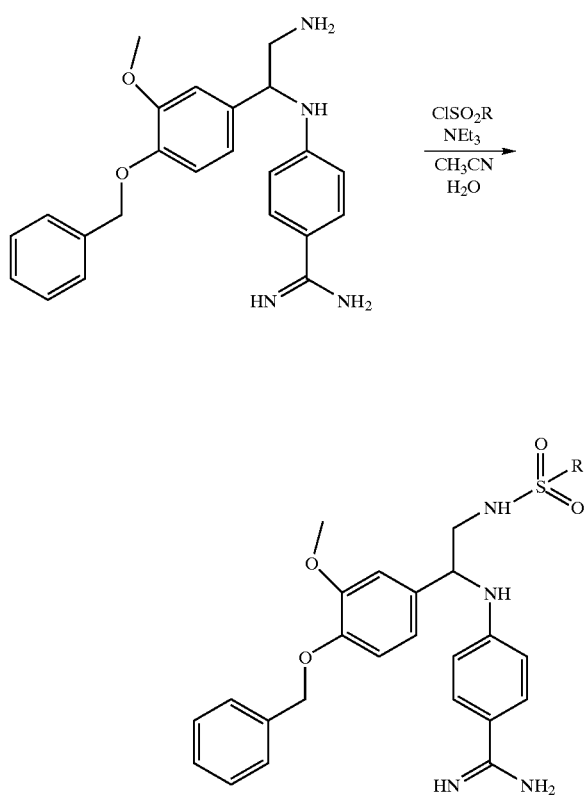

4-[2-Amino-1-(4-benzyloxy-3-methoxy-phenyl)-ethylamino]-benzamidine E (20 mg, 0.03 mmoles) was dissolved in acetonitrile (2 ml) containing triethylamine (17 ul, 0.12 mmoles) and water (0.3 ml). To this was added the desired sulfonyl chloride having a formula ClSO$_2$R (0.03 mmoles) and the reaction stirred for 4 hours. The solvent was removed in vacuo and the compounds purified by reverse-phase preparative HPLC (gradient acetonitrile/water with 0.1% trifluoroacetic acid) to yield the final product upon lyophilization.

Examples 2a–2dd

Using an analogous procedure, other compounds of the invention were prepared, including:

a) 4-[Benzenesulfonylamino-1-(4-benzyloxy-3-methoxy-phenyl)-ethylamino]-benzamidine: MS (M+H)=531, b) N-{4-[2-(4-Benzyloxy-3-methoxy-phenyl)-2-(4-carbamimidoyl-phenylamino)-ethylsulfamoyl]-phenyl}-acetamide: MS (M+H)=588, c) 4-[1-(4-Benzyloxy-3-methoxy-phenyl)-2-(4-nitro-benzenesulfonylamino)-ethylamino]-benzamidine: MS (M+H)=576, d) 4-[1-(4-Benzyloxy-3-methoxy-phenyl)-2-(4-fluoro-benzenesulfonylamino)-ethylamino]-benzamidine: MS (M+H)=549, e) 4-[1-(4-Benzyloxy-3-methoxy-phenyl)-2-(4-fluoro-benzenesulfonylamino)-ethylaminol]-benzamidine: MS (M+H)=565, f) 4-[1-(4-Benzyloxy-3-methoxy-phenyl)-2-(3-nitro-benzenesulfonylamino)-ethylamino]-benzamidine: MS (M+H)=576, g) 4-[1-(4-Benzyloxy-3-methoxy-phenyl)-2-(2,5-dichloro-benzenesulfonylamino)-ethylamino]-benzamidine: MS (M+H)=599, h) 4-[1-(4-Benzyloxy-3-methoxy-phenyl)-2-(2-bromo-benzenesulfonylamino)-ethylamino]-benzamidine: MS (M+H)=609, 611, i) 4-[1-(4-Benzyloxy-3-methoxy-phenyl)-2-(4-bromo-benzenesulfonylamino)-ethylamino]-benzamidine: MS (M+H)=609, j) 4-[1-(4-Benzyloxy-3-methoxy-phenyl)-2-(4-isopropyl-benzenesulfonylamino)-ethylamino]-benzamidine: MS (M+H)=573, k) 4-[1-(4-Benzyloxy-3-methoxy-phenyl)-2-phenylmethanesulfonylamino-ethylaminol]-benzamidine: MS (M+H)=545, l) 4-[1-(4-Benzyloxy-3-methoxy-phenyl)-2-(4-carboxy-benzenesulfonylamino)-ethylamino]-benzamidine: MS (M+H)=575, m) 4-[1-(4-Benzyloxy-3-methoxy-phenyl)-2-(3-carboxy-benzenesulfonylamino)-ethylamino]-benzamidine: MS (M+H)=575, n) 4-[1-(4-Benzyloxy-3-methoxy-phenyl)-2-(2,4-dinitro-benzenesulfonylamino)-ethylamino]-benzamidine: MS (M+H)=621, o) 4-[1-(4-Benzyloxy-3-methoxy-phenyl)-2-(2,3,5,6-tetramethyl-benzenesulfonylamino)-ethylamino]-benzamidine: MS (M+H)=587, p) 4-[1-(4-Benzyloxy-3-methoxy-phenyl)-2-(3,5-dichloro-2-hydroxy-benzenesulfonylamino)-ethylamino]-benzamidine: MS (M+H)=615, q) 4-[1-(4-Benzyloxy-3-methoxy-phenyl)-2-(3,4-dimethoxy-benzenesulfonylamino)-ethylamino]-benzamidine: MS (M+H)=591, r) 4-[1-(4-Benzyloxy-3-methoxy-phenyl)-2-(thiophene-2-sulfonylamino)-ethylamino]-benzamidine: MS(M+H)=537, s) N-{5-[2-(4-Benzyloxy-3-methoxy-phenyl)-2-(4-carbamimidoyl-phenylamino)-ethylsulfamoyl]-4-methyl-thiazol-2-yl}-acetamide: MS(M+H)=595, t) 4-[1-(4-Benzyloxy-3-methoxy-phenyl)-2-(naphthalene-2-sulfonylamino)-ethylamino]-benzamidine: MS (M+H)=581, u) 4-[1-(4-Benzyloxy-3-methoxy-phenyl)-2-(naphthalene-1-sulfonylamino)-ethylamino]-benzamidine: MS (M+H)=581, v) 4-[1-(4-Benzyloxy-3-methoxy-phenyl)-2-(2-phenyl-ethenesulfonylamino)-ethylamino]-benzamidine: MS (M+H)=557, w) 4-[1-(4-Benzyloxy-3-methoxy-phenyl)-2-(3-trifluoromethyl-benzenesulfonylamino)-ethylamino]-benzamidine: MS (M+H)=599, x) 4-[1-(4-Benzyloxy-3-methoxy-phenyl)-2-(2,3,4,5,6-pentafluoro-benzenesulfonylamino)-ethylamino]-benzamidine: MS (M+H)=521, y) 4-[1-(4-Benzyloxy-3-methoxy-phenyl)-2-methanesulfonylamino-ethlylamino]-benzamidine: MS(M+H)=469, z) 4-[1-(4-Benzyloxy-3-methoxy-phenyl)-2-ethanesulfonylamino-ethylamino]-benzamidine: MS(M+H)=483, aa) 4-[1-(4-Benzyloxy-3-methoxy-phenyl)-2-propanesulfonylamino-ethylamino]-benzamidine: MS(M+H)=497, bb) 4-[1-(4-Benzyloxy-3-methoxy-phenyl)-2-butanesulfonylamino-ethylamino]-benzamidine: MS(M+H)=511, cc) [2-(4-Benzyloxy-3-methoxy-phenyl)-2-(4-carbamimidoyl-phenylamino)-ethylsulfamoyl]-acetic acid ethyl ester MS (M+H)=541, dd) [2-(4-Benzyloxy-3-methoxy-phenyl)-2-(4-carbamimidoyl-phenylamino)-ethylsulfamoyl]-acetic acid.

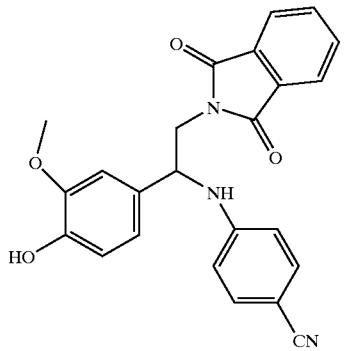

4-[1-(4-Benzyloxy-3-methoxy-phenyl)-2-(1,3-dioxo-1,3-dihydro-isoindol-2-yl)-ethylamino]-benzonitrile B (1.8 g) was dissolved in a mixture of ethanol (50 ml), acetic acid (3 ml), methanol (5 ml), and ethyl acetate (5 ml). This solution was added to a Parr flask containing 10% Pd/C (500 mg) and hydrogenated at 35 psi for 16 hours. The catalyst was removed by filtration through Celite and the solvent removed in vacuo to provide 1 g of the product 4-[2-(1,3-Dioxo-1,3-dihydro-isoindol-2-yl)-1-(4-hydroxy-3-methoxy-phenyl)-ethylamino]-benzonitrile (68%).

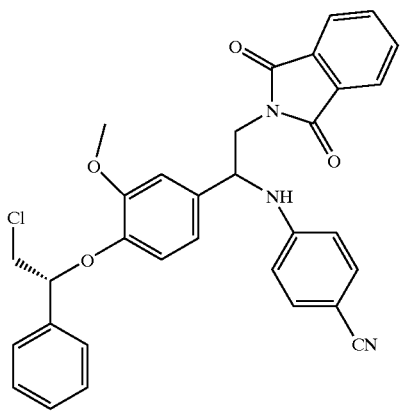

4-[2-(1,3-Dioxo-1,3-dihydro-isoindol-2-yl)-1-(4-hydroxy-3-methoxy-phenyl)-ethylamino]-benzonitrile (1 g, 2.43 mmoles) was dissolved in tetrahydrofuran (30 ml) and triphenylphosphine (1.27 g, 4.84 mmoles), (S)-2-chloro-1-phenyl-ethanol (1.13 g, 7.26 mmoles) added. The reaction was cooled to 0° C. and diethylazodicarboxylate (0.842 g, 4.8 mmoles) added. The reaction temperature was allowed to come to room temperature and the reaction stirred for 2.5 hours. The solvent was removed in vacuo and the residue taken up in ethyl acetate, washed with 0.5 N sodium hydroxide several times, washed once with brine and dried over anhydrous sodium sulfate. The crude product was purified by flash chromatography on silica gel (30% ethyl acetate in hexanes) to yield 1.1 g of 4-[1-[4-(2-chloro-1-phenyl-ethoxy)-3-methoxy-phenyl]-2-(1,3-dioxo-1,3-dihydro-isoindol-2-yl)-ethylamino]-benzonitrile, (82%).

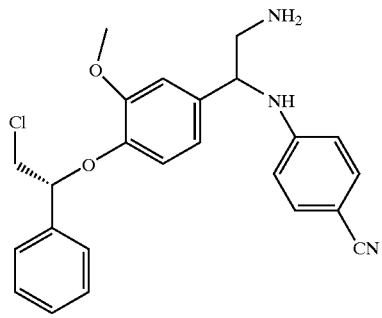

4-[1-[4-(2-Chloro-1-phenyl-ethoxy)-3-methoxy-phenyl]-2-(1,3-dioxo-1,3-dihydro-isoindol-2-yl)-ethylamino]-benzonitrile (0.5 g) was dissolved in ethanol (40 ml) and hydrazine hydrate (0.14 g) added. The reaction was heated at 65° C. for 2 hours. The solvent was removed and replaced with ethyl acetate. The solution was washed twice with water and once with brine. The solution was dried over anhydrous sodium sulfate and the solvent removed in vacuo to yield 318 mg of desired amine 4-{2-Amino-1-[4-(2-chloro-1-phenyl-ethoxy)-3-methoxy-phenyl]-ethylamino}-benzonitrile, (83%).

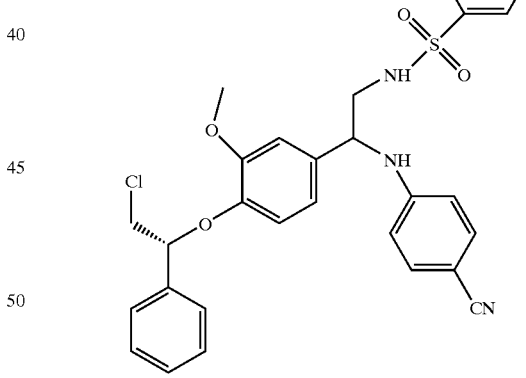

4-{2-Amino-1-[4-(2-chloro-1-phenyl-ethoxy)-3-methoxy-phenyl]-ethylamino}-benzonitrile, (0.1 g, 0.237 mmoles) was dissolved in dichloromethane (6 ml) and triethylamine (34 ul, 0.3 mmoles) added. Phenyl sulfonyl-chloride (46 ul, 0.26 mmoles) was added and the reaction stirred for 90 minutes. The reaction was diluted with dichloromethane and washed once with sat. sodium bicarbonate and once with water. The solution was dried over sodium sulfate and the solvent removed in vacuo. The product was purified by silica gel to yield 100 mg of desired product N-[2-[4-(2-chloro-1-phenyl-ethoxy)-3-methoxy-phenyl]-2-(4-cyano-phenylamino)-ethyl]-benzenesulfonamide.

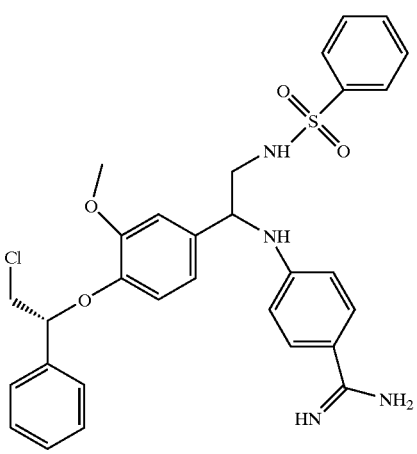

N-[2-[4-(2-chloro-1-phenyl-ethoxy)-3-methoxy-phenyl]-2-(4-cyano-phenylamino)-ethyl]-benzenesulfonamide (100 mg 0.18 mmoles) was dissolved in ethanol (3 ml) and hydroxylamine-hydrochloride (62 mg, 0.89 mmoles) added. To this was added triethylamine (90 mg, 0.89 mmoles) and later potassium carbonate (62 mg). The reaction was heated to 80° C. for 48 hours. The reaction was cooled and the solvent removed in vacuo. The residue was taken up in ethyl acetate and washed twice with water and once with brine. The solution was dried over sodium sulfate and the solvent removed. The crude intermediate was dissolved in methanol (4 ml) and a few drops of acetic acid added. Approximately 50–100 mg of Raney nickel suspended in sodium hydroxide (Aldrich) was added and the reaction placed under an atmosphere of hydrogen. The suspension was stirred vigorously for 8 hours, the catalyst filtered off and the solvent removed in vacuo. The crude product was purified by reverse-phase chromatography to yield 4-{2-benzenesulfonylamino-1-[4-(2-chloro-1-phenyl-ethoxy)-3-methoxy-phenyl]-ethylamino}-benzamidine (32 mg). MS(M+H)=579.

Example 4

4-{2-propanesulfonylamino-1-[4-(2-chloro-1-phenyl-ethoxy)-3-methoxy-phenyl]-ethylamino}-benzamidine was prepared similarly to Example 2, except propanesulfonyl chloride was substituted for benzenesulfonyl chloride in the reaction with 4-{2-amino-1-[4-(2-chloro-1-phenyl-ethoxy)-3-methoxy-phenyl]-ethylamino}-benzonitrile. MS(M+H)= 545.

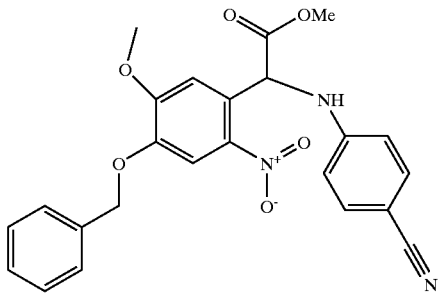

4-Benzyloxy-5-methoxy-2-nitrobenzaldehyde (12.2 g 42 mmoles) and 4-aminobenzonitrile (5 g, 42 mmoles) were dissolved in methanol (165 ml) and stirred for two hours and then heated to 60° C. for 30 minutes. The reaction was allowed to cool to room temperature and benzyl isonitrile (5 g. 42 mmoles) added. The reaction was cooled to 0° C. and boron trifluoroetherate (16 ml, 126 mmoles) added dropwise over five minutes. The reaction was stirred at 0° C. for 20 minutes and then allowed to come to room temperature and then stirred at ambient temperature for two hours. Water (4 ml) was added and the mixture stirred at room temperature overnight. A yellow precipitate was evident the next morning and the solid filtered off. The solid was washed with methanol and air dried to yield 8 grams of the desired product. The solvent from the filtrate was removed in vacuo and replaced with ethyl acetate. The solution was washed with water and saturated sodium bicarbonate, dried over anhydrous magnesium sulfate and the solvent removed. The crude material was submitted to flash chromatography (hexanes: ethyl acetate, 1:1) to yield an additional 7 g of the desired product (4-Benzyloxy-5-methoxy-2-nitro-phenyl)-(4-cyano-phenylamino)-acetic acid methyl ester. $^1$HNMR (CDCl$_3$): 7.68 (s, 1H), 7.4 (m, 7H), 7.0 (s, 1H), 6.61 (d, 2H), 6.2 (s, 1H), 5.2 (s,2H), 3.87 (s, 3H), 3.75 (s, 3H).

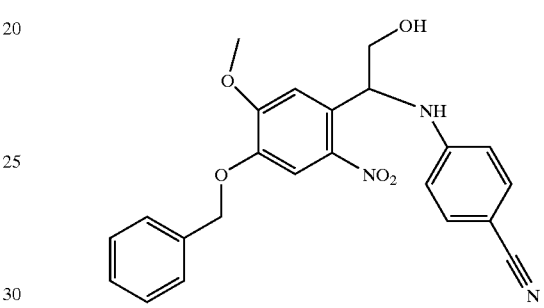

(4-Benzyloxy-5-methoxy-2-nitro-phenyl)-(4-cyano-phenylamino)-acetic acid methyl ester (4.5 g, 10 mmole) was dissolved in dimethoxyethane and lithium borohydride (0.210 g, 10 mmole) added. The reaction was heated to reflux for three hours and cooled to room temperature. The reaction was quenched with water containing acetic acid and diluted with ethyl acetate. After transferring to a separatory funnel, the organic layer was washed with water several times. The organic layer was dried over anhydrous sodium sulfate, filtered and the solvent removed. The crude material was then submitted to flash chromatography to yield 3.1 g of 4-[1-(4-Benzyloxy-5-methoxy-2-nitro-phenyl)-2-hydroxy-ethylamino]-benzonitrile (74%).

$^1$HNMR(CDCl$_3$): 7.77 (s, 1H), 7.3–7.5 (m, 7H), 7.15 (s, 1H), 6.42 (d, 2H), 5.4 (bs, 1H), 5.18 (dd AB syst., 2H), 4.15 (dd, 1H), 3 83 (s, 3H), 3.79–3.86 (dd, 1H)

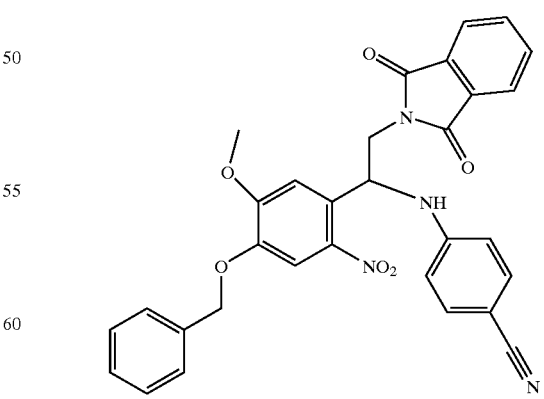

4-[1-(4-Benzyloxy-5-methoxy-2-nitro-phenyl)-2-hydroxy-ethylamino]-benzonitrile (3.1 g, 7.4 mmoles) was dissolved in tetrahydrofuran (120 ml) and triphenylphosphine (5.9 g, 22 mmoles) and phthalimide (5.4 g, 37 mmoles) added. The reaction was cooled to 0 C and diisopropylazadicarboxylate (DIAD, 4.6 g) added dropwise. The reaction was allowed to come to room temperature and stirred overnight. The solvent was removed in vacuo and replaced with ethyl acetate. The solution was washed with 1 N NaOH several times and dried over anhydrous sodium sulfate. Flash chromatography (hexanes:ethyl acetate, 1:1) provided the desired material with some DIAD still present. The solid was washed several times with ethanol to yield 3.2 g of the desired phthalimide 4-[1-(4-Benzyloxy-5-methoxy-2-nitro-phenyl)-2-(1,3-dioxo-1,3-dihydro-isoindol-2-yl)-ethylamino]-benzonitrile (3.2 g,). $^1$HNMR(CDCl$_3$): 7.83 (m, 2H), 7.75 (m, 2H), 7.37 (m, 7H), 6.91 (s, 1H), 6.41 (d, 2H), 6.17 (d, 1H), 5.65 (m, 1H), 5.18 (s, 2H), 4.27 (m, 2H), 3.61 (s, 3H).

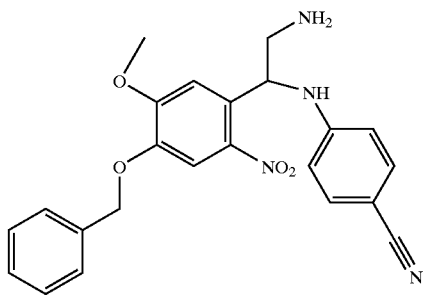

4-[1-(4-Benzyloxy-5-methoxy-2-nitro-phenyl)-2-(1,3-dioxo-1,3-dihydro-isoindol-2-yl)-ethylamino]-benzonitrile (2.7 g, 5 mmoles) was dissolved in ethanol (100 ml) and hydrazine hydrate (0.65 ml, 20 mmoles) added. The reaction was heated to 60° C. for 3 hours then at room temperature for 48 hours. The solids that precipitated were filtered off and the residue submitted to flash chromatography to yield 4-[2-Amino-1-(4-benzyloxy-5-methoxy-2-nitro-phenyl)-ethylamino]-benzonitrile (1.5 g). $^1$HNMR(CDCl$_3$): 7.75 (s,1H), 7.3–7.5 (m, 7H), 7.05 (s,1H), 6.45 (d, 2H), 5.80 (bs, 1H), 5.32 (m, 1H), 5.19 (s, 2H), 3.81 (s, 3H), 3.25 (dd, 1H), 3.0 (dd, 1H), 1.65 (bs, 2H).

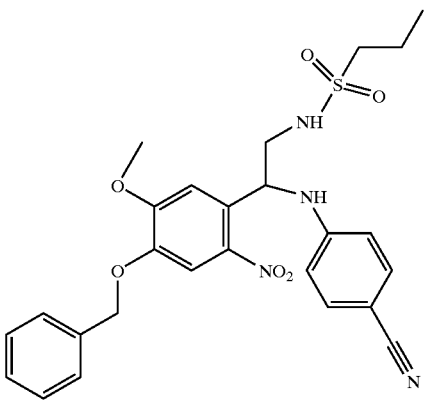

4-[2-Amino-1-(4-benzyloxy-5-methoxy-2-nitro-phenyl)-ethylamino]-benzonitrile (0.227 g, 0.66 mmoles) was dissolved in dichloromethane (4 ml) and triethylamine (0.14 ml, 1 mmoles). The reaction was cooled to 0C and 1-propanesulfonyl chloride (0.085 ml, 0.75 mmoles). The reaction was stirred for 20 minutes and the product purified by flash chromatography (hexanes:ethyl acetate 1:1) to yield 260 mg of desired product—propane-1-sulfonic acid [2-(4-benzyloxy-5-methoxy-2-nitro-phenyl)-2-(4-cyano-phenylamino)-ethyl]-amide. $^1$HNMR(CDCl$_3$): 7.77 (s, 1H), 7.3–7.5 (m, 7H), 7.12 (s, 1H), 6.41 (d, 2H), 6.0 (d, 1H), 5.3 (m, 1H), 5.17 (dd, A–B, 2H),4.75 (t, 1H), 3.85 (s, 3H), 3.65 (m, 1H), 3.5 (m, 1H), 3.04 (n, 2H), 1.83 (m, 2H), 1.05 (t, 3H).

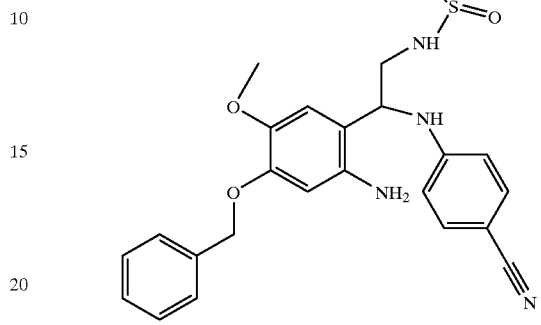

Propane-1-sulfonic acid [2-(4-benzyloxy-5-methoxy-2-nitro-phenyl)-2-(4-cyano-phenylamino)-ethyl]-amide (0.250 g) was dissolved in ethanol (10 ml) and added to Pt/C (5%). The reaction was placed under a hydrogen atmosphere and stirred vigorously for 3 hours. The catalyst was filtered off and the product chromatographed (hexanes:ethyl acetate 1:2) to yield 133 mg of Propane-1-sulfonic acid [2-(2-amino-4-benzyloxy-5-methoxy-phenyl)-2-(4-cyano-phenylamino)-ethyl]-amide. $^1$HNMR(CDCl$_3$): 7.3–7.45 (m, 7H), 6.71 (s, 1H), 6.52 (d, 2H), 6.3 (s, 1H), 5.33 (2, 1H), 5.08 (s, 2H), 5.0 (t, 1H), 4.42 (q, 1H), 3.75 (s, 3H), 3.70 (bs, 2H), 3.45 (t, 2H), 2.97 (m, 2H), 1.80 (m, 2H), 1.03 (t, 3H).

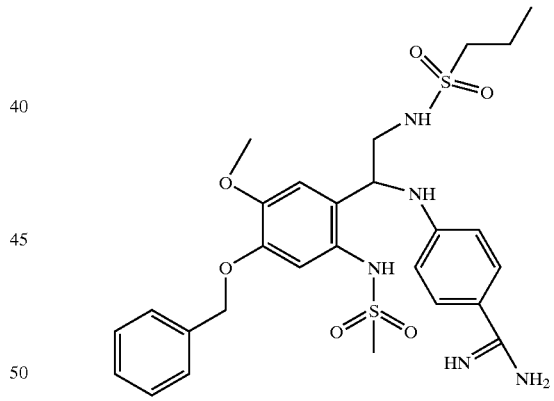

Propane-1-sulfonic acid [2-(2-amino-4-benzyloxy-5-methoxy-phenyl)-2-(4-cyano-phenylamino)-ethyl]-amide (133 mg, 0.27 mmoles) was dissolved in dichloromethane and triethylamine added (0.05 ml, 0.35 mmoles). The reaction was cooled and methanesulfonyl chloride (0.023 ml, 0.3 mmoles) added dropwise The reaction was stirred for two hours and the product purified by flash chromatography (hexanes:ethyl acetate, 1:1). The product was then taken-up in ethanol and hydroxylamine hydrochloride (35 mg, 0.5 mmoles) added. Sodium ethoxide (48 mg, 0.7 mmoles was added and the reaction heated for 48 hours. The ethanol was removed and water (4 ml) added. The solid was filtered off and washed with water. The crude product was then taken up in 4 ml of methanol with 0.5 ml acetic acid. Raney Nickel (ca. 50 mg as a suspension in sodium hydroxide, Aldrich)

was added and the reaction placed under a hydrogen atmosphere. The reaction was stirred vigorously for 3 hours and the catalyst filtered off. The crude product was submitted to reverse-phase preparative chromatography to yield the final product 4-[1-(4-Benzyloxy-2-methanesulfonylamino-5-methoxy-phenyl-2-(propane-1-sulfonylamino)-ethylamino]-benzamidine (12 mg): MS (M+H)=590.

Example 6a–6g

Using a procedure analogous to Example 5, the following compounds were prepared:

a) 4-[2-Benzenesulfonylamino-1-(2-benzenesulfonylamino-4-benzyloxy-5-methoxy-phenyl)-ethylamino]-benzamidine. The procedure was the same as above except phenyl sulfonyl chloride was used instead of propanesulfonyl chloride and methane sulfonyl chloride. MS: (M+H)=686.

b) 4-[2-Benzenesulfonylamino-1-(2-benzenesulfonylamino-4-benzyloxy-5-ethoxy-phenyl)-ethylamino]-benzamidine. The procedure was the same as above except starting with 3-ethoxy, 4-benzyloxy, 6-nitro-benzaldehyde. MS: (M+H)=700.

c) 4-[1-(4-Benzyloxy-5-ethoxy-2-methanesulfonylamino-phenyl)-2-(propane-1-sulfonylamino)-ethylamino]-benzamidine. The procedure was the same as above except starting with 3-ethoxy, 4-benzyloxy, 6-nitrobenzaldehyde. MS (M+H)=604.

d) 4-[1-(4,5-Diethoxy-2-methanesulfonylamino-phenyl)-2-(propane-1-sulfonylamino)-ethylamino]-benzamidine. The procedure was the same except starting with 3,4-diethoxy, 6-nitrobenzaldehyde. MS (M+H)=542.

e) {5-Benzyloxy-2-[1-(4-carbamimidoyl-phenylamino)-2-(propane-1-sulfonylamino)-ethyl]-4-methoxy-phenylsulfamoyl}-acetic acid ethyl ester. The procedure was the same except using chlorosulfonyl-acetic acid ethyl ester instead of methanesulfonyl chloride. MS: (M+H)=676.

f) {5-Benzyloxy-2-[1-(4-carbamimidoyl-phenylamino)-2-(propane-1-sulfonylamino)-ethyl]-4-methoxy-phenylsulfamoyl}-acetic acid. {5-Benzyloxy-2-[1-(4-carbamimidoyl-phenylamino)-2-(propane-1-sulfonylamino)-ethyl]-4-methoxy-phenylsulfamoyl}-acetic acid ethyl ester (10 mg) was dissolved in water (2 ml) and tetrahydrofuran (2 ml) and LiOH added (3 mg). Allowed to stir overnight. Product purified by reverse-phase preparative HPLC. 3 mg MS (M+H)=648.

g) 4-[1-(3,4-Dimethoxy-2-methanesulfonylaminophenyl)-2-(propane-1-sulfonylamino)-ethylamino]-benzamidine. This compound was prepared with a similar procedure as described above except 2-bromo-3,4-dimethoxybenzaldehyde was used instead of 4-benzyloxy-5-methoxy-2-nitrobenzaldehyde. MS(M+H)=499.

Examples 7a–7g

The compounds 7a–7g were generally prepared as follows. Compound E (20 mg, 0.03 mmoles) was dissolved in acetonitrile (2 ml) containing triethylamine (17 ul, 0.12 mmoles) and water (0.3 ml). To this was added the respective acyl chloride, alkyl chloroformate, or isocyanate (0.03 mmoles) and the reaction stirred for 4 hours. The solvent was removed in vacuo and the compounds purified by reverse-phase preparative HPLC (acetonitrile/water with 0.1% trifluoroacetic acid) to yield the final product upon lyophilization.

7a: N-[2-(4-Benzyloxy-3-methoxy-phenyl)-2-(4-carbamimidoyl-phenylamino)-ethyl]-2,2,2-trifluoro-acetamide, MS (M+H)=487.

7b: N-[2-(4-Benzyloxy-3-methoxy-phenyl)-2-(4-carbamimidoyl-phenylamino)-ethyl]-acetamide, MS (M+H)=433.

7c: N-[2-(4-Benzyloxy-3-methoxy-phenyl)-2-(4-carbamimidoyl-phenylamino)-ethyl]-butyramide, MS (M+H)=461.

7d: N-[2-(4-Benzyloxy-3-methoxy-phenyl)-2-(4-carbamimidoyl-phenylamino)-ethyl]-2-chloro-acetamide, MS (M+H)=467.

7e: [2-(4-Benzyloxy-3-methoxy-phenyl)-2-(4-carbamimidoyl-phenylamino)-ethyl]-carbonic acid methyl ester, MS (M+H)=449.

7f: [2-(4-Benzyloxy-3-methoxy-phenyl)-2-(4-carbamimidoyl-phenylamino)-ethyl]-carbonic acid isobutyl ester, MS (M+H)=491.

7g: [2-(4-Benzyloxy-3-methoxy-phenyl)-2-(4-carbamimidoyl-phenylamino)-ethyl]-carbonic acid 2,2,2-trichloro-ethyl ester, MS (M+H)=565

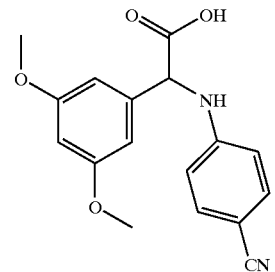

The methyl ester of the acid shown above (920 mg 2.85 mmoles) was suspended in 3/1 THF/water (40 ml) and cooled to 0° C. The solution was treated with 1N LiOH (7.1 ml, 7.1 mmoles) and allowed to stir overnight. The reaction was acidified with trifluoroacetic acid until pH=4.0 was obtained The solvent was removed in vacuo and the crude material purified by flash chromatography (ethyl acetate with 0.5% acetic acid) to yield 1 g of carboxylic acid.

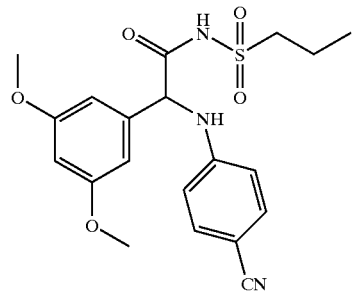

Carbonyl diimidazole (131 mg, 0.8 mmoles) was dissolved in anhydrous THF (1.6 ml) and the carboxylic acid prepared above (251 mg, 0.8 mmoles) added dropwise as a solution in THF (1.6 ml). The reaction was allowed to stir at room temperature for 30 minutes, refluxed for 30 minutes and then cooled to room temperature again. n-Propylsulfonamide (100 mg) was added and stirred for 10 minutes. DBU (123 mg) was added as a solution in THF (1.6 ml). The reaction was worked up by acidification and extraction into ethyl acetate. The solvent was removed and the crude product purified by flash chromatography (SiO2, ethyl acetate) to yield 195 mg of the acyl sulfonamide shown above.

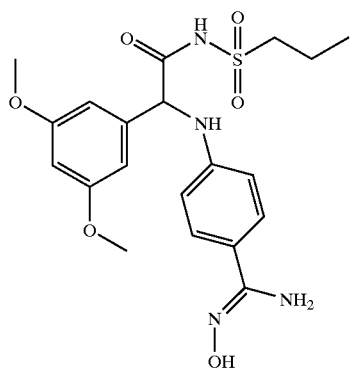

The nitrile prepared above (90 mg, 0.2 mmoles) was dissolved in ethanol (2.5 ml). Diisopropylethylamine (202 mg, 1.56 mmoles) was added followed by hyroxylamine hydrochloride (83 mg, 1.2 mmoles). The reaction was heated to 70° C. for 21 hours. The reaction was cooled and the solvent removed in vacuo. The residue was taken up in 30% acetonitrile/water (4 ml) and purified by preparative reverse-phase chromatography (water/acetonitrile 0.1% TFA gradient) to yield 14 mg of the hydroxyamidine shown above.

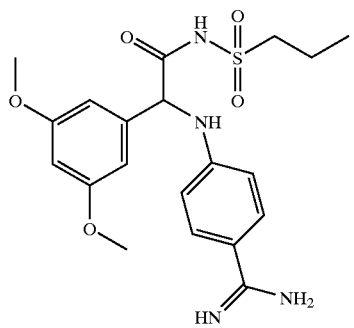

The hydroxyamidine product was then taken up in ethanol (2 ml) and acetic acid (8 drops). Raney Ni (ca. 100 mg) was added and the reaction stirred vigorously under a hydrogen atmosphere for 2 hours 45 minutes. The product was filtered through Celite and the Celite rinsed first with 30% acetonitrile/water containing 0.1% TFA and then with acetonitrile. The solvent was removed in vacuo and the crude product purified by preparative reverse-phase chromatography (water/acetonitrile 0.1% TFA gradient) to yield the desired product (6 mg). M+H=435.

Example 9

Synthesis of Enantiomerically Pure 6-alkylsulfonylamino sulfonamides

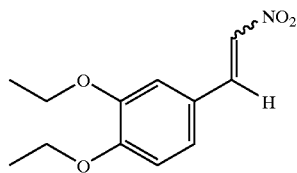

3-Ethoxy-4-hydroxybenzaldehyde (40 g) was added to dimethylformamide (600 mL) followed by potassium carbonate (40 g, 1.2 Equiv.). Ethyl iodide (28.87 mL, 1.5 Equiv.) was added and the solution was heated to 60° C. for six hours. The solution was cooled to room temperature and the solvent was removed under reduced pressure. The solution was diluted with ethyl acetate (500 mL), and washed with water, brine, dried with magnesium sulfate, and evaporated to yield the crude product 3,4-ethoxybenzaldehyde (49 g, 104%). The 3,4-ethoxybenzaldehyde (45 g) was dissolved in ethanol (300 mL), and the solution was cooled to 0° C. In a separate flask, potassium hydroxide (19.5 g, 1.5 Equiv.) was added to ethanol (300 mL) followed by nitromethane (26 g, 1.5 Equiv.) and the solution was stirred at room temperature for ten minutes and cooled to 0° C. This solution was added to the 3,4-ethoxybenzaldehyde and stirred for 20 minutes and poured onto concentrated hydrochloric acid (200 mL) at 0° C. The ethanol was removed under reduced pressure, and the solution was diluted with water (300 mL) and the reaction mixture was extracted with ethyl acetate. The organic layer was dried with magnesium sulfate and the solvent removed to yield crude product. The crude product was purified by recrystallization with ethyl acetate (47 g, 87%). MS (M+H)=238.

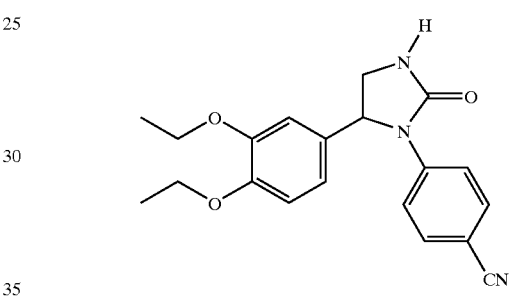

The 1-nitro-2-(3,4-diethoxyphenyl)ethylene (16.64 g) and 4-aminobenzonitrile (9.12 g, 1.1 Equiv.) were added to tetrahydrofuran (350 mL), and cooled to 0° C. Lithium diisopropylamide (47.8 mL, 1.02 Equiv.) was added slowly until a persistent purple color was formed. Zinc (50 g) was added in one portion, followed by acetic acid (35 mL). The solution was warmed to room temperature and stirred for 2 hours followed by the addition of acetic acid (35 mL) and zinc (10 g) After an additional 2 hours, acetic acid (25 mL) was added and the reaction mixture was stirred for one hour. Concentrated hydrochloric acid (15 mL) was added and the solution was stirred an additional hour. The solution was filtered through a pad of celite and water (250 mL) was added. The solution was concentrated to 300 mL under reduced pressure and added to citric acid (0.5 M, 500 mL) and ethyl acetate/hexane (500 mL). The citric acid layer was collected and ammonium hydroxide was added until the solution became basic. This solution was extracted with ethyl acetate (3×200 mL), and the combined organics were dried with magnesium sulfate, and evaporated under reduced pressure to yield the crude product. The crude product was diluted with dichloromethane (350 mL) and cooled to 0° C. Phosgene (40.88 mL of a 20% solution in toluene, 1.1 Equiv.) was added followed by Hunigs base (24.46 mL, 2 Equiv.). The solution was stirred for ten minutes and water (200 mL) was added. The dichloromethane was collected, dried with magnesium sulfate, and purified by flash chromatography on silica gel (80% ethyl acetate/20% hexane) to yield the product as a white solid (9.76 g, 40%). MS (M+H) =352.

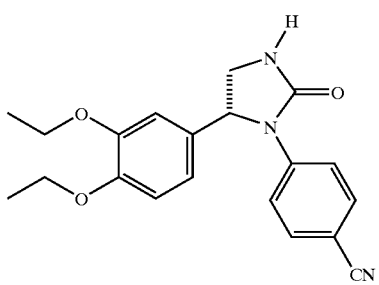

The 4-[5-(3,4-diethoxyphenyl)-2-oxo-imidazolidin-1-yl-benzonitrile (2.10 g) was added to tetrahydrofuran (200 mL) and cooled to −78° C. n-Butyllithium (3.74 mL, 1 Equiv.) was added dropwise, and the solution stirred for ten minutes. (S)-(+)-2-(6-methoxy-2-naphthyl)propionyl chloride (1.49 g, 1 Equiv.) was added in one portion as a solid and the reaction was stirred for one hour. The reaction mixture was warmed to room temperature, and evaporated under reduced pressure to 50 mL. The solution was diluted with ethyl acetate (300 mL), and washed with citric acid (0.5M), water, brine, and dried with magnesium sulfate. The solution was evaporated under reduced pressure and purified by flash chromatography on silica gel (50% ethyl acetate/50% hexane) to yield the product 4-{5-(3,4-diethoxyphenyl)-3-[2-(6-methoxynaphthalen-2-yl)-propionyl]-2-oxo-imidazolidin-1-yl}-benzonitrile as one diastereomer (1.20 g, 71%). This product was added to methanol (200 mL) followed by lithium hydroxide (1 mL of a 10% aqueous solution) and stirred for fifteen minutes. Acetic acid (10 drops was added, the methanol was removed under reduced pressure and the product was purified by flash chromatography on silica gel (80% ethyl acetate/20% hexane) to yield the product (0.71 g, 95%) as a white solid. $[\alpha]_{Na}$-55.0 (c 2.20, acetone). MS (M+H)=352.

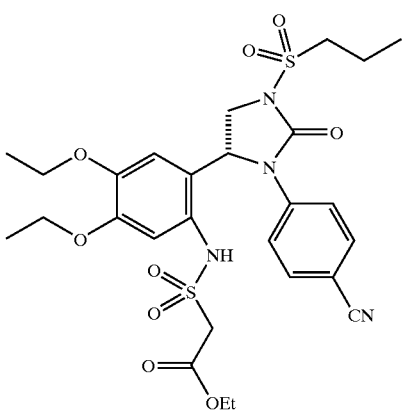

The (R)-(−)-4-[5-(3,4-diethoxyphenyl)-2-oxo-imidazolidin-1-yl-benzonitrile (0.710 g) was added to tetrahydrofuran (20 mL) and cooled to −78° C. n-Butyllithium (1.27 mL of a 1.6 M solution in hexane, 1 Equiv.) was added dropwise and the solution was stirred for ten minutes. 1-Propylsulfonylchloride (0.275 mL, 1.2 Equiv.) was added and the solution was stirred for fifteen minutes and warmed to room temperature. Acetic acid (10 drops) was added, the solvent removed under reduced pressure, and the product was purified by flash chromatography on silica gel (50% ethyl acetate/50% hexane) to yield the product (0.740 g, 80%). This material (0.300 g) was diluted with dichloroethane (10 mL) and cooled to 0° C. Nitric acid (0.137 mL, 5 Equiv.) was added dropwise and the solution was stirred for one hour. The solution was diluted with dichloroethane (100 mL), and washed with water, saturated sodium bicarbonate, dried with magnesium sulfate, and the solvent was evaporated under reduced pressure. This material was diluted with methanol (50 mL), and acetic acid (1 mL), and platinum (0.050 g, 5% on carbon) was added. The solution was hydrogenated for one hour, filtered through a pad of celite, and the solvent was evaporated under reduced pressure. This material was dissolved in dichloromethane (5 mL), and Hunigs base (0.177 mL, 1.5 Equiv.) and chlorosulfonylacetic acid ethyl ester (0.189 g, 1.5 Equiv.) was added and the solution was stirred for two hours. The solution was purified by direct flash chromatography on silica gel (50% ethyl acetate/50% hexane) to yield the product (0.160 g) (R)-{2-[3-(4-cyanophenyl)-2-oxo-1-(propane-1-sulfonyl)-imidazolidin-4yl]-4,5-diethoxyphenylsulfamoyl}-acetic acid ethyl ester. MS (M+H)=624.

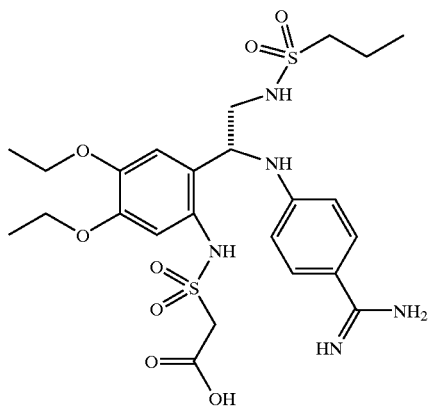

(R)-{2-[3-(4-cyanophenyl)-2-oxo-1-(propane-1-sulfonyl)-imidazolidin-4-yl]-4,5-diethoxyphenylsulfamoyl}-acetic acid ethyl ester (0.160 g) was diluted with ethanol (5 mL) followed by lithium hydroxide (1 mL of a 10% aqueous solution, 10 Equiv.) and the solution was stirred for forty eight hours. The solution was purified by direct flash chromatography on silica gel (20% methanol/80% dichloromethane) to yield the product. This product was diluted with ethanol (1 mL) and hydroxylamine (0.035 g, 10 Equiv.) and Hunigs base (0.088 mL, 10 Equiv.) was added and the solution was heated to 60° C. for six hours. The reaction mixture was cooled to room temperature and stirred for twelve hours. Ethanol (3 mL) and acetic acid (0.5 mL), and Raney nickel (0.025 g) was added and the solution was hydrogenated for one hour. The reaction mixture was filtered through a pad of celite and the solvent was removed under reduced pressure. The product was purified by reverse-phase preparative chromatography to yield {2-[1-(4-carbamimidoylphenylamino)-2-(propane-1-sulfonylamino)-ethyl]-4,5-diethoxyphenylsulfamoyl} acetic acid (52 mg). $[\alpha]_{Na}$-42.1 (c 1.01, methanol) MS (M+H)=587.

Example 10

6-alkoxysubstituted sulfonamides

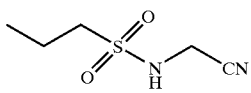

Aminoacetonitrile (14.25 g, 92.5 mmoles) was dissolved in 1,2-dichloroethane (150 ml) and the reaction was placed under $N_2$. Triethylamine (32.76 g, 324 mmoles) was added and the reaction was cooled to zero degrees Celsius. A solution of propane-1-sulfonyl chloride (13.19 g, 92.5 mmoles) in 1,2-dichloroethane (20 ml) was added dropwise and the reaction was allowed to warm to room temperature and was stirred for 16 hours. Thin-layer chromatography showed the presence of a new product with a higher $R_f$. The solvent was removed in vacuo and the crude product was submitted to flash chromatography (methylene chloride-:ethyl acetate, 9:1) to yield 10.56 g of propane-1-sulfonic acid cyanomethyl-amide. $^1$HNMR (CDCl$_3$): 5.40 (s, 1H), 4.11 (s, 2H), 3.15,(m, 2H), 1.89 (q, 2H), 1.10 (t, 3H).

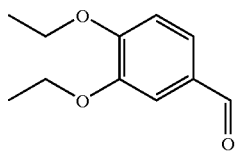

3-Ethoxy-4-hydroxy-benzaldehyde (Aldrich, 100 g, 0.602 mole) was dissolved in N,N-dimethylformamide (1 L). The reaction was placed under $N_2$. Solid potassium carbonate (103 g, 0.662 moles) was added and the reaction was stirred 10 minutes. Iodoethane (175 g, 1.26 moles) was added and the reaction was stirred for 16 hours at room temperature. The reaction was monitored by thin-layer chromatography which indicated complete consumption of the phenol to give a new product. The reaction was filtered to remove the potassium carbonate and solvent removed in vacuo. The residue was dissolved in methylene chloride and filtered. Silica gel (200 g) was added and the dichloromethane removed in vacuo. The crude product absorbed on silica gel was submitted to flash chromatography (hexane, 100%, 2L, then ethyl acetate:hexane, 1:3, 2L, then ethyl acetate:hexane, 1:1) to yield 109.36 g of 3,4-diethoxy-benzaldehyde HNMR (CDCl$_3$): 9.83 (s, 1H), 7.41 (m, 2H), 6.96 (d, 1H), 4.17 (m, 4H), 1.50 (t, 3H) 1.47 (t, 3H).

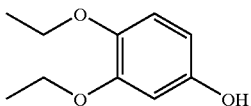

3,4-Diethoxy-benzaldehyde (31.45 g, 0.162 moles) was dissolved in methylene chloride (500 ml). 3-Chloroperbenzoic acid was added and the reaction was heated to reflux for 4 hours. Thin-layer chromatography showed consumption of the aldehyde. The reaction was cooled to room temperature, diluted with methylene chloride and quenched with saturated aqueous potassium carbonate. The layers were separated and the aqueous solution extracted with methylene chloride. The methylene chloride extracts were combined, washed with water, brine, and dried over anhydrous sodium sulfate, filtered and the solvent was removed in vacuo to yield a crude oil.

The crude oil was dissolved in methanol (300 ml) and a solution of 10% aqueous KOH (60 ml) was added. The reaction was stirred at room temperature for 16 hours. Thin-layer chromatography showed consumption of the intermediate which had formed. The methanol was removed in vacuo and the aqueous solution was acidified with 1.2 N HCl. The solution was extracted with ethyl acetate. The ethyl acetate extracts were washed with water and brine, dried over anhydrous sodium sulfate, filtered, and the solvent removed in vacuo. The residue was submitted to flash chromatography (hexane:ethyl acetate, 3:1) to yield 22.08 g of 3,4-diethoxy-phenol. $^1$HNMR (CDCl$_3$): 6.56 (d, 1H), 6.25 (d, 1H), 6.10 (dd, 1H), 3.82 (m, 4H), 1.22 (t, 3H), 1.20 (t, 3H).

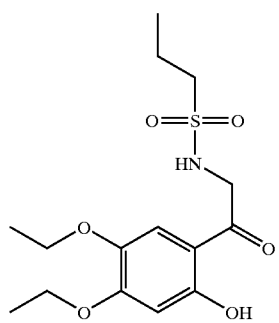

Nitrobenzene (100 ml) was cooled to zero degrees Celsius and saturated with HCl gas. To this solution was added of 3,4-diethoxy-phenol (11.64 g, 64 mmoles), propane-1-sulfonic acid cyanomethyl-amide (10.36 g, 64 mmoles) and zinc chloride (17.45 g, 128 mmoles). The reaction was stirred for 1 hour at zero degrees Celsius and then allowed to warm to room temperature. Stirring was continued for 2 hours. Thin-layer chromatography showed consumption of 3,4-diethoxy-phenol. Water (100 ml) was added cautiously and the reaction was heated to 100 degrees Celsius for 1 hour. The reaction was cooled, and extracted with methylene chloride. The extracts were washed with water, brine, dried over anhydrous sodium sulfate, filtered, and the solvent was removed in vacuo. The residue was submitted to flash chromatography (2.5–5% ethyl acetate in methylene chloride). The purified product was triturated with ether, filtered and air dried to yield 17.3 g of propane-1-sulfonic acid [2-(4,5-diethoxy-2-hydroxy-phenyl)-2-oxo-ethyl]-amide. $^1$HNMR (CDCl$_3$): 11.86 (s, 1H), 6.93 (s, 1H), 6.46 (s, 1H), 5.26 (t, 1H), 4.55 (d, 2H), 4.14 (q, 2H), 4.03 (q, 2H), 3.05 (m, 2H), 1.90 (m, 2H), 1.45 (m, 6H), 1.07 (t, 3H).

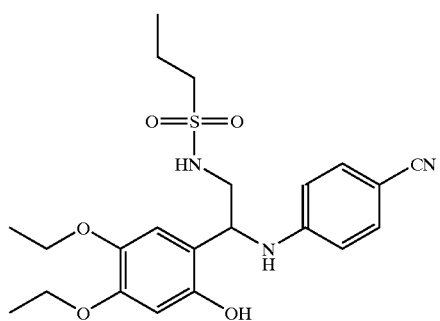

Propane-1-sulfonic acid [2-(4,5-diethoxy-2-hydroxy-phenyl)-2-oxo-ethyl]-amide (200 mg, 0.579 mmoles) was dissolved in tetrahydrofuran (5 ml), placed under $N_2$, and cooled to zero degrees Celsius. Borane:THF complex (1.74 ml, 1.0 M in THF, 1.74 mmoles) was added dropwise. The reaction was stirred 15 minutes and the allowed to warm to room temperature over 2 hours. Thin-layer chromatography showed consumption of starting material and formation of a new product with a lower $R_f$. The reaction was quenched in 1.2 N aqueous HCl (2.5 ml), diluted with water and extracted with ethyl acetate. The extracts were washed with water and brine, dried over anhydrous sodium sulfate, filtered, and the solvent removed in vacuo to yield 190 mg of a crude oil.

The crude oil was dissolved in acetonitrile (5 ml). 4-Aminobenzonitrile (194 mg, 1.64 mmoles) and lithium perchlorate (233 mg, 2.19 mmoles) were added. The reaction was heated to 90 degrees Celsius for 3.5 hours then stirred at room temperature for 18 hours. Thin-layer chromatography showed the presence of a new product with a higher $R_f$ versus the product from the reduction. The reaction was quenched in water and extracted with ethyl acetate. The ethyl acetate extracts were washed with water and brine, dried over anhydrous sodium sulfate, filtered, and the solvent removed in vacuo. The residue was submitted to flash chromatography (ethyl acetate:methylene chloride, 1:9) to yield 134 mg of propane-1-sulfonic acid [2-(4-cyano-phenylamino)-2-(4,5-diethoxy-2-hydroxy-phenyl)-ethyl]-amide. $^1$HNMR (CDCl$_3$): 7.34 (d, 2H), 6.71 (s, 1H), 6.61 (d, 2H), 6.41 (s, 1H), 5.58 (d, 1H), 4.79 (m, 1H), 4.57 (m, 1H), 3.99 (m, 4H), 3.48 (t, 2H), 3.00 (m, 2H), 1.80 (q, 2H), 1.41 (t, 3H), 1.34 (t, 3H), 1.03 (t, 3H).

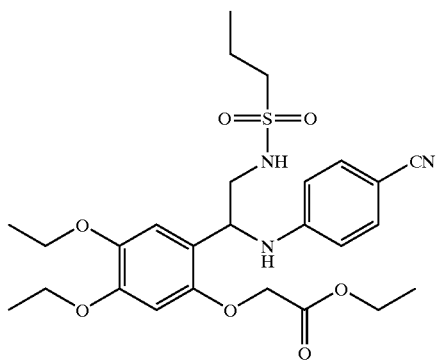

Propane-1-sulfonic acid [2-(4-cyano-phenylamino)-2-(4,5-diethoxy-2-hydroxy-phenyl)-ethyl]-amide (100 mg, 0.223 mmoles) was dissolved in dimethylformamide (1.5 ml) and treated with solid potassium bicarbonate (22 mg, 0.223 mmoles) followed by ethyl bromoacetate (0.37 ml, 0.223 mmoles). The reaction was stirred under N$_2$, for 67 hours. Thin-layer chromatography showed presence of a new product with a higher $R_f$. The reaction was quenched in water and extracted with ethyl acetate. The ethyl acetate extracts were washed with water and brine, dried over anhydrous sodium sulfate, filtered and the solvent removed in vacuo. The residue was submitted to flash chromatography (ethyl acetate:methylene chloride 1:9) to yield 78 mg of {2-[1-(4-cyano-phenylamino)-2-(propane-1-sulfonylamino)-ethyl]-4,5-diethoxy-phenoxy}-acetic acid ethyl ester. $^1$HNMR (CHCl$_3$): 7.35 (d, 2H), 6.81 (s, 1H), 6.57 (d, 2H), 6.43 (s, 1H), 4.81 (t, 1H), 4.68 (ABq, 2H), 4.56 (t, 1H), 4.26 (q, 2H), 4.05 (q, 2H), 3.95 (m, 2H), 3.54 (t, 2H), 2.98 (m, 2H) 1.80 (m, 2H) 1.42 (t, 3H), 1.32 (t, 6H), 1.02 (t, 3H). MS (M+H): 534.

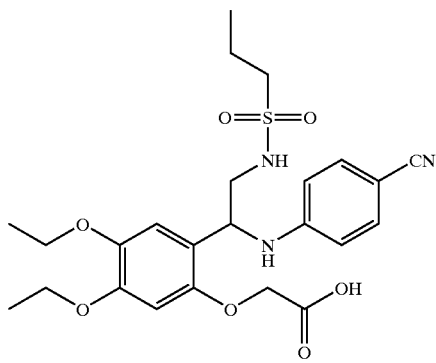

{2-[1-(cyano-phenylamino)-2-(propane-1-sulfonylamino)-ethyl]-4,5-diethoxy-phenoxy}-acetic acid ethyl ester (76 mg, 0.142 mmoles) was dissolved in tetrahydrofuran (3 ml). Water (1 ml) was added and the reaction was cooled to zero degrees Celsius. Aqueous LiOH (1.0 M, 0.42 ml, 0.42 mmol) was added to the reaction. After stirring for 5 minutes, the reaction was allowed to warm to room temperature and was stirred for 16 hours at room temperature The disappearance of the ester was monitored by analytical high pressure liquid chromatography. Additional LiOH (1.0 M. 0.14 ml) was added. The reaction was stirred another 8 hours at room temperature. Consumption of the ester was not complete so freshly prepared LiOH (1.0 M, 0.14 ml), was added and the reaction stirred 24 hours. More LiOH (1.0 M, 0.28 ml) was added and after 67 hours, analytical RP HPLC showed consumption of the ester (total 1.0 M LiOH=0.98 mL, 6.9 equiv.). The reaction was acidified with acetic acid and the THF was allowed to evaporate under a stream of N$_2$. The solution was clarified by addition of acetonitrile and then purified by preparative reverse-phase HPLC (gradient acetonitrile/water with 0.1% trifluoroacetic acid) to yield after lyophilization 44 mg of the mono-TFA salt of {2-[1-(cyano-phenylamino)-2-(propane-1-sulfonylamino)-ethyl]-4,5-diethoxy-phenoxy}-acetic acid. $^1$NMR (CD$_3$OD): 7.15 (d, 2H), 6.70 (s, 1H), 6.48 (d, 2H), 6.45 (s, 1H), 4.76 (t, 1H), 4.60 (s, 2H), 3.85 (q, 2H), 3.73 (m, 2H), 3.43 (dd, 1H), 3.26 (dd, 1H partially obscured by the CH3OH solvent peak), 2.76 (m, 2H), 1.52 (m, 2H), 1.18 (t, 3H), 1.07 (t, 3H), 0.77 (t, 3H). MS (M+H): 506.

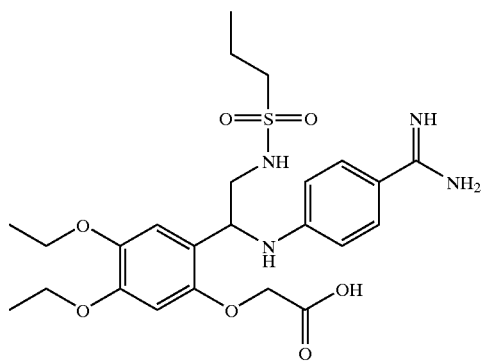

{2-[1-(cyano-phenylamino)-2-(propane-1-sulfonylamino)-ethyl]-4,5-diethoxy-phenoxy}-acetic acid, mono-TFA salt form (44 mg, 0.071 mmoles) was dissolved in ethanol (1 ml) and treated with diisopropylethylamine (0.89 ml, 0.515 mmoles) and solid hydroxylamine hydrochloride (25 mg, 0.355 mmoles). The reaction was placed under N₂ and heated to 60 degrees Celsius for 3 hours. Analytical high pressure liquid chromatography analysis after 3 hours revealed the reaction had not gone to completion. The reaction mixture was cooled to room temperature and stirred at room temperature for 16 hours and the progress of the conversion assessed by HPLC. The reaction mixture was heated at 60 degrees Celsius for 8 hours, stirred at room temperature for 16 hours, heated at 70 degrees for 8 hours and stirred at room temperature for 16 hours. HPLC showed consumption of starting material. The reaction was acidified with acetic acid, Raney nickel added and the reaction was hydrogenated at approximately 1 atm under a balloon of hydrogen for 3 hours. Analytical HPLC showed consumption of the hydroxy amidine intermediate. The Raney nickel catalyst was filtered and the solvent was removed in vacuo. The residue purified by preparative reverse-phase HPLC (gradient acetonitrile/water with 0.1% trifluoroacetic acid) to yield after lyophilization 5.6 mg of {2-[1-(carbamimidoyl-phenylamino)-2-(propane-1-sulfonylamino)-ethyl]-4,5-diethoxy-phenoxy}-acetic acid, bis-TFA salt form. MS (M+H): 523.

Example 11

6-alkylsulfonyl-alkyl-amino Substituted Acylsulfonamide Synthesis

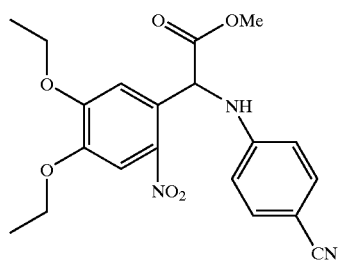

4,5 diethoxy-2-nitrobenzaldehyde (55.5 g 206 mmoles) and 4-aminobenzonitrile (23 g, 195 mmoles) were dissolved in methanol (700 ml) and stirred at 60° C. for 2 hours. The reaction was allowed to cool to 0° C. and tosylmethylisonitrile (45 g. 230 mmoles) added. Boron trifluoroetherate (78 ml, 620 mmoles) was added dropwise over 10 minutes. The reaction was stirred at 0° C. for 30 minutes, allowed to come to room temperature and then stirred at ambient temperature for 1.5 hours. Water (18 ml) was added and the mixture stirred at room temperature overnight. The following day the methanol was removed in vacuo and the residue taken up in ethyl acetate. The organic layer was washed with water and then dried over anhydrous sodium sulfate. The sodium sulfate was filtered off and the ethyl acetate removed in vacuo. The crude material was submitted to flash chromatography (hexanes: ethyl acetate, 2:1 then 1:1) to yield 46 g of the desired product (4-ethoxy-5-ethoxy-2-nitro-phenyl)-(4-cyano-phenylamino)-acetic acid methyl ester.

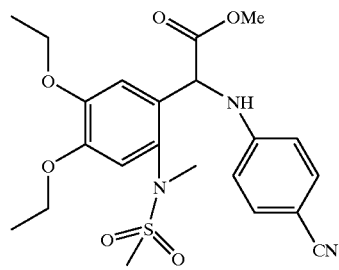

(4-ethoxy-5-ethoxy-2-nitro-phenyl)-(4-cyano-phenylamino)-acetic acid methyl ester (11 g, 27.5 mmole) was dissolved in ethyl acetate (300 m) and added to a flask containing 5% Pt/C (3 g) under a nitrogen atmosphere. The nitrogen was removed and replaced by hydrogen (balloon) and the reaction stirred vigorously for 6 hours. The catalyst was filtered off and the solvent removed in vacuo. The residue was taken up in dichloromethane (ca. 300 ml) and pyridine (5.6 ml, 70 mmole) added. The reaction was cooled to 0° C. and methanesulfonyl chloride (2.5 ml, 33 mmole) added dropwise. The reaction was stirred overnight. The solution was washed with water and the solvent removed in vacuo. The crude product was chromatographied on silica using flash chromatography (Hexane:ethyl acetate 1:1) to yield 5 g of desired material-(4-cyano-phenylamino)-[4,5-diethoxy-2-(methanesulfonylamino)-phenyl]-acetic acid methyl ester. The product from about (4-cyano-phenylamino)-4,5-diethoxy-2-methanesulfonylamino-phenyl)-acetic acid methyl ester (5 g, 10.7 mmoles) was dissolved in dry DMF (100 ml) and cesium carbonate (7.25 g, 22 mmoles) and iodomethane (1 ml, 16 mmoles) added. The reaction was stirred at room temperature for 3 hours and the solvent removed in vacuo. The residue was taken up in ethyl acetate, acidified with 1N hydrochloric acid and the organic layer washed once with water. The material was dried over anhydrous sodium sulfate and the solvent removed in vacuo. The residue was flash chromatographed (hexane:ethyl acetate, 1:1) to yield 2.6 g of desired material—(4-cyano-phenylamino)-[4,5-diethoxy-2-(methanesulfonyl-methyl-amino)-phenyl]-acetic acid methyl ester.

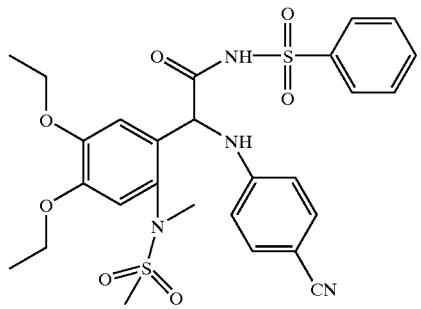

The (4-cyano-phenylamino)-4,5-diethoxy-2-methanesulfonyl-methyl-amino-phenyl)-acetic acid methyl ester obtained above (2.6 g, 5 mmole) was dissolved in methanol. 1 N LiOH was added (25 ml) and the reaction stirred at room temperature for 5 hours. The methanol was removed in vacuo and the reaction was acidified with 1 N hydrochloric acid. The product was extracted into ethyl acetate and washed with water. Flash chromatography (Ethyl acetate with 5% acetic acid) yielded 1.9 g the desired acid—(4-cyano-phenylamino)-[4,5-diethoxy-2-(methanesulfonyl-methyl-amino)-phenyl]-acetic acid.

The (4-cyano-phenylamino)-4,5-diethoxy-2-methanesulfonyl-methyl-amino-phenyl)-acetic acid obtained above (350 mg, 0.75 mmole) was combined with carbonyl diimidazole (610 mg, 3.77 mmole) in dry THF (6 ml). The reaction was heated at 60° C. for 1 hour and cooled to room temperature. To this solution was added phenylsulfonamide (650 mg, 4.14 mmole) and DBU (5 mmole) as a solution in 5 ml THF. The reaction was stirred for 3 hours and the THF removed in vacuo. The residue was taken up in ethyl acetate and acidified with 1 N hydrochloric acid. The organic layer was separated, washed with water and dried over anhydrous sodium sulfate. The crude product was purified by flash chromatography (Hexanes:ethyl acetate 1:1 then ethyl acetate with 5% acetic acid) to yield 302 mg of desired product -N-{(4-cyano-phenylamino)-[4,5-diethoxy-2-(methanesulfonyl-methyl-amino)-phenyl]-acetyl}benzenesulfonamide.

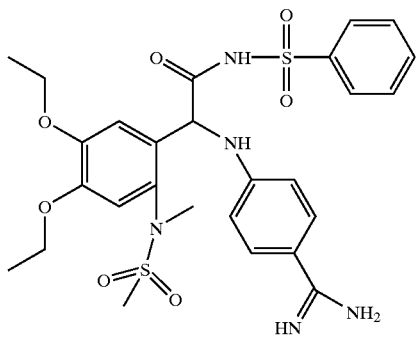

The N-{(4-cyano-phenylamino)-[4,5-diethoxy-2-(methanesulfonyl-methyl-amino)-phenyl]-acetyl}benzenesulfonamide obtained above (126 mg, 0.21 mmole) was dissolved in ethanol (1.8 ml) and heated to 60° C. Diisopropylethylamine (DIPEA—260 ul, 1.5 mmole) was added followed by hydroxylamine-hydrochloride (74 mg, 1.04 mmole). The reaction was stirred at 60° C. under a nitrogen atmosphere for 6 hours. The reaction was then allowed to cool to room temperature. The solution was diluted with methanol (5 ml) and acetic acid (2 ml) and Raney Nickel 2800 (ca. 50 mg) added as a suspension- The reaction was then stirred vigorously under a hydrogen atmosphere for 1 hour. The catalyst was filtered off and the solvent removed. The crude product was purified by preparative reverse-phase HPLC using a water-acetonitrile (0.1% TFA) gradient to yield 40 mg of desired 4-{2-benzenesulfonylamino-1-[4,5-diethoxy-2-(methanesulfonyl-methyl-amino)-phenyl]-2-oxo-ethylamino}benzamidine as its trifluoroacetic acid salt. MS: (M+H)=604.

Example 12

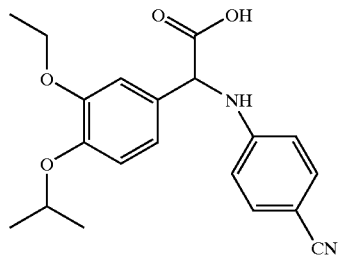

4-isopropoxy-5-ethoxy-benzaldehyde (10.6 g 50 mmoles) and 4-aminobenzonitrile (5.9 g, 50 mmoles) were dissolved in methanol (150 ml) and stirred at 60° C. for 1.6 hours. The reaction was allowed to cool to 0° C. and tosylmethylisonitrile (9.75 g. 50 mmoles) added. Boron trifluoroetherate (19 ml, 150 mmoles) was added dropwise over 10 minutes. The reaction was stirred at 0° C. for 30 minutes, allowed to come to room temperature and then stirred at ambient temperature for 1.5 hours. Water (4.5 ml) was added and the mixture stirred at room temperature 2 days. The methanol was removed in vacuo and the residue taken up in ethyl acetate. The organic layer was washed with water and then dried over anhydrous sodium sulfate. The sodium sulfate was filtered off and the ethyl acetate removed in vacuo. The crude material was submitted to flash chromatography (hexanes:ethyl acetate, 1:1) to yield 12.5 g of the desired product (4-isopropoxy-5-ethoxy-phenyl)-(4-cyano-phenylamino)-acetic acid methyl ester.

The product from above, (4-isopropoxy-5-ethoxy-phenyl)-(4-cyano-phenylamino)-acetic acid methyl ester, (6 g, 16.3 mmole) was treated with 1 N LiOH (ca. 50 ml) in THF (ca. 150 ml). The reaction was stirred at room temperature for 6 hours and acidified with 1 N hydrochloric acid. The THF was removed in vacuo and the product extracted into ethyl acetate. The crude material was purified by reverse phase chromatography (ethyl acetate 3% acetic acid) to yield 4.85 g of desired acid—(4-isopropoxy-5-ethoxy-phenyl)-(4-cyano-phenylamino)-acetic acid.

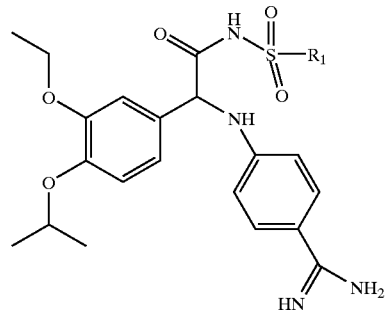

The (4-isopropoxy-5-ethoxy-phenyl)-(4-cyano-phenylamino)-acetic acid obtained above (200 mg, 0.57 mmole) was combined with carbonyl diimidazole (200 mg, 1.2 mmole) in dry THF (4 ml). The reaction was allowed to stir at room temperature for 1 hour. To this solution was added the corresponding alkyl or arylsulfonamide (2.2 mmole) and DBU (2.2 mmole) as a solution in 3 ml THF. The reaction was stirred overnight and the THF removed in vacuo. The residue was taken up in ethyl acetate and acidified with acetic acid. The organic layer was separated, washed with water and dried over anhydrous sodium sulfate. The crude product was purified by flash chromatography (Hexanes:ethyl acetate 1:2) to yield desired product—N-{(4-cyano-phenylamino)-[∝isopropoxyl,5-ethoxy-phenyl]-acetyl}(alkyl or aryl) sulfonamide.

The N-{(4-cyano-phenylamino)-[4 isopropoxyl-5-ethoxy-phenyl]-acetyl}(alkyl or aryl) sulfonamide obtained above (ca. 0.24 mmole) was dissolved in ethanol (1–3 ml) and heated to 60° C. Diisopropylethylamine (DIPEA—260 ul, 1.5 mmole, 6 eq.) was added followed by hydroxylamine-hydrochloride (84 mg, 1.25 mmole, 5 eq.). The reaction was stirred at 60° C. under a nitrogen atmosphere for ca. 6 hours. The reaction was then allowed to cool to room temperature. The solution was diluted with methanol (5 ml) and acetic acid (2 ml) and Raney Nickel 2800 (ca. 50 mg) added as a suspension. The reaction was then stirred vigorously under a hydrogen atmosphere for 1–6 hours. The catalyst was filtered off and the solvent removed. The crude products were purified by preparative reverse-phase HPLC using a water-acetonitrile (0.1% TFA) gradient or by flash chromatography (ethyl acetate:acetone:water:acetic acid, 6:2:1:1) to yield the desired 4-{2-(alkyl or aryl) sulfonylamino-1-[4-isopropoxy,5-ethoxy)-phenyl]-2-oxo-ethylamino}benzamidine as its trifluoroacetic acid or acetic acid salt.

Using an analogous procedure, the following compounds having different $R_1$ groups were prepared:

$R_1$=ethyl: 4-{2-ethylsulfonylamino-1-[4-isopropoxy,5-ethoxy)-phenyl]-2-oxo-ethylamino}benzamidine: MS(M+H)=463.

$R_1$=n-propyl: 4-{2-propylsulfonylamino-1-[4-isopropoxy,5-ethoxy)-phenyl]-2-oxo-ethylamino}benzamidine: MS(M+H)=477.

$R_1$=n-butyl: 4-{2-butylsulfonylamino-1-[4-isopropoxy,5-ethoxy)-phenyl]-2-oxo-ethylamino}benzamidine: MS(M+H)=491.

$R_1 = CH_2CH_2CO_2Me$: 3-[(4-carbamimidoyl-phenylamino)-(3-ethoxy-4-isopropoxy-phenyl)-acetylsufamoyl]-propionic acid methyl ester: MS(M+H)=521.

$R_1$=phenyl: 4-{2-benzenesulfonylamino-1-[4-isopropoxy,5-ethoxy)-phenyl]-2-oxo-ethylamino}benzamidine: MS(M+H)=511.

Example 13

Acylsulfonamide with Substitution on the Aminobenzamidine Ring

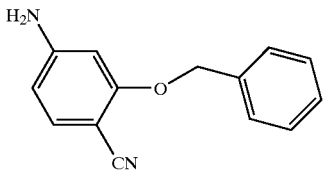

2-Hydroxy-4-nitro-benzonitrile (11.2 g, 68 mmole) was dissolved in DMF (200 ml). Potassium carbonate (11 g. 80 mmole) and benzyl bromide (9 ml, 75 mmole) were added. The reaction was stirred at room temperature overnight. The DMF was removed in vacuo and the residue taken up in ethyl acetate and water. The organic layer was separated, washed with 1 N NaOH, then with water, and dried over sodium sulfate. The crude product (5 g) was dissolved in ethyl acetate (75 ml) and added to a flask containing 5% Pt/C (500 mg). The reaction was placed under a hydrogen atmosphere (balloon) and stirred vigorously for several hours until the reaction was done (TLC). The catalyst was filtered off and the solvent removed. The product was purified by flash chromatography to yield 4.12 g of 4-amino, 2-benzyloxybenzonitrile.

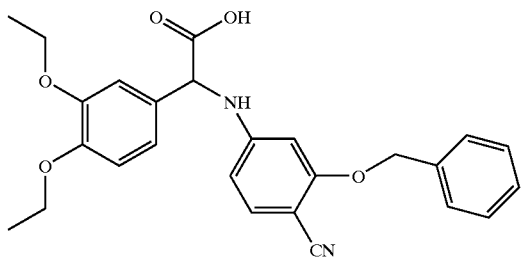

4,5-diethoxy-benzaldehyde (3.6 g, 17.8 mmole) and 4-amino-2-benzyloxybenzonitrile (3.7 g, 17.8 mmole) were dissolved in methanol (40 ml) and stirred for 2 hours. Tosylmethylisonitrile (3.48 g. 17.8 mmoles) was added. The reaction was cooled to 0° C. and boron trifluoroetherate (6,7 ml, 54 mmoles) was added dropwise. The reaction was stirred at 0° C. for 30 minutes, allowed to come to room temperature and then stirred at ambient temperature for 3.5 hours. Water (1,6 ml) was added and the mixture stirred at room temperature 2 days. The methanol was removed in vacuo and the residue taken up in ethyl acetate. The organic layer was washed with water and then dried over anhydrous sodium sulfate. The sodium sulfate was filtered off and the ethyl acetate removed in vacuo. The crude material was submitted to flash chromatography (hexanes:ethyl acetate, 4:1) to yield 4.2 g of the desired product (3-benzyloxy-4-cyano-phenylamino)-3,4-ethoxy-phenyl-)-acetic acid methyl ester.

The product from above was treated with LiOH (1.96 g) in water (50 ml) methanol (100 m), and THF (50 ml). The reaction was stirred at room temperature for 3 hours and acidified with acetic acid. The solvent was removed in vacuo and the product extracted into ethyl acetate. The crude material was purified by reverse phase chromatography (ethyl acetate 3% acetic acid) to yield 5 g of desired acid—product (3-benzyloxy-4-cyano-phenylamino)-3,4-ethoxy-phenyl-)-acetic acid.

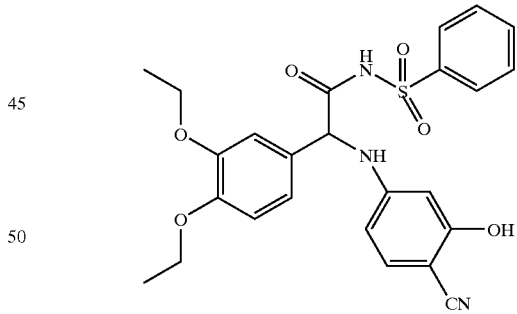

(3benzyloxy-4-cyano-phenylamino)-3,4-ethoxy-phenyl-)-acetic acid (750 mg, 1.68 mmoles) was dissolved in dry THF (3 ml) and carbonyl diimidizole (CDI—545 mg, 3.36 mmoles) was added. The reaction was heated to 40 degrees for 1 hour then cooled to room temperature. To this was added a solution of benzenesulfonamide (1.05 g, 6.7 mmoles), DBU (1.02 g 6.72 mmoles) in THF (3 ml). The reaction was stirred overnight and then 1 N hydrochloric acid was added. The THF was removed in vacuo and the product purified by flash chromatography (ethyl acetate 2% acetic acid) to yield the desired product. This material (215 mg) was dissolved in ethanol (5 ml) containing acetic acid (1 drop) and added to 5% Pd/C (100 mg). The reaction was placed under a hydrogen atmosphere and stirred vigorously until the reaction was complete. The catalyst was filtered off and than solvent removed in vacuo. The crude product was purified by flash chromatography to yield 150 mg of desired product—N-[(3-hydroxy-4-cyano-phenylamino)-(3,4-diethoxy-phenyl-acetyl]benzenesulfonamide.

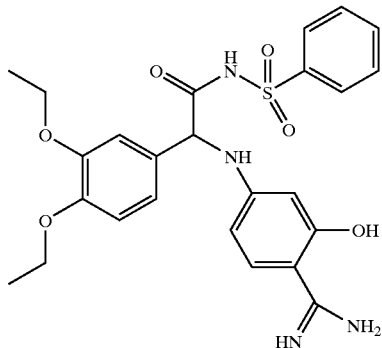

The N-[(3-hydroxy-4-cyano-phenylamino)-(3,4-diethoxy-phenyl-acetyl]benzenesulfonamide obtained above (75 mg, 0.15 mmoles) was dissolved in ethanol (2 ml) and heated to 60° C. Diisopropylethylamine (DIPEA—185 ul, 1 mmole) was added followed by hydroxylamine-hydrochloride (53 mg, 0.75 mmole). The reaction was stirred at 60° C. under a nitrogen atmosphere for ca. 6 hours. The reaction was then allowed to cool to room temperature overnight. The solution was diluted with acetic acid (1 ml) and methanol (1 ml). Raney Nickel 2800 (ca. 50 mg) was added as a suspension. The reaction was then stirred vigorously under a hydrogen atmosphere for 0.5 hours. The catalyst was filtered off and the solvent removed. The crude products were purified by preparative reverse-phase HPLC using a water-acetonitrile (0.1% TFA) gradient to yield the desired amidine product—4-[2-benzenesulfonylamino-1-(3,4 diethoxy-phenyl)-2-oxo-ethylamino]-2-hydroxybenzamidine. MS (M+H)=513.

Using an analogous procedure, the corresponding halogen containing compounds can be made from 2-chloro-4-nitro-benzonitrile and 2-bromo-4-nitro-benzonitrile.

Example 14

Tissue Factor/Factor VIIa Antagonist Assay

This procedure can be used to determine the constant of inhibition (Ki) for a sample compound of the invention.

| Materials: | |
|---|---|
| Assay Buffer: | 100 mM Hepes pH 7.8, 140 mM NaCl, 0.1% PEG-8000, 0.02% Tween-80, 5 mM CaCl$_2$ |
| Coagulation Factor: | recombinant human factor VIIa (NB #25942-16) |
| Cofactor: | soluble Tissue Factor (1-219) |
| Substrate: | Chromozym-tPA (Boehringer Mannheim, Cat. #1093 037) Reconstitute at 20 mM in H$_2$O. Dilute to 4 mM in assay buffer with CaCl$_2$ prior to use. |
| Samples: | Dilute samples to 3% DMSO in assay buffer (lacking CaCl$_2$). |

| Procedure: |
|---|
| 1. Prepare a solution of 2 μg/mL (90 nM) tissue factor and 1.5 μg/mL (30 nM) factor VIIa in assay buffer with CaCl$_2$. |
| 2. Incubate for 15 minutes at room temperature. |
| 3. Add 50 μL sample to each well. |
| 4. Add 50 μL tissue factor/factor VIIa solution to each well. |
| 5. Incubate for 15 minutes at room temperature with gentle agitation. |
| 6. Add 50 μL substrate to each well. |
| 7. Agitate plate for 20–25 sec. |
| 8. Monitor absorbance at 405 nM every 10 sec for a total of 5 minutes at room temperature. |
| 9. Calculate Vmax over 10 points. |

Example 15

Factor Xa, Thrombin, and Plasma Kallikrein Assays

These procedures can be used to determine the constant of inhibition (Ki) for a sample compound of the invention.

| Materials: | |
|---|---|
| Assay Buffer: | 100 mM Hepes pH 7.8, 140 mM NaCl, 01% PEG-8000, 0.02% Tween-80 |
| Coagulation | human Factor Xa, Thrombin, or Plasma Kallikrein (Hematologic Technologies) |
| Factor: | Dilute to 0.45μg/mL (9.8 nM) in assay buffer. |
| Substrate: | S-2222, S2366 or S2302 -(See below - Chromogenix Inc,) Reconstitute at 5 mM in H2O. Dilute to 1.5 mM in assay buffer prior to use. |
| Samples: | Dilute samples to 3% DMSO in assay buffer. |

| Procedure: |
|---|
| 1. Add 50 μL sample to each well. |
| 2. Add 50 μL appropriately diluted coagulation factor to each well. |
| 3. Incubate for 5 minutes at room temperature with gentle agitation. |
| 4. Add 50 μL appropriately diluted substrate to each well. |
| 5. Agitate plate for 20–25 sec. |
| 6. Monitor absorbance at 405 nM every 10 sec for a total of 5 minutes at room temperature. |
| 7. Calculate Vmax over 10 points. |

| Assay - Enzyme, Substrate and Final Concentrations | | | | |
|---|---|---|---|---|
| Assay | TF/FVIIa | FXa | Thrombin | PlasmaKallikrein |
| Coag Factor Final concentration | 10 nM FVIIa 30 nM TF | 3.3 nM | 8.2 nM | 1.5 nM |
| Substrate | Chromo-zyme tPA | S-2222 | S-2366 | S-2302 |
| Final Conc. of Substrate | 1.33 mM | 0.5 mM | 0.3 mM | 0.3 mM |

What is claimed is:

1. A compound having the structure:

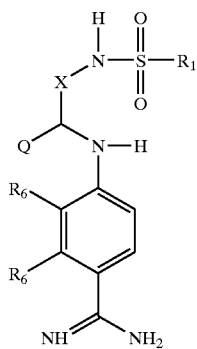

wherein

X is C=O or CH$_2$;

R$_1$ is selected from C$_1$–C$_6$ alkyl, C$_2$–C$_6$ alkenyl, C$_2$–C$_6$ alkynyl, C$_3$–C$_6$ cycloalkyl, phenyl, naphthyl, benzyl and heteroaryl, wherein heteroaryl has 5 or 6 ring carbon atoms and 1 or 2 heteroatoms, where the heteroatoms are N, S, or O, and where the heteroaryl group is linked to the sulfonamide group by a carbon atom; and where R$_1$ is optionally substituted with 1–3 substituents selected from halo, nitro, C$_1$–C$_6$ alkyl, NR$_7$R$_8$, OR$_7$, SR$_7$, C$_1$–C$_6$ alkyl-C(O)OR$_7$, C$_1$–C$_6$ alkyl-OC(O)R$_7$, C$_1$–C$_6$ alkyl-C(O)R$_7$, C$_1$–C$_6$ alkyl-OR$_7$, C$_1$–C$_6$ haloalkyl, C$_1$–C$_6$ alkyl-NR$_7$R$_8$, C(O)OR$_7$, OC(O)R$_7$, C(O)NR$_7$R$_8$, OC(O)NR$_7$R$_8$, NHC(O)R$_7$, and NHC(O)NR$_7$R$_8$;

Q is phenyl optionally substituted with one or more groups selected from halo, nitro, C$_1$–C$_6$ alkyl, C$_2$–C$_6$ alkenyl, C$_2$–C$_6$ alkynyl, NR$_7$R$_8$, OR$_7$, SR$_7$, C$_1$–C$_6$ alkyl-C(O)OR$_7$, OC$_1$–C$_6$ alkyl-C(O)OR$_7$, C$_1$–C$_6$ alkyl-OR$_7$, OC$_1$–C$_6$ alkyl-OR$_7$, C$_1$–C$_6$ alkyl-NR$_7$R$_8$, OC$_1$–C$_6$ alkyl-NR$_7$R$_8$, C$_1$–C$_6$ alkyl-C(O)NR$_7$R$_8$, OC$_1$–C$_6$ alkyl-C(O)NR$_7$R$_8$, C$_1$–C$_6$ alkyl-C(O)R$_7$, OC$_1$–C$_6$ alkyl-C(O)R$_7$, C$_1$–C$_6$ haloalkyl, O-aralkyl, C(O)OR$_7$, C(O)NR$_7$R$_8$, OC(O)NR$_7$R$_8$, NHC(O)R$_7$, NHC(O)NR$_7$R$_8$, NR$_7$S(O)$_2$R$_1$, NR$_7$S(O)$_2$R$_7$, NR$_7$S(O)$_2$ C$_1$–C$_6$ alkyl-C(O)OR$_7$, S(O)$_2$R$_7$, and S(O)$_2$NR$_7$R$_8$;

R$_6$ is selected from H, C$_1$–C$_6$ alkyl, C$_1$–C$_6$ alkyl-OR$_7$, C$_1$–C$_6$ alkyl-NR$_7$R$_8$, C$_1$–C$_6$ haloalkyl, halo, cyano, OR$_7$, SR$_7$, NR$_7$R$_8$, C(O)OR$_7$, C(O)R$_7$ and OC(O)R$_7$; and R$_7$ and R$_8$ are independently H, C$_1$–C$_6$ alkyl, or phenyl; and acid and base addition salts thereof.

2. The compound of claim 1 wherein X is a carbonyl group, C=O.

3. The compound of claim 1 wherein R$_6$ is H.

4. The compound of claim 1 wherein R$_1$ is selected from phenyl, ethyl, thiophenyl, propyl, and methyl.

5. The compound of claim 1, wherein Q has the structure

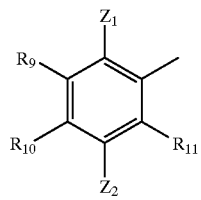

wherein

R$_9$ is C$_1$–C$_6$ alkoxy

R$_{10}$ is C$_1$–C$_6$ alkoxy, or O—C$_1$–C$_6$ alkyl-C$_6$–C$_{10}$ aryl;

R$_{11}$ is H, NR$_7$S(O)$_2$R$_7$, or NR$_7$S(O)$_2$ C$_1$–C$_6$ alkyl-C(O) OR$_7$;

Z$_1$ is H; and

Z$_2$ is H or C$_1$–C$_6$ alkoxy.

6. The compound of claim 5 wherein Z$_2$ is hydrogen; Z$_2$ and R$_{11}$ are hydrogen; or R$_{11}$ is hydrogen.

7. The compound of claim 5 wherein Z$_2$ is C$_1$–C$_6$ alkoxy.

8. The compound of claim 5 wherein R$_9$ and R$_{10}$ are independently selected from OCH$_3$, OEt, OiPr, OiBu, OCH$_2$Ph, and OCH(CH$_2$Cl)Ph.

9. A compound of claim 1 selected from the structures:

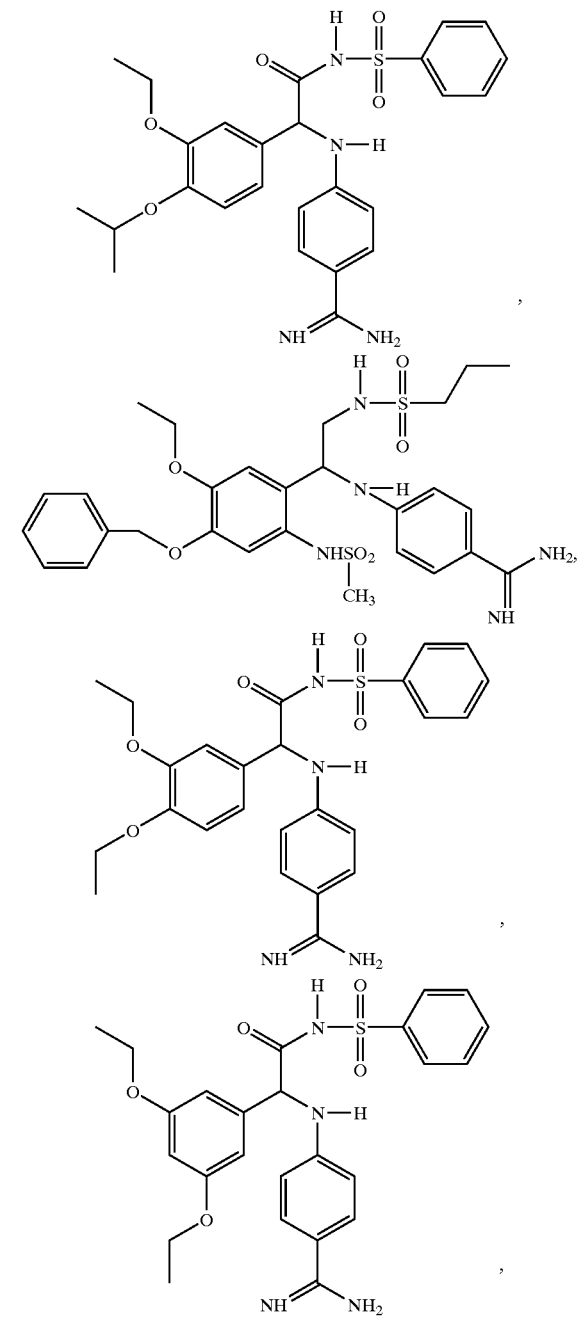

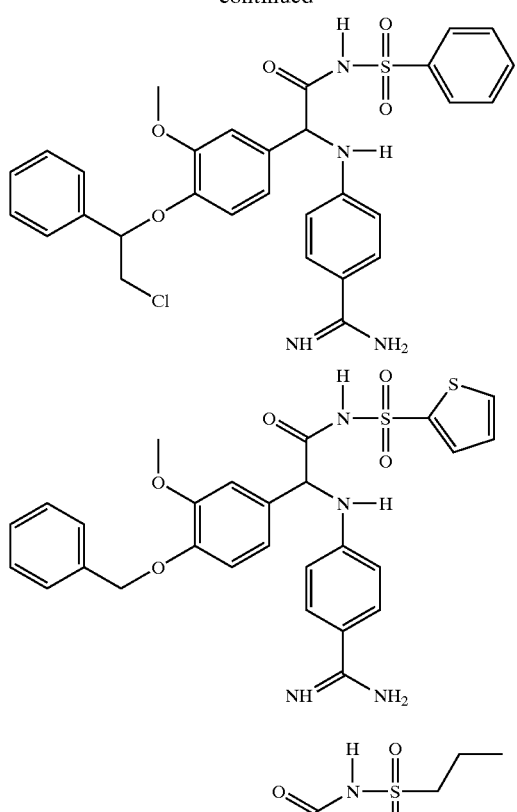

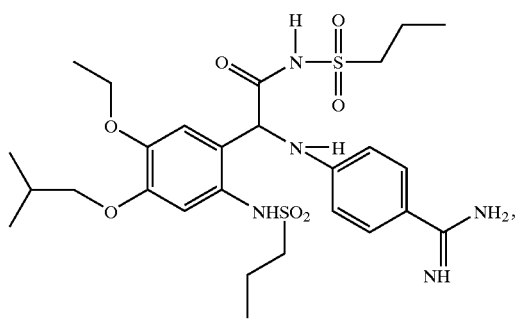

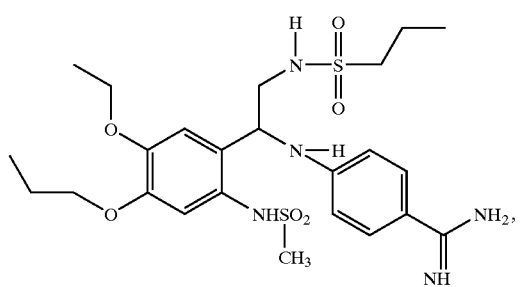

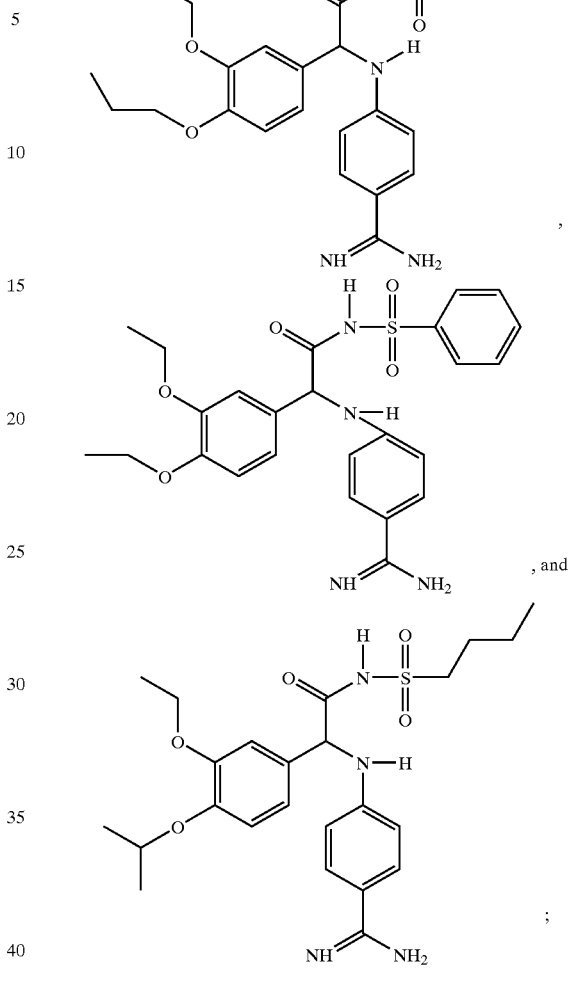

and acid and base addition salts thereof.

10. A compound of claim 1 selected from:

a) 4-[1-(4-Benzyloxy-3-methoxy-phenyl)-2-(benzenesulfonylamino)-ethylamino]-benzamidine: MS (M+H)=531, b) N-{4-[2-(4-Benzyloxy-3-methoxy-phenyl)-2-(4-carbamimidoyl-phenylamino)-ethylsulfamoyl]-phenyl}-acetamide: MS (M+H)=588, c) 4-[1-(4-Benzyloxy-3-methoxy-phenyl)-2-(4-nitro-benzenesulfonylamino)-ethylamino]-benzamidine: MS (M+H)=576, d) 4-[1-(4-Benzyloxy-3-methoxy-phenyl)-2-(4-fluoro-benzenesulfonylamino)-ethylamino]-benzamidine: MS (M+H)=549, e) 4-[1-(4-Benzyloxy-3-methoxy-phenyl)-2-(4-fluoro-benzenesulfonylamino)-ethylamino]-benzamidine: MS (M+H)=565, f) 4-[1-(4-Benzyloxy-3-methoxy-phenyl)-2-(3-nitro-benzenesulfonylamino)-ethylamino]-benzamidine: MS (M+H)=576, g) 4-[1-(4-Benzyloxy-3-methoxy-phenyl)-2-(2,5-dichloro-benzenesulfonylamino)-ethylamino]-benzamidine: MS (M+H)=599, h) 4-[1-(4-Benzyloxy-3-methoxy-phenyl)-2-(2-bromo-benzenesulfonylamino)-ethylamino]-benzamidine: MS (M+H)=609, 611, i) 4-[1-(4-Benzyloxy-3-methoxy-phenyl)-2-(4-bromo-benzenesulfonylamino)-ethylamino]-benzamidine: MS (M+H)=609, j) 4-[1-(4-Benzyloxy-3-methoxy-phenyl)-2-(4-isopropyl-benzenesulfonylamino)-ethylamino]-benzamidine: MS (M±H)=573, k) 4-[1-(4-Benzyloxy-3-methoxy-phenyl)-2-phenylmethanesulfonylamino-ethylamino]-benzamidine: MS (M+H)=545, l) 4-[1-(4-Benzyloxy-3-methoxy-phenyl)-2-(4-carboxy-benzenesulfonylamino)-ethylamino]-benzamidine: MS (M+H)=575, m) 4-[1-(4-Benzyloxy-3-methoxy-phenyl)-2-(3-carboxy-benzenesulfonylamino)-ethylamino]-benzamidine: MS (M+H)=575, n) 4-[1-(4-Benzyloxy-3-methoxy-phenyl)-2-(2,4-dinitro-benzenesulfonylamino)-ethylamino]-benzamidine: MS (M+H)=621, o) 4-[1-(4-Benzyloxy-3-methoxy-phenyl)-2-(2,3,5,-tetramethyl-benzenesulfonylamino)-ethylamino]-benzamidine: MS (M+H)=587, p) 4-[1-(4-Benzyloxy-3-methoxy-phenyl)-2-(3,5-dichloro-2-hydroxy-benzenesulfonylamino)-ethylamino]-benzamidine: MS (M+H)=615, q) 4-[1-(4-Benzyloxy-3-methoxy-phenyl)-2-(3,4-dimethoxy-benzenesulfonylamino)-ethylamino]-benzamidine: MS (M+H)=591, r) 4-[1-(4-Benzyloxy-3-methoxy-phenyl)-2-(thiophene-2-sulfonylamino)-ethylamino]-benzamidine: MS(M+H)=537, s) N-{5- [2-(4-Benzyloxy-3-methoxy-phenyl)-2-(4-carbamimidoyl-phenylamino)-ethylsulfamoyl]-4-methyl-thiazol-2-yl}-acetamide: MS(M+H)=595, t) 4-[1-(4-Benzyloxy-3-methoxy-phenyl)-2-(naphthalene-2-sulfonylamino)-ethylaminol]-benzamidine: MS (M+H)=581, u) 4-[1-(4-Benzyloxy-3-methoxy-phenyl)-2-(naphthalene-1-sulfonylamino)-ethylamino]-benzamidine: MS (M+H)=581, v) 4-[1-(4-Benzyloxy-3-methoxy-phenyl)-2-(2-phenyl-ethenesulfonylamino)-ethylamino]-benzamidine: MS (M+H)=557, w) 4-[1-(4-Benzyloxy-3-methoxy-phenyl)-2-(3-trifluoromethyl-benzenesulfonylamino)-ethylamino]-benzamidine: MS (M+H)=599, x) 4-[1-(4-Benzyloxy-3-methoxy-phenyl)-2-(2,3,4,5,6-pentafluoro-benzenesulfonylamino)-ethylamino]-benzamidine: MS (M+H)=521, y) 4-[1-(4-Benzyloxy-3-methoxy-phenyl)-2-methanesulfonylamino-ethylamino]-benzamidine: MS(M+H)=469, z) 4-[1-(4-Benzyloxy-3-methoxy-phenyl)-2-ethanesulfonylamino-ethylamino]-benzamidine: MS(M+H)=483, aa) 4-[1-(4-Benzyloxy-3-methoxy-phenyl)-2-propanesulfonylamino-ethylamino]-benzamidine: MS(M+H)=497, bb) 4-[1-(4-Benzyloxy-3-methoxy-phenyl)-2-butanesulfonylamino-ethylamino]-benzamidine: MS(M+H)=511, cc) [2-(4-Benzyloxy-3-methoxy-phenyl )-2-(4-carbamimidoyl-phenylamino)-ethylsulfamoyl]-acetic acid ethyl ester MS (M+H) 541, and dd) [2-(4-Benzyloxy-3-methoxy-phenyl)-2-(4-carbamimidoyl-phenylamino)-ethylsulfamoyl]-acetic acid;

and acid and base addition salts thereof.

11. A compound of claim 1 selected from:

a) 4-[2-Benzenesulfonylamino-1-(2-benzenesulfonylamino-4-benzyloxy-5-methoxy-phenyl)-ethylamino]-benzamidine: MS: (M+H)=686, b) 4-[2-Benzenesulfonylamino-1-(2-benzenesulfonylamino-4-benzyloxy-5-ethoxy-phenyl)-ethylamino]-benzamidine: MS: (M+H)=700, c) 4-[1-(4-Benzyloxy-5-ethoxy-2-methanesulfonylamino-phenyl)-2-(propane-1-sulfonylamino)-ethylamino]-benzamidine: MS (M+H)=604, d) 4-[1-(4,5-Diethoxy-2-methanesulfonylamino-phenyl)-2-(propane-1-sulfonylamino)-ethylamino]-benzamidine: MS (M+H)=542, e) {5-Benzyloxy-2-[1-(4-carbamimidoyl-phenylamino)-2-(propane-1-sulfonylamino)-ethyl]-4-methoxy-phenylsulfamoyl}-acetic acid ethyl ester: MS: (M+H)= 676, f) {5-Benzyloxy-2-[1-(4-carbamimidoyl-phenylamino)-2-(propane-1-sulfonylamino)-ethyl]-4-methoxy-phenylsulfamoyl}-acetic acid: MS (M+H)=648, g) 4-[1-(3,4-Dimethoxy-2-methanesulfonylaminophenyl)-2-(propane-1-sulfonylamino)-ethylamino]-benzamidine, 4-[1-(4-Benzyloxy-2-methanesulfonylamino-5-methoxy-phenyl)-2-(propane-1-sulfonylamino)-ethylamino]-benzamidine: MS (M+H)=590, 2-[1-(4-carbamimidoylphenylamino)-2-(propane-1-sulfonylamino)-ethyl]-4,5-diethoxyphenylsulfamoyl-acetic acid: MS (M+H)=587, 2-[1-(4-carbamimidoyl-phenylamino)-2-(propane-1-sulfonylamino)-ethyl]-4,5-diethoxy-phenoxy-acetic acid, bis-TFA salt form. MS (M+H): 523, 4-{2-benzenesulfonylamino-1-[4,5-diethoxy-2-(methanesulfonyl-methyl-amino)-phenyl]-2-oxo-ethylamino}benzamidine as its trifluoroacetic acid salt: MS: (M+H)=604, 4-{2-ethylsulfonylamino-1-[4-isopropoxy,5-ethoxy-phenyl]-2-oxo-ethylamino}benzamidine: MS(M+H)= 463, 4-{2-propylsulfonylamino-1-[4-isopropoxy,5-ethoxy-phenyl]-2-oxo-ethylamino}benzamidine: MS(M+H)= 477, 4-{2-butylsulfonylamino-1-[4-isopropoxy,5-ethoxy-phenyl]-2-oxo-ethylamino}benzamidine: MS(M+H)= 491, 4-{2-(3-propionic acid methyl ester)-sulfonylamino-1-[4-isopropoxy,5-ethoxy-phenyl]-2-oxo-ethylamino]benzamidine: MS(M+H)=521, 4-{2-benzenesulfonylamino-1-[4-isopropoxy,5-ethoxy-phenyl]-2-oxo-ethylamino}benzamidine: MS(M+H)= 511, and 4-[2-benzenesulfonylamino-1-(3,4 diethoxy-phenyl)-2-oxo-ethylamino]-2-hydroxybenzamidine. MS (M+H)= 513;

and acid and base addition salts thereof.

12. A composition comprising the compound of claim 1 and a carrier or excipient.

13. An in vitro method of inhibiting TF/factor VIIa, factor Xa, thrombin or kallikrein activity comprising contacting TF/factor VIIa factor Xa, thrombin or kallikrein with an effective amount of the compound of claim 1.

14. A method of treating a TF/factor VIIa, factor Xa, thrombin or kallikrein mediated disorder, comprising administering to a mammal in need thereof an effective amount of the composition of claim 12.

15. A method of preventing thrombosis or treating abnormal thrombosis, comprising administering to a mammal in need thereof an effective amount of the composition of claim 12.

16. A process for making an amidino compound having the structure:

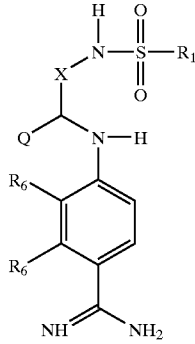

comprising contacting a cyano compound having the structure:

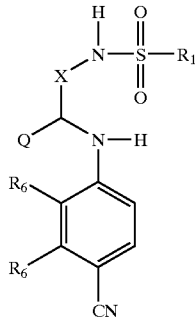

with a reducing agent selected from: (a) hydrogen and Rainey Nickel (RaNi), and (b) hydrogen sulfide, whereby the amidino compound is formed;

wherein

X is C=O or $CH_2$;

$R_1$ is selected from $C_1$–$C_6$ alkyl, $C_2$–$C_6$ alkenyl, $C_2$–$C_6$ alkynyl, $C_3$–$C_6$ cycloalkyl, phenyl, naphthyl, benzyl and heteroaryl, wherein heteroaryl has 5 or 6 ring carbon atoms and 1 or 2 heteroatoms, where the heteroatoms are N, S, or O, and the heteroaryl group is linked to the sulfonamide group by a carbon atom; and where $R_1$ is optionally substituted with 1–3 substituents selected from halo, nitro, $C_1$–$C_6$ alkyl, $NR_7R_8$, $OR_7$, $SR_7$, $C_1$–$C_6$ alkyl-$C(O)OR_7$, $C_1$–$C_6$ alkyl-$OC(O)R_7$, $C_1$–$C_6$ alkyl-$C(O)R_7$, $C_1$–$C_6$ alkyl-$OR_7$, $C_1$–$C_6$ haloalkyl, $C_1$–$C_6$ alkyl-$NR_7R_8$, $C(O)OR_7$, $OC(O)R_7$, $C(O)NR_7R_8$, $OC(O)NR_7R_8$, $NHC(O)R_7$, and $NHC(O)NR_7R_8$;

Q is phenyl optionally substituted with one or more groups selected from halo, nitro, $C_1$–$C_6$ alkyl, $C_2$–$C_6$ alkenyl, $C_2$–$C_6$ alkynyl, $NR_7R_8$, $OR_7$, $SR_7$, $C_1$–$C_6$ alkyl-$C(O)OR_7$, $OC_1$–$C_6$ alkyl-$C(O)OR_7$, $C_1$–$C_6$ alkyl-$OR_7$, $OC_1$–$C_6$ alkyl-$OR_7$, $C_1$–$C_6$ alkyl-$NR_7R_8$, $OC_1$–$C_6$ alkyl-$NR_7R_8$, $C_1$–$C_6$ alkyl-$C(O)NR_7R_8$, $OC_1$–$C_6$ alkyl-$C(O)NR_7R_8$, $C_1$–$C_6$ alkyl-$C(O)R_7$, $OC_1$–$C_6$ alkyl-$C(O)R_7$, $C_1$–$C_6$ haloalkyl, O-aralkyl, $C(O)OR_7$, $C(O)NR_7R_8$, $OC(O)NR_7R_8$, $NHC(O)R_7$, $NHC(O)NR_7R_8$, $NR_7S(O)_2R_1$, $NR_7S(O)_2R_7$, $NR_7S(O)_2$ $C_1$–$C_6$ alkyl-$C(O)OR_7$, $S(O)_2R_7$, and $S(O)_2NR_7R_8$;

$R_6$ is selected from H, $C_1$–$C_6$ alkyl, $C_1$–$C_6$ alkyl-$OR_7$, $C_1$–$C_6$ alkyl-$NR_7R_8$, $C_1$–$C_6$ haloalkyl, halo, cyano, $OR_7$, $SR_7$, $NR_7R_8$, $C(O)OR_7$, $C(O)R_7$ and $OC(O)R_7$; and $R_7$ and $R_8$ are independently H, $C_1$–$C_6$ alkyl, or phenyl.

17. The process of claim 16 wherein the cyano compound is contacted with hydroxylamine ($NH_2OH$), or a salt thereof, to form an intermediate, and the intermediate is contacted with the reducing agent where the reducing agent is hydrogen and RaNi.

* * * * *